(12) United States Patent
Vermot-Desroches et al.

(10) Patent No.: US 9,611,327 B2
(45) Date of Patent: Apr. 4, 2017

(54) ANTI-DR5 FAMILY ANTIBODIES, BISPECIFIC OR MULTIVALENT ANTI-DR5 FAMILY ANTIBODIES AND METHODS OF USE THEREOF

(71) Applicant: INTERNATIONAL—DRUG—DEVELOPMENT—BIOTECH, Dardilly (FR)

(72) Inventors: Claudine Brigitte Fernande Vermot-Desroches, Dardilly (FR); Olivier Frédéric Subiger, Belleville sur Saone (FR); Laurence Françoise Jeanne-Marie Bourdin, Ecully (FR)

(73) Assignee: GENMAB B.V., Utrecht (NL)

( * ) Notice: Subject to any disclaimer, the term of this patent is extended or adjusted under 35 U.S.C. 154(b) by 114 days.

(21) Appl. No.: 14/413,194

(22) PCT Filed: Jul. 9, 2013

(86) PCT No.: PCT/EP2013/064466
§ 371 (c)(1),
(2) Date: Jan. 6, 2015

(87) PCT Pub. No.: WO2014/009358
PCT Pub. Date: Jan. 16, 2014

(65) Prior Publication Data
US 2015/0139997 A1    May 21, 2015

Related U.S. Application Data

(60) Provisional application No. 61/669,866, filed on Jul. 10, 2012.

(30) Foreign Application Priority Data

Jul. 9, 2012    (EP) .................................... 12305821

(51) Int. Cl.
*C07K 16/28* (2006.01)
*C07K 16/30* (2006.01)
(Continued)

(52) U.S. Cl.
CPC .... *C07K 16/2878* (2013.01); *A61K 2039/507* (2013.01); *C07K 2317/24* (2013.01); *C07K 2317/31* (2013.01); *C07K 2317/35* (2013.01); *C07K 2317/54* (2013.01); *C07K 2317/55* (2013.01); *C07K 2317/56* (2013.01); *C07K 2317/565* (2013.01); *C07K 2317/569* (2013.01); *C07K 2317/75* (2013.01)

(58) Field of Classification Search
None
See application file for complete search history.

(56) References Cited

PUBLICATIONS

UniProtKB results for RTS search [online],[retrieved on Jun. 27, 2016], Retrieved from the Internet<URL:http://www.uniprotorg/uniprot/?query=rts&sort=score>.*
Yao et al., Intra-articular injection of recombinant TRAIL induces synovial apoptosis and reduces inflammation in a rabbit knee model of arthritis, Arthritis Res Ther. 8(1): R16, 2006.*
Ichikawa et al., TRAIL-R2 (DR5) mediates apoptosis of synovial fibroblasts in rheumatoid arthritis, J. Immunol. 171:1061-1069, 2003.*

(Continued)

*Primary Examiner* — Claire Kaufman
(74) *Attorney, Agent, or Firm* — Lathrop & Gage LLP; James H. Velema, Esq.

(57) ABSTRACT

Anti-DR5 family member antibodies and bispecific antibodies comprising one or more anti-DR5 family member antibodies are disclosed. These antibodies can be used to trigger cell death on DR5 positive cells.

19 Claims, 27 Drawing Sheets

(51) Int. Cl.
*A61K 39/395* (2006.01)
*A61K 39/00* (2006.01)

(56) References Cited

PUBLICATIONS

Bretz et al., Inflammatory cytokine regulation of TRAIL-mediated apoptosis in thyroid epithelial cells, Cell Death Diff. 9:274-286, 2002.*

Wu et al., Increased serum TRAIL and DR5 levels correlated with lung function and inflammation in stable CPOD patients, Intl. J. COPD, 10:2405-2412, Nov. 2015.*

Mundt et al., Involvement of TRAIL and its receptors in viral hepatits, FASEB, 17:94-96, 2003.*

Nagane, M., et al, "Predominant antitumor effects by fully human anti-TRAIL-receptor2 (DR5) monoclonal antibodies in human glioma cells in vitro and in vivo," Neuro-Oncology, 2010, 12(7):687-700.

Vermot-Desroches, C., et al., "Characterization of monoclonal antibodies directed against trail or trail receptors," Cellular Immunology, 2005, 236(1-2):86-91.

Wang, J., et al., "Characterization of a Novel Anti-DR5 Monocolonal Antibody WD1 with the Potential to Induce Tumor Cell Apoptosis," Cellular & Molecular Immunology, 2008, 5(1):55-60.

European Search Report for EP Application No. 12305821 completed Dec. 4, 2012.

* cited by examiner

| MAb | H4 | | HS683 | | A172 | | T98G | | U87-MG | |
|---|---|---|---|---|---|---|---|---|---|---|
| | % | IFM | % | IFM | % | IFM | % | IFM | % | IFM |
| mIgG1 CTRL | 1+/-1 | 127+/-1 | 2+/-2 | 143+/-11 | 0+/-0 | 119+/-11 | 1+/-1 | 126+/-1 | 0+/-0 | 120+/-2 |
| mDR5-01 | 90+/-1 | 284+/-2 | 87+/-6 | 264+/-30 | 94+/-0 | 296+/-3 | 94+/-0 | 299+/-4 | 75+/-1 | 226+/-4 |
| mDR5-02 | 89+/-0 | 256+/-3 | 85+/-4 | 236+/-20 | 92+/-0 | 279+/-4 | 93+/-1 | 266+/-4 | 82+/-1 | 219+/-17 |
| mDR5-04 | 90+/-0 | 283+/-4 | 88+/-2 | 243+/-13 | 97+/-1 | 308+/-10 | 96+/-1 | 314+/-6 | 80+/-3 | 219+/-13 |
| mDR5-05 | 77+/-8 | 239+/-6 | 79+/-10 | 214+/-23 | 89+/-4 | 268+/-13 | 89+/-0 | 255+/-1 | 70+/-11 | 169+/-12 |

Fig.1

| MAb | A704 | | ACHN | | SW948 | | Caki 1 | | 5637 | | HCT116 | | MCF7 | |
|---|---|---|---|---|---|---|---|---|---|---|---|---|---|---|
| | % | IFM | % | IFM | % | IFM | % | IFM | % | IFM | % | IFM | % | IFM |
| mIgG1 CTRL | 0 | 136 | 1 | 139 | 1 | 208 | 1 | 165 | 1 | 160 | 1 | 172 | 1 | 176 |
| mDR5-01 | 92 | 252 | 93 | 244 | 69 | 316 | 79 | 233 | 78 | 263 | 59 | 254 | 51 | 225 |
| mDR5-05 | 75 | 225 | 82 | 211 | 32 | 245 | 68 | 214 | 51 | 188 | 43 | 224 | 33 | 192 |

Fig.2

```
<----------------------------------- H-FR1-IMGT ----------------------------------->
GAG GTG CAA CTG CAG CAA TCA GGA GCA GAA GTC GTA AAG CCC GGT GCC TCC GTT AAA CTT AGC
 E   V   Q   L   Q   Q   S   G   A   E   V   V   K   P   G   A   S   V   K   L   S
                       <----- H-CDR1-IMGT ----->
TGC AAA GCA AGT GGG TTT AAT ATC AAA GAT ACA TTC ATC CAT TGG GTC AAA CAG GCA CCA GGC
 C   K   A   S   G   F   N   I   K   D   T   F   I   H   W   V   K   Q   A   P   G
<--- H-FR2-IMGT ---->                                      <----------
CAG GGC CTT GAA TGG ATC GGT CGC ATT GAC CCA GCT AAT GGA AAC ACT AAG TAT GAC CCT AAG
 Q   G   L   E   W   I   G   R   I   D   P   A   N   G   N   T   K   Y   D   P   K
---------- H-CDR2-IMGT ----------->  <------------- H-FR3-IMGT ------------
TTC CAG GGA AAG GCT ACA ATT ACA ACA GAT ACT TCC AAT ACC GCT TAC ATG GAG CTG TCT
 F   Q   G   K   A   T   I   T   T   D   T   S   N   T   A   Y   M   E   L   S
-----------------------------------------------> <----- H-CDR3-IMGT -----
TCC TTG CGG TCT GAG GAT ACT GCT GTG TAT TAC TGT GTA CGT GGG CTG TAC ACA TAT TAC TTC
 S   L   R   S   E   D   T   A   V   Y   Y   C   V   R   G   L   Y   T   Y   Y   F

GAT TAT TGG GGC CAG GGG ACT CTT GTA ACC GTT TCC TCC    (SEQ ID NO:35)
 D   Y   W   G   Q   G   T   L   V   T   V   S   S
```

Figure 25

```
<-------------------------------- L-FR1-IMGT --------------------------------
GAG ATT GTT ATG ACA CAG TCC CCT GCT GCT CTG TCT GTT AGT CCA GGC GAA AGA GCT ACA CTG
 E   I   V   M   T   Q   S   P   A   A   L   S   V   S   P   G   E   R   A   T   L

---------------- L-CDR1-IMGT ----------------            <---------- L-FR2-IMGT ----------
TCA TGT AGG GCC TCT CAG TCT ATT AGC AAT AAC CTG CAC TGG TAT CAG CAA AAG CCA GGT CAA
 S   C   R   A   S   Q   S   I   S   N   N   L   H   W   Y   Q   Q   K   P   G   Q

------------------->  L-CDR2-IMGT ---------
GCC CCC AGG CTC CTG ATT AAG TTT GCA TCT CAA AGT ATT ACA GGA ATC CCT GCT CGG TTC AGC
 A   P   R   L   L   I   K   F   A   S   Q   S   I   T   G   I   P   A   R   F   S

----------- L-FR3-IMGT ----------
GGC TCC GGG AGT GGA ACC GAG TTT ACA CTC ACA ATC TCA AGC CTC CAG TCC GAA GAC TTC GCC
 G   S   G   S   G   T   E   F   T   L   T   I   S   S   L   Q   S   E   D   F   A

--------------------> L-CDR3-IMGT
GTA TAT TAC TGT CAG CAG GGC AAC TCT TGG CCC TAC ACC TTC GGT CAG GGA ACC AAG CTG GAG
 V   Y   Y   C   Q   Q   G   N   S   W   P   Y   T   F   G   Q   G   T   K   L   E

ATC AAG  (SEQ ID NO:37)
 I   K
```

Figure 26

```
---- H-FR1-IMGT -------------------------------------------------
CAA GTT CAG TTG GTA CAA TCA GGT GCA GAA GTT AAA AAG CCA GGG GCA TCT GTT AAA GTG TCT
 Q   V   Q   L   V   Q   S   G   A   E   V   K   K   P   G   A   S   V   K   V   S

H-CDR1-IMGT
TGC AAG GCC TCC GGC TTT AAT ATC AAG GAC ACA CAC ATG CAT TGG GTG CGC CAG GCC CCA GGC
 C   K   A   S   G   F   N   I   K   D   T   H   M   H   W   V   R   Q   A   P   G

---- H-FR2-IMGT --------->                         H-CDR2-IMGT
CAG CGA CTG GAG TGG ATT GGG CGT ATT GAC CCC GCC AAC GGC AAC ACC GAG TAT GAC CAG AAG
 Q   R   L   E   W   I   G   R   I   D   P   A   N   G   N   T   E   Y   D   Q   K

H-FR3 - IMGT
TTT CAG GGC CGT GTA ACC ATC ACC GTC GAT ACC TCA GCA TCA ACC GCT TAC ATG GAG CTT TCA
 F   Q   G   R   V   T   I   T   V   D   T   S   A   S   T   A   Y   M   E   L   S

H-CDR3-IMGT
TCT CTT CGG TCC GAA GAC ACA GCC GTC TAT TAC TGC GCT CGA TGG GGA ACA AAC GTT TAC TTT
 S   L   R   S   E   D   T   A   V   Y   Y   C   A   R   W   G   T   N   V   Y   F

GCA TAT TGG GGT CAG GGT ACT CTC GTC ACC GTG AGC AGT   (SEQ ID NO:39)
 A   Y   W   G   Q   G   T   L   V   T   V   S   S

Figure 27
```

```
                                           <----------------------------------- L-FR1-IMGT ---------------------------
GAT ATT CAA CTT ACA CAA TCT CCC TCT TCT CTC TCC GCT TCA GTA GGG GAT AGA GTG ACC ATC
 D   I   Q   L   T   Q   S   P   S   S   L   S   A   S   V   G   D   R   V   T   I

----> L-CDR1-IMGT <----                                      ----- L-FR2-IMGT ------
ACT TGC TCT GCT TCT TCC AGC GTG TCA TAT ATG TAT TGG TAT CAG CAA AAG CCC GGC AAG GCA
 T   C   S   A   S   S   S   V   S   Y   M   Y   W   Y   Q   Q   K   P   G   K   A

----> L-CDR2-IMGT <----                                  ----- L-FR3-IMGT -----
CCT AAA CCA TGG ATT TAC AGA ACC AGC AAT CTT GCC AGT GGT GTT CCA AGT AGG TTT AGC GGC
 P   K   P   W   I   Y   R   T   S   N   L   A   S   G   V   P   S   R   F   S   G

TCC GGC TCT GGT ACA GAC TTT ACC CTG ACT ATC TCC TCT CTC CAG CCC GAG GAT TTT GCC ACA
 S   G   S   G   T   D   F   T   L   T   I   S   S   L   Q   P   E   D   F   A   T

----> L-CDR3-IMGT <----
TAT TAC TGC CAG CAA TAC CAT TCT TAC CCT CCA ACT TTT GGA GGT GGC ACT AAG GTG GAG ATC
 Y   Y   C   Q   Q   Y   H   S   Y   P   P   T   F   G   G   G   T   K   V   E   I

AAG    (SEQ ID NO:41)
 K

Figure 28
```

ANTI-DR5 FAMILY ANTIBODIES, BISPECIFIC OR MULTIVALENT ANTI-DR5 FAMILY ANTIBODIES AND METHODS OF USE THEREOF

RELATED APPLICATIONS

This application is a 371 filing of International Application No. PCT/EP2013/064466, filed Jul. 9, 2013, which claims priority to U.S. Provisional Patent Application No. 61/669,866, filed Jul. 10, 2012 and European Patent Application No. 12305821.6, filed Jul. 9, 2012, the contents of each of which are incorporated herein by reference in their entirety.

FIELD OF THE INVENTION

The present invention relates to the fields of immunology, oncology, and more specifically, to monospecific, bispecific or multivalent antibody molecules that can be used to advantage in the treatment of various cancers, autoimmune diseases, and infectious diseases that express DR5 antigen. The present invention is related to novel polypeptides binding specifically to the DR5 receptor also called TRAIL receptor 2. The invention relates in particular to a polypeptide having two different binding domains or a combination of polypeptides having these different binding domains, which bind to different epitopes of the DR5 receptor, whereby apoptosis is induced. The invention also relates to pharmaceutical compositions containing these polypeptides and the treatment of cancer, autoimmune diseases and viral infections using these polypeptides and compositions.

BACKGROUND OF THE INVENTION

Apoptosis, or programmed cell death, is a physiologic process essential to the normal development and homeostasis of multicellular organisms. Derangements of apoptosis contribute to the pathogenesis of several human diseases including cancer, neurodegenerative disorders, and acquired immune deficiency syndrome.

The tumor necrosis factor (TNF)-related apoptosis-inducing ligand (TRAIL), a member of the TNF superfamily of cytokines, is a type 2 membrane protein that is expressed in the majority of normal tissues and can undergo protease cleavage, resulting in a soluble form able to bind to TRAIL receptors, (Wiley S R. et al., Immunity. 1995; 3:673-682; Daniel P T et al., J Immunol. 1994; 152:5624).

Ligands of this family generally recognize and bind to a limited subset of cognate receptors on the cell surface, leading to signal transduction cascades downstream of the receptor, allowing the activation of a large panel of signalling pathways including NF-kB or caspase activation. TRAIL induces apoptosis of certain transformed cells, including a number of different types of cancer cells as well as virally infected cells, while not inducing apoptosis of a number of normal cell types and is thus of particular interest in the development of cancer therapies, (Walczak et al., Nature Medecine. 1999; 5/157-163, Ashkenazi A. et al., J Clin Invest. 1999; 104:155).

There are four known cell surface receptors for TRAIL. TRAIL Receptor 1 (TRAIL-R1, DR4) and Trail Receptor 2 (TRAIL-R2, DR5, Apo-2, TRICK2, Killer, TR6, Tango-63) have a cytoplasmic death domain and are able to trigger apoptosis in tumor cells via downstream caspase activation. The other two receptors, TRAIL Receptor 3 (TRAIL-R3, DcR1, TR5, TRIDD, LIT) and TRAIL Receptor 4 (TRAIL-R4, DcR2, TRUNDD) lack a cytoplasmic death domain and do not mediate apoptosis. In addition, osteoprotegerin (OPG), a soluble (secreted) member of the TNF receptor family of proteins, also binds TRAIL.

The intracytoplasmic domains of DR4 and DR5 each include a so-called death domain. After activation of the receptors DR4 and DR5, the fas-associated death domain adapter molecule is recruited to the receptor, leading to an autoproteolytic cleavage and activation of initiator caspase-8. DR4 and DR5 have been reported to transduce an apoptotic signal to TRAIL sensitive cancer cells, upon binding of TRAIL. Active caspase-8 in turn triggers the proteolytic activation of downstream caspases including caspase-3. Downstream caspases ultimately degrade a broad range of cellular proteins, and apoptosis is finalized.

Expression of either DR4 or DR5 is frequently detected in human cancers, including colon, gastric, pancreatic, ovarian, breast, and non-small-cell lung cancer with low or no expression in normal tissues.

In the development or progression of many diseases it is often the case that cells are not deleted. In many autoimmune diseases and inflammatory conditions, the surviving activated cells attack normal tissues or cells. Further, progression of tumorigenesis and the proliferative pannus formation of rheumatoid arthritis are characterized by the unchecked proliferation of cells. Thus insufficient apoptosis leads to the development of disease, and the uses of apoptosis-inducing ligand or agonistic MAb to enhance apoptosis are considered as a potential therapeutic strategy for eliminating those unwanted cells TRAIL induces apoptosis in a wide range of haematopoietic and solid tumor cells, while sparing most normal cells. TRAIL has strong apoptosis-inducing activity against cancer cells in vitro and potent antitumor activity against tumor xenografts of various cancers in vivo.

TRAIL and its derivatives, including agonistic antibodies targeting TRAIL receptors are attractive compounds for cancer therapy due to their ability to induce tumor regression without significant side effects.

There are many instances in the patent literature of efforts to use polypeptides derived from the TRAIL ligand as a therapy against cancerous cells (US20090131317; U.S. Pat. No. 6,469,144; U.S. Pat. No. 6,740,739; US20070026000; U.S. Pat. No. 6,444,640; US20050244857; US20050233958; U.S. Pat. No. 7,736,637).

TRAIL polypeptides have been used to induce the TRAIL apoptotic pathway, but they have the drawback of a short half-life.

Currently, a great deal of attention has focused on the development of novel immunotherapy strategies for the treatment of cancer. One such strategy is antibody-based cancer therapy.

The most prominent determinant of the above targeting properties is the size of the antibody-based molecule relative the degree of specificity, the retention in tumors and their clearance. Another important feature of antibody-based molecules is valence, as significantly greater tumor retention has been associated with multivalent binding to target, (Adams et al., Cancer Res. 1993; 51:6363-6371; Wolf et al., Cancer Res. 1993; 53:2560-2565).

As mentioned earlier, agonistic antibodies against DR4 or DR5 have been produced and represent a new generation of cancer therapy. Works have been conducted also on the use of agonistic antibodies directed against the TRAIL receptors in order to induce the TRAIL apoptotic pathway.

Agonistic monoclonal antibodies that specifically bind to DR4 or DR5 are supposed to be able to directly induce apoptosis of targeted tumor cells, (Buchsbaum D J et al., *Future Oncol*. 2006; 2:493; Rowinsky E K et al., *J Clin Oncol*. 2005; 23:9394).

Other patents relate to the use of agonistic antibodies directed against DR4 or DR5, or DR4 and DR5, or to the combined use of antibodies against DR5 and another chemotherapeutic agent: US20040147725; US 20090022707; US20080248037; US20020155109; U.S. Pat. No. 6,461,823; U.S. Pat. No. 6,872,568; U.S. Pat. No. 7,064,189; U.S. Pat. No. 6,521,228; U.S. Pat. No. 7,704,502.

Combined treatment with agonistic antibodies directed against different TRAIL receptors, for example DR4 and DR5, have been developed as well. Agonistic bispecific antibodies that bind DR4 or DR5 (or hybridomas producing such agonistic MAbs) may be employed as starting materials in various procedures (WO 2002/0155109).

These include anti-DR5 MAb lexatumumab, (Plummer R. et al., *Clin Cancer Res*. 2007; 13:6187), the anti-DR5 MAb apomab, (Adams C. et al., *Cell Death Differ*. 2008; 15:751), the anti-DR5 MAb LBy135, (Li J. et al., *AACR Meeting Abstracts*. 2007. Abstract 4874), the anti-DR5 MAb WD-1, (Wang J. et al., *Cell Mol Immunol*. 2008; 5:55) and the anti-DR5 MAb AMG655, (Wall J. et al., *AACR Meeting Abstracts*. 2008. Abstract 1326, Kaplan-Lefko P. et al., *AACR Meeting Abstracts*. 2008. Abstract 399). A consistent finding from all these studies is the considerable variability in the sensitivity of various tumor cell lines to anti-DR5-mediated cytotoxicity.

Anti-DR4 or anti-DR5 agonistic antibodies, including mapatumumab or lexatumumab respectively are also well tolerated in patients (Herbst R. S. et al., *J Clin Oncol*. 2006; 24(18S)/3013; Hotte S. J. et al., *Clin Cancer Res*. 2008; 14/3450-3455; Wakelee H. A et al., *Ann Oncol*. 2010; 21/376-381; Fox N. L. et al., *Expert Opin Biol Ther*. 2010; 10/1-18).

Lexatumumab (also known as ETR2-ST01) is an agonistic human monoclonal antibody against DR5 used in the treatment of cancer. HGS-ETR2 antibodies were generated by HGS through collaboration with Cambridge Antibody Technology.

Tigatuzumab (CS-1008) is a humanized IgG1 monoclonal antibody composed of the CDR regions of mTRA-8. The murine anti-DR5 monoclonal antibody, TRA-8 (mTRA-8), was selected from a series of anti-DR5 monoclonal antibodies based on its specificity, ability to trigger apoptosis in vitro without the use of crosslinking reagents, and lack of toxicity to human hepatocytes, (Buchsbaum D J et al., *Clin Cancer Res*. 2003; 9:3731; Ichikawa K. et al., *Nat Med*. 2001; 7:954).

Tigatuzumab mediates a very similar pattern of in vitro cytotoxicity and in vivo antitumor efficacy as mTRA-8. It was shown to have potent in vitro cytotoxicity to a variety of human tumor cell lines and in vivo antitumor efficacy in murine xenograft models of human cancers. Its in vitro cytotoxicity and in vivo antitumor efficacy can be substantially enhanced in combination with a variety of chemotherapeutic agents and/or radiation, (Buchsbaum D J et al., *Clin Cancer Res*. 2003; 9:3731; DeRosier L C et al., *Clin Cancer Res*. 2007; 13:5535s).

Anti-DR4 and anti-DR5 antibodies have been tested in associations, together or with other chemotherapeutic agents or therapies. A combined treatment of colorectal tumors with two agonistic antibodies HGS-ETR1 (anti-DR4) and HGS-ETR2 (anti-DR5) and radiotherapy let to enhanced effects in vitro and dose-dependent growth delay in vivo (Marini P et al., *Oncogene*. 2006; 25 (37):5145-54). Fully human agonistic antibodies to DR4 and DR5 demonstrated in primary and cultured lymphoma cells induction of apoptosis and enhancement of doxorubicin- and bortezomib-induced cell death (Georgakis G V et al., *Oncogene*. 2006; 25(37):5145-54).

It has been found that the expression of DR5 and susceptibility to TRAIL-induced apoptosis of breast cancer cells is enhanced by the radiation, suggesting that combined with radiation, the efficiency of TRAIL would be increased in cancer therapy (Chinnaiyan A. M et al., *PNAS*. 2000; 97/1754-1759).

The combination of antibody and chemotherapy usually enhances the degree of apoptosis and can partially reverse resistance in some cell lines (Buchsbaum D J et al., *J Clin Cancer Res*. 2003; 9:3731; DeRosier L C et al., *Clin Cancer Res*. 2007; 13:5535s; Oliver P G et al., *Clin Cancer Res*. 2008; 14:2180; Derosier L C et al., *Mol Cancer Ther*. 2007; 6:3198; Long J W. et al., *J Surg Res*. 2007; 137:167).

SUMMARY OF THE INVENTION

The present inventors have now found that unexpectedly, it is possible to induce the DR5 apoptotic pathway by using two antibodies directed against at least two different epitopes of the DR5 receptor. The binding to both epitopes on the same receptor has an agonistic action on the receptor and induces apoptosis in an efficient way. Combination of antibodies DR5-01 and DR5-05 as disclosed herein revealed a stronger agonistic action than the ligand itself.

An unexpected and synergistic action has been observed by using two antibodies directed each against a different epitope on the DR5 receptor, with respect to one antibody against one single epitope. Without wishing to be bound to the theory, it is postulated that the binding to the two epitopes of DR5 allows for a synergistic agonist function, leading to an unexpectedly elevated apoptosis induction. It has been found that the unexpected and synergistic action may be beneficial for therapeutic treatment or for integration to a therapeutic protocol. It has thus been found that the combination of the antibodies may lead to a synergic increase of inhibition of cancer cells proliferation in particular in glioma. It has also been found that the combination of the antibodies and a chemotherapeutic drug may lead to a synergic increase of inhibition of cancer cells proliferation in the case of cancers that are difficult to treat, such as glioma, lung and breast cancers that more or less resist to chemotherapeutic drugs. It has also been found that the combination of antibodies and drug may allow getting a therapeutic effect, such as inhibition of cell proliferation, which is stably obtained over a wide range of drug and/or antibodies dosages.

It is thus now possible to provide for pharmaceutical compositions comprising two polypeptides or antibodies acting as agonist by binding to the two different epitopes on DR5, or bispecific antibodies acting as agonist by binding to the two different epitopes on DR5 and pharmaceutical compositions containing the same.

An "agonist" or an "agonistic polypeptide or antibody" for a natural receptor is a compound which binds the receptor to form a receptor-agonist complex and which activates said receptor, initiating a pathway signaling and further biological process. In the context of the present invention, an agonist function is obtained owing the simultaneous or sequential interaction between the polypeptides or antibodies of the invention and two different epitopes of the DR5 receptor, initiating the DR5 apoptosis pathway.

An object of the invention is thus a composition comprising two polypeptides, or antibodies or fragment thereof, both having the capability to bind to DR5, a first polypeptide or antibody comprising a first antigen-binding site that binds to a first epitope of said DR5, and a second polypeptide or antibody comprising a second different antigen-binding site that binds to a second epitope of said DR5. Each of said first and second antigen-binding sites binds to a different epitope on the same DR5 molecule. The two polypeptides, or antibodies or fragments thereof are for a simultaneous, separate or sequential administration to a mammal, including human.

The composition or pharmaceutical composition may further contain a pharmaceutically acceptable carrier, diluent, or excipient. The polypeptides or antibodies are synergistically agonistic in combination, which means that they have the capability upon binding to both epitopes of a DR5 molecule to induce the DR5 apoptotic pathway.

An object of the invention is also a bispecific or biparatopic antibody, or fragment thereof, having the capability to bind to DR5, said antibody comprising a first antigen-binding site that binds to a first epitope of said DR5, and a second different antigen-binding site that binds to a second epitope of said DR5. Each of said first and second antigen-binding sites binds to a different epitope on the same DR5 molecule. The polypeptides or antibodies are synergistically agonistic in combination, which means that they have the capability upon binding of both to their specific epitopes of a DR5 molecule to induce the DR5 apoptotic pathway.

The invention encompasses the binding of one bispecific antibody to the two different epitopes of the same DR5 molecule, or of two bispecific antibodies to the two epitopes of the same DR5 molecule, one antibody to a first epitope, the second to the second epitope of the same DR5 molecule.

The bispecific antibody may be formulated in a pharmaceutical composition further containing a pharmaceutically acceptable carrier, diluent, or excipient.

Without wishing to be bound to theory, it is deemed that, regarding the mechanism of action, antibody combination or bispecific antibodies according to the invention may promote DR5 clustering. These components may promote DR5 amassing of higher concentration compared with a monospecific antibody.

Antibody combination or bispecific antibodies may promote also a conformation change inducing a higher incidence to trigger apoptosis signalling or to reverse the resistance of cancer cell to the apoptosis. These components may promote DR5 amassing of higher concentration compared with a monospecific antibody.

Another object of the invention encompasses the binding at least of two, three, four, five or more monovalent binding polypeptides, or antibodies or fragment thereof, both having the capability to bind to DR5, a first polypeptide or antibody comprising a first antigen-binding site that binds to a first epitope of said DR5, and a second polypeptide or antibody comprising a second different antigen-binding site that binds to a second epitope of said DR5.

Another object of the invention is thus a composition comprising at least one chemotherapeutic drug and two polypeptides, or antibodies or fragment thereof, both having the capability to bind to DR5, a first polypeptide or antibody comprising a first antigen-binding site that binds to a first epitope of said DR5, and a second polypeptide or antibody comprising a second different antigen-binding site that binds to a second epitope of said DR5. Each of said first and second antigen-binding sites binds to a different epitope on the same DR5 molecule. The drug and the two polypeptides, or antibodies or fragments thereof are for a simultaneous, separate or sequential administration to a mammal, including human. In this object, the two polypeptides may be replaced by a bispecific or biparatopic antibody, or fragment thereof, as disclosed herein.

The polypeptides, especially antibodies, according to the invention may be further defined by the CDRs of the VH and VL regions of the murine antibodies DR5-01 and DR5-05 or by their complete VH and VL regions.

An object of the invention is to a composition comprising at least one or two polypeptides binding specifically a DR5 receptor, wherein the at least one or two polypeptides comprise two immunoglobulin binding domains comprising:

a first binding domain comprising a pair of VH and VL chains wherein
the VH chain contains a CDR1 comprising or consisting of sequence SEQ ID NO: 13, a CDR2 comprising or consisting of sequence SEQ ID NO: 14 CDR1, a CDR3 comprising or consisting of sequence SEQ ID NO: 15; and the VL chain contains a CDR1 comprising or consisting of sequence SEQ ID NO: 16, a CDR2 comprising or consisting of sequence FAS, a CDR3 comprising or consisting of sequence SEQ ID NO: 17; or
wherein the VH chain contains a CDR1 comprising or consisting of sequence SEQ ID NO:22, a CDR2 comprising or consisting of sequence SEQ ID NO: 23, a CDR3 comprising or consisting of sequence SEQ ID NO: 24; and the VL chain contains a CDR1 comprising or consisting of sequence SEQ ID NO: 25, a CDR2 comprising or consisting of sequence SEQ ID NO: 26, a CDR3 comprising or consisting of sequence SEQ ID NO: 17, or
wherein the VH chain contains a CDR1 comprising or consisting of sequence SEQ ID NO: 32, a CDR2 comprising or consisting of sequence SEQ ID NO: 14, a CDR3 comprising or consisting of sequence SEQ ID NO: 24; and the VL chain contains a CDR1 comprising or consisting of sequence SEQ ID NO: 16, a CDR2 comprising or consisting of sequence FAS, a CDR3 comprising or consisting of sequence SEQ ID NO: 17,
and
a second binding domain comprising a pair of VH and VL chains wherein
the VH chain contains a CDR1 comprising or consisting of sequence SEQ ID NO: 18, a CDR2 comprising or consisting of sequence SEQ ID NO: 14, a CDR3 comprising or consisting of sequence SEQ ID NO: 19; and the VL chain contains a CDR1 comprising or consisting of sequence SEQ ID NO: 20, a CDR2 comprising or consisting of sequence RTS, a CDR3 comprising or consisting of sequence SEQ ID NO: 21, or
wherein the VH chain contains a CDR1 comprising or consisting of sequence SEQ ID NO: 27, a CDR2 comprising or consisting of sequence SEQ ID NO: 28, a CDR3 comprising or consisting of sequence SEQ ID NO: 29; and the VL chain contains a CDR1 comprising or consisting of sequence SEQ ID NO: 30, a CDR2 comprising or consisting of sequence SEQ ID NO: 31, a CDR3 comprising or consisting of sequence SEQ ID NO: 21, or
wherein the VH chain contains a CDR1 comprising or consisting of sequence SEQ ID NO: 33, a CDR2 comprising or consisting of sequence SEQ ID NO: 14, a CDR3 comprising or consisting of sequence SEQ ID NO: 29; and the VL chain contains a CDR1 comprising or consisting of sequence SEQ ID NO: 20, a CDR2 comprising or consisting of sequence RTS, a CDR3 comprising or consisting of sequence SEQ ID NO: 21, wherein the at least one polypeptide comprises both immunoglobulin binding domains, or the at least two polypeptides comprise a first polypeptide comprising the first binding domain and a second polypeptide comprising the second binding domain for a simultaneous, separate or sequential administration to a mammal, including man, and a pharmaceutically carrier, diluent or excipient. In an embodiment, the composition comprises further a chemotherapeutic drug for a simultaneous, separate or sequential administration to a mammal, including man.

Other objects of the invention are the individual polypeptides or antibodies and their various combinations in accordance with the invention, kits comprising at least two polypeptides or antibodies, and kits comprising at least one polypeptide or antibody and at least one drug, wherein antibodies or polypeptides and drugs are separated or not.

The polypeptides or antibodies of the invention may comprise one or several, preferably two, binding sites or domains or paratopes. An object of the present invention is a polypeptide binding specifically a DR5 receptor, comprising one or more, preferably one or two, immunoglobulin binding domain(s) comprising:

a binding domain comprising a pair of VH and VL chains wherein:

the VH chain contains a CDR1 comprising or consisting of sequence SEQ ID NO: 13, a CDR2 comprising or consisting of sequence SEQ ID NO: 14, a CDR3 comprising or consisting of sequence SEQ ID NO: 15; and the VL chain contains a CDR1 comprising or consisting of sequence SEQ ID NO: 16, a CDR2 comprising or consisting of sequence FAS, a CDR3 comprising or consisting of sequence SEQ ID NO: 17 (DR5-01 type CDRs), or the VH chain contains a CDR1 comprising or consisting of sequence SEQ ID NO:22, a CDR2 comprising or consisting of sequence SEQ ID NO: 23, a CDR3 comprising or consisting of sequence SEQ ID NO: 24; and the VL chain contains a CDR1 comprising or consisting of sequence SEQ ID NO: 25, a CDR2 comprising or consisting of sequence SEQ ID NO: 26, a CDR3 comprising or consisting of sequence SEQ ID NO: 17, (DR5-01 type CDRs), or the VH chain contains a CDR1 comprising or consisting of sequence SEQ ID NO: 32, a CDR2 comprising or consisting of sequence SEQ ID NO: 14, a CDR3 comprising or consisting of sequence SEQ ID NO: 24; and the VL chain contains a CDR1 comprising or consisting of sequence SEQ ID NO: 16, a CDR2 comprising or consisting of sequence FAS, a CDR3 comprising or consisting of sequence SEQ ID NO: 17 (DR5-01 type CDRs);

and/or a binding domain comprising a pair of VH and VL chains wherein:

the VH chain contains a CDR1 comprising or consisting of sequence SEQ ID NO: 18, a CDR2 comprising or consisting of sequence SEQ ID NO: 14, a CDR3 comprising or consisting of sequence SEQ ID NO: 19; and the VL chain contains a CDR1 comprising or consisting of sequence SEQ ID NO: 20, a CDR2 comprising or consisting of sequence RTS, a CDR3 comprising or consisting of sequence SEQ ID NO: 21 (DR5-05 type CDRs), or the VH chain contains a CDR1 comprising or consisting of sequence SEQ ID NO: 27, a CDR2 comprising or consisting of sequence SEQ ID NO: 28, a CDR3 comprising or consisting of sequence SEQ ID NO: 29; and the VL chain contains a CDR1 comprising or consisting of sequence SEQ ID NO: 30, a CDR2 comprising or consisting of sequence SEQ ID NO: 31, a CDR3 comprising or consisting of sequence SEQ ID NO: 21 (DR5-05 type CDRs), or the VH chain contains a CDR1 comprising or consisting of sequence SEQ ID NO: 33, a CDR2 comprising or consisting of sequence SEQ ID NO: 14, a CDR3 comprising or consisting of sequence SEQ ID NO: 29; and the VL chain contains a CDR1 comprising or consisting of sequence SEQ ID NO: 20, a CDR2 comprising or consisting of sequence RTS, a CDR3 comprising or consisting of sequence SEQ ID NO: 21 (DR5-05 type CDRs). The binding domain is best defined by the VH and VL chains comprising the CDRs defined based on the same method, either IMGT®, Kabat® or common numbering system, see CDR table infra.

The VH and VL chains together define a single binding site. Each one of these binding domain binds specifically to a different epitope on the DR5 receptor. The polypeptides are synergistically agonistic, which means that they have the capability upon binding to both epitopes of a DR5 molecule to induce the DR5 apoptotic pathway.

By "immunoglobulin binding domain" or "binding domain" it is meant the paratope of an immunoglobulin made of the two variable light (VL) and variable heavy (VH) chains. The paratope is able to specifically bind to the targeted epitope.

In accordance with the invention, the VL and VH chains have a conventional structure of a light chain or a heavy chain of an immunoglobulin, with the framework regions FR. The structure may be defined as the structure FR1-CDR1-FR2-CDR2-FR3-CDR3-FR4. In a preferred embodiment, the polypeptide of the invention comprises one or more, preferably one or two, immunoglobulin binding domain(s) comprising the VH+VL region of mDR5-01 and/or the VH+VL region of mDR5-05. In an embodiment, the polypeptide comprise one or two binding domain(s) comprising the VH+VL region of mDR5-01. In an embodiment, the polypeptide comprise one or two binding domain(s) comprising the VH+VL region of mDR5-05. In an embodiment, the polypeptide comprise two binding domain(s) comprising the VH+VL region of mDR5-05, on the one hand, and the VH+VL region of mDR5-01, on the other hand. In a preferred embodiment, the polypeptide of the invention comprises one or more, preferably one or two, immunoglobulin binding domain(s) comprising the VH+VL region of HzDR5-01 and/or the VH+VL region of HzDR5-05. In an embodiment, the polypeptide comprise one or two binding domain(s) comprising the VH+VL region of HzDR5-01. In an embodiment, the polypeptide comprise one or two binding domain(s) comprising the VH+VL region of HzDR5-05. In an embodiment, the polypeptide comprise two binding domain(s) comprising the VH+VL region of HzDR5-05, on the one hand, and the VH+VL region of HzDR5-01, on the other hand.

The anti-DR5 polypeptide thus comprises one or two binding domains. In an embodiment, the binding domains are specific of the same epitope on the DR5 receptor. These binding domains comprise the same set of 3 CDRs on the VH and VL as disclosed and provided therein and may be identical or slightly different in the framework regions, as soon as this does not affect the specificity to bind the targeted epitope.

The anti-DR5 polypeptide may be in particular an antibody, preferably a monoclonal antibody, or a suitable antibody fragment, such as a Fv, a Fab, a F(ab')$_2$, a single-chain variable fragment (scFv).

The invention also encompasses the combined use of polypeptides or antibodies or of bispecific polypeptides or antibodies or fragments and the like, making use of the synergic activity linked to binding to the two epitopes revealed by the present invention. This use may be further combined with the administration of a chemotherapeutic drug, as disclosed herein.

Another object of the invention encompasses the binding at least of two, three, four, five or more monovalent binding polypeptides, or antibodies or fragment thereof, both having the capability to bind to DR5, a first polypeptide or antibody comprising a first antigen-binding site that binds to a first epitope of said DR5, and a second polypeptide or antibody comprising a second different antigen-binding site that binds to a second epitope of said DR5.

Thus, another object of the invention is a composition comprising two polypeptides, or antibodies or fragment thereof, both having the capability to bind to DR5, a first polypeptide or antibody comprising a first antigen-binding site that binds to a first epitope of said DR5, this first epitope being the one to which specifically binds a binding domain comprising a pair of VH and VL chains wherein the VH chain contains a CDR1 of sequence SEQ ID NO: 13, a CDR2 of sequence SEQ ID NO: 14 CDR1, a CDR3 of sequence SEQ ID NO: 15; and the VL chain contains a CDR1 of sequence SEQ ID NO: 16, a CDR2 of sequence FAS, a CDR3 of sequence SEQ ID NO: 17, and a second polypeptide or antibody comprising a second different antigen-binding site that binds to a second epitope of said DR5, this epitope being the one to which specifically binds a binding domain comprising a pair of VH and VL chains wherein the VH chain contains a CDR1 of sequence SEQ ID NO: 18, a CDR2 of sequence SEQ ID NO: 14, a CDR3 of sequence SEQ ID NO: 19; and the VL chain contains a CDR1 of sequence SEQ ID NO: 20, a CDR2 of sequence RTS, a CDR3 of sequence SEQ ID NO: 21, for a simultaneous, separate or sequential administration to a mammal, including man. As an alternative, one may replace herein above the definition of the CDRs by those according to Kabat® or Common numbering System as per Tables 1 and 2.

Another object of the invention is a bispecific antibody, or fragment thereof, having the capability to bind to DR5, said antibody comprising a first antigen-binding site that binds to a first epitope of said DR5, this first epitope being the one to which specifically binds a binding domain comprising a pair of VH and VL chains wherein the VH chain contains a CDR1 of sequence SEQ ID NO: 13, a CDR2 of sequence SEQ ID NO: 14 CDR1, a CDR3 of sequence SEQ ID NO: 15; and the VL chain contains a CDR1 of sequence SEQ ID NO: 16, a CDR2 of sequence FAS, a CDR3 of sequence SEQ ID NO: 17, and a second different antigen-binding site that binds to a second epitope of said DR5, this epitope being the one to which specifically binds a binding domain comprising a pair of VH and VL chains wherein the VH chain contains a CDR1 of sequence SEQ ID NO: 18, a CDR2 of sequence SEQ ID NO: 14, a CDR3 of sequence SEQ ID NO: 19; and the VL chain contains a CDR1 of sequence SEQ ID NO: 20, a CDR2 of sequence RTS, a CDR3 of sequence SEQ ID NO: 21. As an alternative, one may replace hereinabove the definition of the CDRs by those according to Kabat® or Common numbering System as per Tables 1 and 2.

Another object of the invention is the method of treatments, comprising the administration of an effective or sufficient amount of at least two polypeptides or antibodies as disclosed herein, or of at least one bispecific or biparatopic polypeptide or antibody as disclosed herein, or of at least two polypeptides or antibodies and at least one drug, as disclosed herein, or of at least one bispecific or biparatopic polypeptide or antibody and at least one drug, as disclosed herein. By treatment is meant in particular treatment of various cancers, autoimmune diseases, infectious diseases that express DR5 antigen.

DEFINITIONS

The terms "apoptosis" and "apoptotic activity" are used in a broad sense and refer to the orderly or controlled form of cell death in mammals that is typically accompanied by one or more characteristic cell changes, including condensation of cytoplasm, loss of plasma membrane microvilli, segmentation of the nucleus, degradation of chromosomal DNA or loss of mitochondrial function. This activity can be determined and measured, for instance, by cell viability assays, FACS analysis or DNA electrophoresis, and more specifically by binding of annexin V, fragmentation of DNA, cell shrinkage, dilation of endoplasmic reticulum, cell fragmentation, and/or formation of membrane vesicles (called apoptotic bodies).

As used herein, the term "synergy" or "synergism" or "synergistically" refers to the interaction of two or more agents so that their combined effect is greater than the sum of their individual effects.

The term "agonist" and "agonistic" when used herein refer to or describe a molecule which is capable of, directly or indirectly, substantially inducing, promoting or enhancing DR5 biological activity or activation. Optionally, an "agonist DR5 antibody" is an antibody which has activity at least comparable to the ligand for DR5, known as Apo-2 ligand (TRAIL), or is capable of activating DR5 receptor which results in an activation of one more intracellular signaling pathway which may include activation of caspase 3, caspase 8, caspase 10 or FADD.

The terms "antagonist" and "antagonistic" when used herein refer to or describe a molecule which is capable of, directly or indirectly, substantially counteracting, reducing or inhibiting DR5 biological activity of DR5 activation. Optionally, an antagonist is a molecule which neutralizes the biological activity resulting from DR5 activation or formation of a complex between DR5 and its ligand, such as Apo-2 ligand.

The term "antibody" is used in the broadest sense and specifically covers intact monoclonal antibodies, polyclonal antibodies, multivalent antibodies (e.g. bispecific antibodies) formed from at least two intact antibodies, and antibody fragments so long as they exhibit the desired biological activity.

"Native antibodies" and "native immunoglobulins" are usually heterotetrameric glycoproteins of about 150,000 daltons, composed of two identical light (L) chains and identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$).

As used herein, an "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

With respect to antibodies of the invention, the term "immunologically specific" or "specifically binds" refers to antibodies that bind to one or more epitopes of a protein of interest (e.g., DR5/TRAIL R2), but which do not substantially recognize and bind other molecules in a sample containing a mixed population of antigenic biological molecules.

The "epitope DR5-01" and the "epitope DR5-05" are the regions in the extracellular domain of DR5 to which the DR5-01 and the DR5-05 antibodies bind respectively.

The term "bispecific antibody" as used herein refers to an antibody comprising two antigen-binding sites, a first binding site having affinity for a first antigen or epitope and a second binding site having binding affinity for a second antigen or epitope distinct from the first.

"Bispecific antibodies" or "biparatopic antibodies" are single, divalent antibodies which have two different specific antigen binding sites. According to this invention, these antibodies have two different binding sites, each one directed against a specific and different epitope on the DR5 molecule. This definition also encompasses the fragments of a bispecific or biparatopic antibody that comprise both binding site and wherein each of these binding sites has the capability of binding to the corresponding epitope on DR5. Such a fragment may be for example a F(ab')$_2$ antibody fragment.

The term "bivalent, bispecific antibody" as used herein refers to an antibody as described above in which each of the two pairs of heavy chain and light chain (HC/LC) are specifically binding to a different epitope, i.e. the first heavy and light chains are specifically binding together to a first epitope, and, the second heavy and light chains are specifically binding together to a second epitope; such bivalent, bispecific antibodies are capable of specifically binding to two different epitopes, at the same time or not.

According to the invention, the ratio of a desired bivalent, bispecific antibody compared to undesired side products can be improved by the replacement of certain domains in only one pair of heavy chain and light chain (HC/LC). While the first of the two HC/LC pairs originates from an antibody specifically binding to a first epitope and is left essentially unchanged, the second of the two HC/LC pairs originates from an antibody specifically binding to a second epitope, and is altered by the following replacement:

Light chain: replacement of the variable light chain domain VL by the variable heavy chain domain VH of said antibody specifically binding to a second epitope, and the constant light chain domain CL by the constant heavy chain domain CH of said antibody specifically binding to a second epitope and Heavy chain: replacement of the variable heavy chain domain VH by the variable light chain domain VL of said antibody specifically binding to a second epitope, and the constant heavy chain domain CH by the constant light chain domain CL of said antibody specifically binding to a second epitope.

Engineered proteins, such as bi- or multivalent antibodies capable of binding two or more antigens or epitopes are known in the art. Such multivalent binding proteins can be generated using cell fusion, chemical conjugation, or recombinant DNA techniques.

In one approach bispecific antibodies that are very similar to natural antibodies have been produced using the quadroma technology, (Milstein C. et al., *Nature*. 1983; 305:537-40) based on the somatic fusion of two different hybridoma cell lines expressing murine monoclonal antibodies with the desired specificities of the bispecific antibody. Because of the random pairing of two different antibody heavy and light chains within the resulting hybrid-hybridoma (or quadroma) cell line, up to ten different antibodies species are generated of which only one is the desired, functional bispecific antibody. Due to the presence of mispaired byproducts, and significantly reduced production yields, means sophisticated purification procedures are required, (Morrison S. L., *Nature Biotech*. 2007; 25:1233-1234). In general the same problem of mispaired byproducts remains if recombinant expression techniques are used.

An approach to circumvent the problem of mispaired byproducts, which is known as "knobs-into-holes", aims at forcing the pairing of two different antibody heavy chains by introducing mutations into the CH3 domains to modify the contact interface. On one chain bulky amino acids are replaced by amino acids with short side chains to create a "hole". Conversely, amino acids with large side chains are introduced into the other CH3 domain, to create a "knob". By coexpressing these two heavy chains (and two identical light chains, which have to be appropriate for both heavy chains), high yields of heterodimer formation ("knob-hole") versus homodimer formation ("hole-hole" or "knob-knob") may be observed, (Ridgway, J B et al., *Protein Eng*. 1996; 9:617-621; and WO 96/027011).

"Antibody fragments" comprise a portion of an intact antibody, preferably the antigen binding or variable region of the intact antibody. A suitable "antibody fragment" is a fragment of antibody that has the capability to bind to the DR5 epitope and initiate the apoptosis pathway.

Examples of antibody fragments include Fab, Fab', F(ab')$_2$, and Fv fragments; diabodies; linear antibodies, (Zapata et al., *Protein Eng*. 1995; 8(10):1057-1062); single-chain antibody molecules; and multivalent antibodies formed from antibody fragments.

An "intact" antibody is one which comprises an antigen-binding variable region as well as a light chain constant domain (CL) and heavy chain constant domains, CH1, CH2 and CH3. Papain digestion of antibodies produces two identical antigen-binding fragments, called "Fab" fragments, each comprising a single antigen-binding site and a CL and a CH1 region, and a residual Fc fragment. Pepsin treatment yields an "F(ab')$_2$" fragment that has two antigen-binding sites and is still capable of cross-linking antigen.

"Fv" is the minimum antibody fragment which contains a complete antigen-recognition and antigen-binding site. This region consists of a dimer of one heavy chain and one light chain variable domain in tight, non-covalent association. It is in this configuration that the three hypervariable regions (CDRs) of each variable domain interact to define an antigen-binding site on the surface of the VH-VL dimer. Collectively, the six hypervariable regions or CDRs confer antigen-binding specificity to the antibody.

The "Fab" fragment also contains the constant domain of the light chain and the first constant domain (CH1) of the heavy chain and has one antigen-binding site only.

"Fab" fragments differ from Fab fragments by the addition of a few residues at the carboxy terminus of the heavy chain CH1 domain including one or more cysteines from the antibody hinge region.

F(ab')$_2$ antibody fragments originally were produced as pairs of Fab' fragments which have hinge cysteines between them. Other chemical couplings of antibody fragments are also known (Hermanson et al., *Bioconjugate Techniques*, Academic Press, 1996, U.S. Pat. No. 4,342,566).

"Single-chain Fv" or "scFv" antibody fragments comprise the VH and the VL domains of an antibody wherein these domains are present in a single polypeptide chain. Preferably, the scFv comprises a polypeptide linker between the VH and VL domains which enables the scFv to form the desired structure for antigen binding.

The terms "polypeptide", "peptide" and "protein" are used interchangeably herein to refer to a polymer of amino acid residues. The terms apply to naturally occurring amino acid polymers as well as to amino acid polymers in which one or more amino acid residues is an artificial chemical analogue of a corresponding naturally occurring amino acid. The term also includes variants on the traditional peptide linkage joining the amino acids making up the polypeptide. Preferred "peptides", "polypeptides", and "proteins" are chains of amino acids whose carbons are linked through peptide bonds.

The terminal amino acid at one end of the chain (amino terminal) therefore has a free amino group, while the terminal amino acid at the other end of the chain (carboxy terminal) has a free carboxyl group. As used herein, the term "amino terminus" (abbreviated N-terminus) refers to the free α-amino group on an amino acid at the amino terminal of a peptide or to the α-amino group (amino group when participating in a peptide bond) of an amino acid at any other location within the peptide. Similarly, the term "carboxy terminus" refers to the free carboxyl group on the carboxy terminus of a peptide or the carboxyl group of an amino acid at any other location within the peptide. Peptides also include essentially any polyamino acid including, but not limited to peptide mimetics such as amino acids joined by ether as opposed to an amine bond.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated, in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies, (Kabat et al., *NIH Publ.* 1991; No. 91-3242, Vol. 1, 647-669). The constant domains are not involved directly in binding an antibody to an antigen, but exhibit various effectors functions, such as participation of the antibody in antibody-dependent cellular toxicity.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA*, 81:6851-6855 (1984)).

Other preferred forms of "chimeric antibodies" encompassed by the present invention are those in which the constant region has been modified or changed from that of the original antibody to generate the properties according to the invention, especially in regard to C1q binding and/or Fc receptor (FcR) binding.

Such chimeric antibodies are also referred to as "class-switched antibodies". Chimeric antibodies are the product of expressed immunoglobulin genes comprising DNA segments encoding immunoglobulin variable regions and DNA segments encoding immunoglobulin constant regions. Methods for producing chimeric antibodies involve conventional recombinant DNA and gene transfection techniques are well known in the art. See, e.g., Morrison, S. L et al., *Proc. Natl. Acad. Sci. USA* 1984; 81:6851-6855; U.S. Pat. No. 5,202,238 and U.S. Pat. No. 5,204,244. WO 2006/093794 relates to heterodimeric protein binding compositions. WO 99/37791 describes multipurpose antibody derivatives. Morrison et al., *the J. Immunolog.* 1998; 160: 2802-2808 refers to the influence of variable region domain exchange on the functional properties of IgG.

"Humanized" forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementarity-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues.

In a preferred embodiment, a murine CDR is grafted into the framework region of a human antibody to prepare the "humanized antibody". See, e.g., Riechmann, L. et al., *Nature*. 1988; 332: 323-327; and Neuberger, M S et al., *Nature*. 1985; 314: 268-270. Particularly preferred CDRs correspond to those representing sequences recognizing the antigens noted above for chimeric antibodies. Other forms of "humanized antibodies" encompassed by the present invention are those in which the constant region has been additionally modified or changed from that of the original antibody to generate the properties according to the invention, especially in regard to C1q binding and/or Fc receptor (FcR) binding.

Furthermore, humanized antibodies may comprise residues which are found neither in the recipient antibody nor in the imported CDR or framework sequences. These modifications are made to further refine and maximize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., *Nature*. 1986; 321:522-525; Reichmann et al., *Nature*. 1988; 332:323-329; and Presta et al., *Curr. Op. Struct. Biol.* 1992; 2:593-596.

Immune effector functions which have been shown to contribute to antibody-mediated cytotoxicity include antibody-dependent cell-mediated cytotoxicity (ADCC), antibody-dependent cell-mediated phagocytosis (ADCP), and complement-dependent cytotoxicity (CDC).

Cytotoxicity may also be mediated via antiproliferative effects. The mechanism of antibody modulation of tumor cell proliferation is poorly understood. However, advances in understanding the interactions of antibodies with Fcg receptors (FcgR) on immune effector cells have allowed the engineering of antibodies with significantly improved effector function.

The mechanism of action of MAbs is complex and appears to vary for different MAbs. There are multiple mechanisms by which MAbs cause target cell death. These include apoptosis, CDC, ADCC and inhibition of signal transduction.

Effector functions such as CDC and ADCC are effector functions that may be important for the clinical efficacy of MAbs. All of these effector functions are mediated by the antibody Fc region and let authors to attempt amino acid modifications with more or less success. Glycosylation, especially fucosylation of the Fc region have a dramatic influence on the efficacy of an antibody. This let the authors to modify the conditions of production of the antibodies in the CHO cells in order to change the glycosylation profile in an attempt here again to improve some effector functions, with more or less success one again.

Previous research has shown that a polymorphism of the FcgRIIIa gene encodes for either a phenylalanine (F) or a valine (V) at amino acid 158. Expression of the valine isoform correlates with increased affinity and binding to MAbs (Rowland A J, et al. 1993. Cancer Immunol Immunother. 37(3):195-202; Sapra P, Allen T M. 2002. Cancer Res 62: 7190-4; Mølhøj M, et al. 2007. Mol Immunol. 44(8):1935-43). Some clinical studies have supported this finding, with greater clinical response to rituximab in patients with non-Hodgkin's lymphoma who display the V/V polymorphism (Bargou R, et al. 2008. Science. 321: 974-7; Bruenke J, 2005. Br J Haematol. 130(2):218-28; Cartron G, Blood. 2002 Feb. 1; 99(3):754-8; Hekman A, et al. 1991. Cancer Immunol Immunother 32:364-72).

WO1999051642 describes a variant human IgG Fc region comprising an amino acid substitution at positions 270 or 329, or at two or more of positions 270, 322, 329, and 331. These modifications aim at increasing the CDC and ADCC effector functions "Treatment" or "therapy" refer to both therapeutic treatment and prophylactic or preventative measures.

"Mammal" for purposes of treatment or therapy refers to any animal classified as a mammal, including humans, domestic and farm animals, and zoo, sports, or pet animals, such as dogs, horses, cats, cows, etc. Preferably, the mammal is human.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, small-cell lung cancer, non-small cell lung cancer, gastrointestinal cancer, renal cancer, pancreatic cancer, glioblastoma, cervical cancer, ovarian cancer, liver cancer, bladder cancer, hepatoma, breast cancer, colon cancer, colorectal cancer, endometrial carcinoma, salivary gland carcinoma, kidney cancer, prostate cancer, vulval cancer, thyroid cancer, hepatic carcinoma and various types of head and neck cancer.

The term "nucleic acid" or "oligonucleotide" or grammatical equivalents herein refer to at least two nucleotides covalent linked together. A nucleic acid of the present invention is preferably single-stranded or double stranded and will generally contain phosphodiester bonds.

Amino acid sequence "variants" (or mutants) of the antibody are prepared by introducing appropriate nucleotide changes into the antibody DNA, or by nucleotide synthesis. Such modifications can be performed, however, only in a very limited range, e.g. as described above. For example, the modifications do not alter the above mentioned antibody characteristics such as the IgG isotype and antigen binding, but may improve the yield of the recombinant production, protein stability or facilitate the purification.

DETAILED DESCRIPTION OF THE INVENTION

The CDR sequences may be defined in accordance with IMGT®, Kabat® or the Common numbering system which retain the common sequence between IMGT® and Kabat®.

The CDRs for the anti-DR5 antibodies mDR5-01 a chimeric antibody with murine VH and VL and human Fc) and HzDR5-01 (a humanized antibody with murine CDRs and human FR with or without back mutation and Fc optimized or not) of the invention comprises the following CDRs:

TABLE 1

| | SEQ ID NO: | Sequence IMGT ® | SEQ ID NO: | Sequence Kabat ® | SEQ ID NO: | Sequence (Common numbering system) |
|---|---|---|---|---|---|---|
| | | | VH mDR5-01 - VH HzDR5-01 | | | |
| CDR1 | 13 | GFNIKDTF | 22 | DTFIH | 32 | KDTF |
| CDR2 | 14 | IDPANGNT | 23 | RIDPANGNTKYDPKFQG | 14 | IDPANGNT |
| CDR3 | 15 | VRGLYTYYFDY | 24 | GLYTYYFDY | 24 | GLYTYYFDY |

TABLE 1-continued

| SEQ ID NO: | Sequence IMGT® | SEQ ID NO: | Sequence Kabat® | SEQ ID NO: | Sequence (Common numbering system) |
|---|---|---|---|---|---|
| | | VL mDR5-01 - VH HzDR5-01 | | | |
| CDR1 | 16 QSISNN | 25 | RASQSISNNLH | 16 | QSISNN |
| CDR2 | FAS | 26 | FASQSIS | | FAS |
| CDR3 | 17 QQGNSWPYT | 17 | QQGNSWPYT | 17 | QQGNSWPYT |

The CDRs for the anti-DR5 antibodies mDR5-05 and HzDR5-05 of the invention comprises the following CDRs:

TABLE 2

| SEQ ID NO: | Sequence IMGT® | SEQ ID NO: | Sequence Kabat® | SEQ ID NO: | Sequence (Common numbering system) |
|---|---|---|---|---|---|
| | | VH mDR5-05 - VH HzDR5-05 | | | |
| CDR1 | 18 GFNIKDTH | 27 | DTHIH | 33 | KDTH |
| CDR2 | 14 IDPANGNT | 28 | RIDPANGNTEYDPKFQG | 14 | IDPANGNT |
| CDR3 | 19 ARWGTNVYFAY | 29 | WGTNVYFAY | 29 | WGTNVYFAY |
| | | VL mDR5-05 - VH HzDR5-05 | | | |
| CDR1 | 20 SSVSY | 30 | SASSSVSYMY | 20 | SSVSY |
| CDR2 | RTS | 31 | RTSNLAS | | RTS |
| CDR3 | 21 QQYHSYPPT | 21 | QQYHSYPPT | 21 | QQYHSYPPT |

By definition, these CDRs include variant CDRs, by deletion, substitution or addition of one or more amino acid(s), which variant keeps the specificity of the original CDR. The common numbering system provides for a CDR definition having the shortest amino acid sequences or the minimal CDR definition.

mDR5-01, mDR5-05, HzDR5-01 and HzDR5-05 have the VH and VL amino acid sequences and nucleic acid sequences are depicted on the following tables:

TABLE 3

| | Amino acid sequence VH | Amino acid sequence VL |
|---|---|---|
| mDR5-01 | SEQ ID NO: 4 | SEQ ID NO: 2 |
| mDR5-05 | SEQ ID NO: 8 | SEQ ID NO: 6 |
| HzDR5-01 | SEQ ID NO: 35 | SEQ ID NO: 37 |
| HzDR5-05 | SEQ ID NO: 39 | SEQ ID NO: 41 |

TABLE 4

| | Nucleic acid sequence VH | Nucleic acid sequence VL |
|---|---|---|
| mDR5-01 | SEQ ID NO: 3 | SEQ ID NO: 1 |
| mDR5-05 | SEQ ID NO: 7 | SEQ ID NO: 5 |
| HzDR5-01 | SEQ ID NO: 34 | SEQ ID NO: 36 |
| HzDR5-05 | SEQ ID NO: 38 | SEQ ID NO: 40 |

DR5-01 and DR5-05 have the CH and CL amino acid sequences and nucleic acid sequences are depicted on the following tables:

TABLE 5

| | CH | CL |
|---|---|---|
| Amino acid sequence | SEQ ID NO: 10 | SEQ ID NO: 12 |
| Nucleic acid sequence | SEQ ID NO: 9 | SEQ ID NO: 11 |

In an embodiment, the polypeptide comprises one or two binding domains comprising a pair of VH and VL chains wherein the VH chain contains a CDR1 of sequence SEQ ID NO: 13, a CDR2 of sequence SEQ ID NO: 14, a CDR3 of sequence SEQ ID NO: 15; and the VL chain contains a CDR1 of sequence SEQ ID NO: 16, a CDR2 of sequence FAS, a CDR3 of sequence SEQ ID NO: 17. This polypeptide binds specifically to a first epitope on the DR5 receptor. In an embodiment, the polypeptide comprises two such binding domains.

In an embodiment, the polypeptide comprises one or two binding domains comprising a pair of VH and VL chains wherein the VH chain contains a CDR1 of sequence SEQ ID NO: 22, a CDR2 of sequence SEQ ID NO: 23, a CDR3 of sequence SEQ ID NO: 24; and the VL chain contains a CDR1 of sequence SEQ ID NO: 25, a CDR2 of sequence SEQ ID NO: 26, a CDR3 of sequence SEQ ID NO: 17. This polypeptide binds specifically to a first epitope on the DR5 receptor. In an embodiment, the polypeptide comprises two such binding domains.

In an embodiment, the polypeptide comprises one or two binding domains comprising a pair of VH and VL chains wherein the VH chain contains a CDR1 of sequence SEQ ID NO: 32, a CDR2 of sequence SEQ ID NO: 14, a CDR3 of sequence SEQ ID NO: 24; and the VL chain contains a CDR1 of sequence SEQ ID NO: 16, a CDR2 of sequence FAS, a CDR3 of sequence SEQ ID NO: 17. This polypeptide binds specifically to a first epitope on the DR5 receptor. In an embodiment, the polypeptide comprises two such binding domains.

In another embodiment, the polypeptide comprises a pair of VH and VL chains wherein the VH chain contains a CDR1 of sequence SEQ ID NO: 18, a CDR2 of sequence SEQ ID NO: 14, a CDR3 of sequence SEQ ID NO: 19; and the VL chain contains a CDR1 of sequence SEQ ID NO: 20, a CDR2 of sequence RTS, a CDR3 of sequence SEQ ID NO: 21. This polypeptide binds specifically to a second and different epitope on the DR5 receptor. In an embodiment, the polypeptide comprises two such binding domains.

In another embodiment, the polypeptide comprises a pair of VH and VL chains wherein the VH chain contains a CDR1 of sequence SEQ ID NO: 27, a CDR2 of sequence SEQ ID NO: 28, a CDR3 of sequence SEQ ID NO: 29; and the VL chain contains a CDR1 of sequence SEQ ID NO: 30, a CDR2 of sequence SEQ ID NO: 31, a CDR3 of sequence SEQ ID NO: 21. This polypeptide binds specifically to a second and different epitope on the DR5 receptor. In an embodiment, the polypeptide comprises two such binding domains.

In another embodiment, the polypeptide comprises a pair of VH and VL chains wherein the VH chain contains a CDR1 of sequence SEQ ID NO: 33, a CDR2 of sequence SEQ ID NO: 14, a CDR3 of sequence SEQ ID NO: 29; and the VL chain contains a CDR1 of sequence SEQ ID NO: 20, a CDR2 of sequence RTS, a CDR3 of sequence SEQ ID NO: 21. This polypeptide binds specifically to a second and different epitope on the DR5 receptor. In an embodiment, the polypeptide comprises two such binding domains.

In another embodiment, the anti-DR5 polypeptide comprises two binding domains and these two binding domains are each specific of a different epitope on the DR5 receptor. These binding domains comprise a specific set of 3 CDRs on the VH and VL as disclosed and provided therein and may be identical or slightly different in the framework regions.

The anti-DR5 polypeptide may be in particular a F(ab')$_2$, Fab, Fv, a divalent single-chain variable fragment (scFv), an antibody, preferably a monoclonal antibody, fragment, nanobody, multimeric scFv.

In this embodiment, the anti-DR5 polypeptide, preferably antibody, is bispecific or biparatopic and comprises:
  a first binding domain comprising a pair of VH and VL chains wherein the VH chain contains a CDR1 comprising or consisting of sequence SEQ ID NO: 13, a CDR2 comprising or consisting of sequence SEQ ID NO: 14, a CDR3 comprising or consisting of sequence SEQ ID NO: 15; and the VL chain contains a CDR1 comprising or consisting of sequence SEQ ID NO: 16, a CDR2 comprising or consisting of sequence FAS, a CDR3 comprising or consisting of sequence SEQ ID NO: 17, and
  a second binding domain comprising a pair of VH and VL chains wherein the VH chain contains a CDR1 comprising or consisting of sequence SEQ ID NO: 18, a CDR2 comprising or consisting of sequence SEQ ID NO: 14, a CDR3 comprising or consisting of sequence SEQ ID NO: 19; and the VL chain contains a CDR1 comprising or consisting of sequence SEQ ID NO: 20,
  a CDR2 comprising or consisting of sequence RTS, a CDR3 comprising or consisting of sequence SEQ ID NO: 21.

In an embodiment, the anti-DR5 polypeptide, preferably antibody, is bispecific or biparatopic and comprises:
  a first binding domain comprising a pair of VH and VL chains wherein the VH chain contains a CDR1 comprising or consisting of sequence SEQ ID NO:22, a CDR2 comprising or consisting of sequence SEQ ID NO: 23, a CDR3 comprising or consisting of sequence SEQ ID NO: 24; and the VL chain contains a CDR1 comprising or consisting of sequence SEQ ID NO: 25, a CDR2 comprising or consisting of sequence SEQ ID NO: 26, a CDR3 comprising or consisting of sequence SEQ ID NO: 17, and
  a second binding domain comprising a pair of VH and VL chains wherein the VH chain contains a CDR1 comprising or consisting of sequence SEQ ID NO: 27, a CDR2 comprising or consisting of sequence SEQ ID NO: 28, a CDR3 comprising or consisting of sequence SEQ ID NO: 29; and the VL chain contains a CDR1 comprising or consisting of sequence SEQ ID NO: 30, a CDR2 comprising or consisting of sequence SEQ ID NO: 31, a CDR3 comprising or consisting of sequence SEQ ID NO: 21.

In an embodiment, the anti-DR5 polypeptide, preferably antibody, is bispecific or biparatopic and comprises:
  a first binding domain comprising a pair of VH and VL chains wherein the VH chain contains a CDR1 comprising or consisting of sequence SEQ ID NO: 32, a CDR2 comprising or consisting of sequence SEQ ID NO: 14, a CDR3 comprising or consisting of sequence SEQ ID NO: 24; and the VL chain contains a CDR1 comprising or consisting of sequence SEQ ID NO: 16, a CDR2 comprising or consisting of sequence FAS, a CDR3 comprising or consisting of sequence SEQ ID NO: 17, and
  a second binding domain comprising a pair of VH and VL chains wherein the VH chain contains a CDR1 comprising or consisting of sequence SEQ ID NO: 33, a CDR2 comprising or consisting of sequence SEQ ID NO: 14, a CDR3 comprising or consisting of sequence SEQ ID NO: 29; and the VL chain contains a CDR1 comprising or consisting of sequence SEQ ID NO: 20, a CDR2 comprising or consisting of sequence RTS, a CDR3 comprising or consisting of sequence SEQ ID NO: 21.

This bispecific or biparatopic anti-DR5 polypeptide or antibody comprises the two different domains of the invention and may bind specifically to either one of the two different epitopes or to both different epitopes at the same time.

In some embodiments, the anti-DR5 polypeptides preferably antibody of the invention comprises:
  one or more of amino acid sequence pairs SEQ ID NO: 2 and 4 (VL and VH from DR5-01) and SEQ ID NO: 6 and 8 (VH and VL from DR5-05),
  the pair of amino acid sequences SEQ ID NO: 2 and 4, (VL and VH from DR5-01)
  the pair of amino acid sequences SEQ ID NO: 6 and 8, (VL and VH from DR5-05) or
  both amino acid sequence pairs SEQ ID NO: 2 and 4 (VL and VH from DR5-01) and SEQ ID NO: 6 and 8 (VL and VH from DR5-05);
  one or more of amino acid sequence pairs SEQ ID NO: 35 and 37 (VH and VL from HzDR5-01) and SEQ ID NO: 39 and 41 (VH and VL from HzDR5-05), the pair of amino acid sequences SEQ ID NO: 35 and 37, (VH and VL from HzDR5-01)

the pair of amino acid sequences SEQ ID NO: 39 and 41, (VH and VL from HzDR5-05) or both amino acid sequence pairs SEQ ID NO: 35 and 37 (VH and VL from HzDR5-01) and SEQ ID NO: 39 and 41 (VL and VH from HzDR5-05).

In some embodiments, the anti-DR5 polypeptide, preferably antibody of the invention comprises:

two of each amino acid sequences SEQ ID NO: 4, 10, 2 and 12 (e.g. the whole or intact DR5-01 antibody)

amino acid sequences SEQ ID NO: 4, 10, 2 and 12 (single chain Fv based on DR5-01);

two of each amino acid sequences SEQ ID NO: 8, 10, 6 and 12 (e.g. the whole or intact DR5-05 antibody)

amino acid sequences SEQ ID NO: 8, 10, 6 and 12 (single chain Fv based on DR5-05);

amino acid sequences SEQ ID NO: 4, 8, 2, 6, 10 and 12 (bispecific antibody), especially the bispecific antibody comprises SEQ ID NO: 4, 8, 2, 6 (one of each) and 10, 12 (two of each);

amino acid sequences SEQ ID NO: 2 and 12 (light chain);

amino acid sequences SEQ ID NO: 6 and 12 (light chain);

amino acid sequences SEQ ID NO: 4 and 10 (heavy chain);

amino acid sequences SEQ ID NO: 8 and 10 (heavy chain).

two of each amino acid sequences SEQ ID NO: 35, 10, 37 and 12 (e.g. the whole or intact HzDR5-01 antibody)

amino acid sequences SEQ ID NO: 35, 10, 37 and 12 (single chain Fv based on HzDR5-01);

two of each amino acid sequences SEQ ID NO: 39, 10, 41 and 12 (e.g. the whole or intact HzDR5-05 antibody)

amino acid sequences SEQ ID NO: 39, 10, 41 and 12 (single chain Fv based on HzDR5-05);

amino acid sequences SEQ ID NO: 35, 39, 37, 41, 10 and 12 (bispecific antibody), especially the bispecific antibody comprises SEQ ID NO: 35, 39, 37, 41 (one of each) and 10, 12 (two of each);

amino acid sequences SEQ ID NO: 37 and 12 (light chain);

amino acid sequences SEQ ID NO: 41 and 12 (light chain);

amino acid sequences SEQ ID NO: 35 and 10 (heavy chain);

amino acid sequences SEQ ID NO: 39 and 10 (heavy chain).

The anti-DR5 polypeptides, preferably antibodies, of the invention may be fully murine, say they comprise amino acid sequences that match with the amino acid sequence of the maternal or original murine antibody. The polypeptides of the invention may also be chimeric or humanized, say they can comprise human-derived amino acid sequences. Specifically, the polypeptide may comprise framework regions and/or constant regions of a human-derived antibody.

Another object of the invention is a composition or pharmaceutical composition comprising one, two or more polypeptides according to the invention, as disclosed above and provided herein, and a pharmaceutically acceptable carrier, diluent or excipient. Embodiments of these compositions are defined by using the CDRs definitions according to IMGT®. However, the invention encompasses and relates also to the equivalent or alternative compositions wherein the IMGT® numbering is replaced either by the Kabat® numbering or the Common numbering system, using the sequences indicated supra. Therefore, in the following embodiments of a composition, other embodiments are part of the invention in which one replaces the CDRs defined with IMGT® numbering, by the Kabat® numbering, in accordance with the table supra. Also, in the following embodiments of a composition, other embodiments are part of the invention in which one replaces the CDRs defined with IMGT® numbering, by the Common numbering system, in accordance with the table supra.

In a first embodiment, the composition comprises a polypeptide, preferably antibody, having one or two binding domain(s) comprising a pair of VH and VL chains wherein the VH chain contains a CDR1 of sequence SEQ ID NO: 13, a CDR2 of sequence SEQ ID NO: 14, a CDR3 of sequence SEQ ID NO: 15; and the VL chain contains a CDR1 of sequence SEQ ID NO: 16, a CDR2 of sequence FAS, a CDR3 of sequence SEQ ID NO: 17. In a second embodiment, the composition comprises a polypeptide, preferably antibody, having one or two binding domain(s) comprising a pair of VH and VL chains wherein the VH chain contains a CDR1 of sequence SEQ ID NO: 18, a CDR2 of sequence SEQ ID NO: 14, a CDR3 of sequence SEQ ID NO: 19; and the VL chain contains a CDR1 of sequence SEQ ID NO: 20, a CDR2 of sequence RTS, a CDR3 of sequence SEQ ID NO: 21. In a third embodiment, the composition comprises these two polypeptides or antibodies in mixture. As an alternative, one may replace hereinabove the definition of the CDRs by those according to Kabat® or Common numbering System as per Tables 1 and 2.

In another embodiment, the composition comprises a anti-DR5 bispecific polypeptide, preferably antibody, comprising a first binding domain comprising a pair of VH and VL chains wherein the VH chain contains a CDR1 of sequence SEQ ID NO: 13, a CDR2 of sequence SEQ ID NO: 14, a CDR3 of sequence SEQ ID NO: 15; and the VL chain contains a CDR1 of sequence SEQ ID NO: 16, a CDR2 of sequence FAS, a CDR3 of sequence SEQ ID NO: 17, and a second binding domain comprising a pair of VH and VL chains wherein the VH chain contains a CDR1 of sequence SEQ ID NO: 18, a CDR2 of sequence SEQ ID NO: 14, a CDR3 of sequence SEQ ID NO: 19; and the VL chain contains a CDR1 of sequence SEQ ID NO: 20, a CDR2 of sequence RTS, a CDR3 of sequence SEQ ID NO: 21. As an alternative, one may replace hereinabove the definition of the CDRs by those according to Kabat® or Common numbering System as per Tables 1 and 2.

In an embodiment, the composition comprises an anti-DR5 polypeptide, preferably antibody, comprising the amino acid sequence pair SEQ ID NO: 2 and 4, an anti-DR5 polypeptide, preferably antibody, comprising the amino acid sequence pair SEQ ID NO: 6 and 8, and a pharmaceutically carrier, diluents or excipient. In an embodiment, the composition comprises an anti-DR5 polypeptide, preferably antibody, comprising the amino acid sequence pair SEQ ID NO: 35 and 37, an anti-DR5 polypeptide, preferably antibody, comprising the amino acid sequence pair SEQ ID NO: 39 and 41, and a pharmaceutically carrier, diluents or excipient.

The present invention also relates to these compositions comprising at least two polypeptides, preferably antibodies, for a simultaneous, separate or sequential administration to a mammal, including man.

A particular object is a composition comprising a bispecific anti-DR5 antibody comprising an amino acid sequence pair SEQ ID NO: 2 and 4 and an amino acid sequence pair SEQ ID NO: 6 and 8, or comprising an amino acid sequence pair SEQ ID NO: 35 and 37 and an amino acid sequence pair SEQ ID NO: 39 and 41, and a pharmaceutically acceptable carrier.

An object of the invention is especially a composition comprising at least one or two polypeptides binding specifically a DR5 receptor, wherein the at least one or two polypeptides comprise two immunoglobulin binding domains comprising:

a first binding domain comprising a pair of VH and VL chains wherein the VH chain contains a CDR1 of sequence SEQ ID NO: 13, a CDR2 of sequence SEQ ID NO: 14 CDR1, a CDR3 of sequence SEQ ID NO: 15; and the VL chain contains a CDR1 of sequence SEQ ID NO: 16, a CDR2 of sequence FAS, a CDR3 of sequence SEQ ID NO: 17, and a second binding domain comprising a pair of VH and VL chains wherein the VH chain contains a CDR1 of sequence SEQ ID NO: 18, a CDR2 of sequence SEQ ID NO: 14, a CDR3 of sequence SEQ ID NO: 19; and the VL chain contains a CDR1 of sequence SEQ ID NO: 20, a CDR2 of sequence RTS, a CDR3 of sequence SEQ ID NO: 21, wherein the at least one polypeptide comprises both immunoglobulin binding domains, or the at least two polypeptides comprise a first polypeptide comprising the first binding domain and a second polypeptide comprising the second binding domain for a simultaneous, separate or sequential administration to a mammal, including man, and a pharmaceutically carrier, diluent or excipient. As an alternative, one may replace hereinabove the definition of the CDRs by those according to Kabat® or Common numbering System as per Tables 1 and 2.

In some embodiments, the composition of the invention comprises an anti-DR5 polypeptide, preferably antibody comprising:

two of each amino acid sequences SEQ ID NO: 4, 10, 2 and 12 (e.g. the whole or intact DR5-01 antibody)

amino acid sequences SEQ ID NO: 4, 10, 2 and 12 (single chain Fv based on DR5-01);

two of each amino acid sequences SEQ ID NO: 8, 10, 6 and 12 (e.g. the whole or intact DR5-05 antibody)

amino acid sequences SEQ ID NO: 8, 10, 6 and 12 (single chain Fv based on DR5-05);

amino acid sequences SEQ ID NO: 4, 8, 2, 6, 10 and 12 (bispecific antibody), especially the bispecific antibody comprises SEQ ID NO: 4, 8, 2, 6 (one of each) and 10, 12 (two of each);

amino acid sequences SEQ ID NO: 2 and 12 (light chain);

amino acid sequences SEQ ID NO: 6 and 12 (light chain);

amino acid sequences SEQ ID NO: 4 and 10 (heavy chain);

amino acid sequences SEQ ID NO: 8 and 10 (heavy chain);

two of each amino acid sequences SEQ ID NO: 35, 10, 37 and 12 (e.g. the whole or intact HzDR5-01 antibody)

amino acid sequences SEQ ID NO: 35, 10, 37 and 12 (single chain Fv based on HzDR5-01);

two of each amino acid sequences SEQ ID NO: 39, 10, 41 and 12 (e.g. the whole or intact HzDR5-05 antibody)

amino acid sequences SEQ ID NO: 39, 10, 41 and 12 (single chain Fv based on HzDR5-05);

amino acid sequences SEQ ID NO: 35, 39, 37, 41, 10 and 12 (bispecific antibody), especially the bispecific antibody comprises SEQ ID NO: 35, 39, 37, 41 (one of each) and 10, 12 (two of each);

amino acid sequences SEQ ID NO: 37 and 12 (light chain);

amino acid sequences SEQ ID NO: 41 and 12 (light chain);

amino acid sequences SEQ ID NO: 35 and 10 (heavy chain);

amino acid sequences SEQ ID NO: 39 and 10 (heavy chain).

These compositions may comprise at least one additional polypeptide or antibody directed against another target and/or at least one chemotherapeutic drug (such as small molecule), for a simultaneous, separate or sequential administration with polypeptide(s) or antibody(ies) of the invention, to a mammal, including man. As additional active principle, one may cite doxorubicine, gemcitabine, camptothecin, paclitaxel. The composition may comprise two polypeptides, or antibodies or fragments thereof, both having the capability to bind to DR5, modified to comprise a variant human optimized IgG Fc region, preferably IgG1 Fc region, wherein this variant region comprises an amino acid substitution to modulate PDCC, ADCC and/or CDC. In particular, two polypeptides, or antibodies or fragments thereof, have the capability to bind to DR5, and conjugate to cellular cytotoxic components (ADC)z.

The compositions or pharmaceutical compositions according to the invention are intended for use as a medicament, especially to induce apoptosis of a tumor cell. The compositions or pharmaceutical compositions according to the invention are intended for use as a medicament, especially to treat cancer, preferably a solid cancer.

The isolated nucleic acid sequences disclosed and provided herein are also object of the invention.

Thus the invention also relates to an isolated nucleotide sequence comprising the following nucleotide sequences SEQ ID NO: 1, 3, 5, or 7 or combinations of nucleotide sequences linked together; SEQ ID NO: 9 and 7, or 9 and 3, SEQ ID NO: 11 and 1, or 11 and 5. The invention also relates to an isolated nucleotide sequence comprising the following nucleotide sequences SEQ ID NO: 34, 36, 38 or 40 or combinations of nucleotide sequences linked together; SEQ ID NO: 9 and 34, or 9 and 38, SEQ ID NO: 11 and 36, or 11 and 40.

The present invention also relates to a method of prevention and/or treatment of a disease wherein inducing apoptosis of some cell is beneficial to the mammal, in particular the human in terms of prevention or treatment (therapeutic or prophylactic). Those diseases are in particular cancer, especially one of those listed in the Definitions supra, autoimmune diseases, inflammatory conditions, viral infections and viral diseases. This method comprises the administration to a mammal, including human, of an effective amount of a composition as disclosed and provided herein. The method comprises the administration of the two polypeptides, preferably antibodies directed against the two different epitopes according to the invention, or of the bispecific polypeptide, preferably antibody directed against the two different epitopes according to the invention. Embodiments of these compositions are defined by using the CDRs definitions according to IMGT®. However, the invention encompasses and relates also to the equivalent or alternative methods wherein the IMGT® numbering is replaced either by the Kabat® numbering or the Common numbering system, using the sequences indicated supra. Therefore, in the following embodiments of a method, other embodiments are part of the invention in which one replaces the CDRs defined with IMGT® numbering, by the Kabat® numbering, in accordance with the table supra. Also, in the following embodiments of a method, other embodiments are part of the invention in which one replaces the CDRs defined with IMGT® numbering, by the Common numbering system, in accordance with the table supra.

In a first embodiment, the method comprises the administration of a composition which comprises a polypeptide, preferably antibody, having one or two binding domain(s) comprising a pair of VH and VL chains wherein the VH chain contains a CDR1 of sequence SEQ ID NO: 13, a CDR2 of sequence SEQ ID NO: 14, a CDR3 of sequence SEQ ID NO: 15; and the VL chain contains a CDR1 of sequence SEQ ID NO: 16, a CDR2 of sequence FAS, a CDR3 of sequence SEQ ID NO: 17. In a second embodiment, the method comprises the administration of a composition which comprises a polypeptide, preferably antibody, having one or two binding domain(s) comprising a pair of VH and VL chains wherein the VH chain contains a CDR1 of sequence SEQ ID NO: 18, a CDR2 of sequence SEQ ID NO: 14, a CDR3 of sequence SEQ ID NO: 19; and the VL chain contains a CDR1 of sequence SEQ ID NO: 20, a CDR2 of sequence RTS, a CDR3 of sequence SEQ ID NO: 21. In a third embodiment, the method comprises the administration of a composition which comprises these two polypeptides or antibodies in mixture, or of two compositions, one containing the first mentioned polypeptide or antibody, and the second comprising the second mentioned polypeptide or antibody. As an alternative, one may replace hereinabove the definition of the CDRs by those according to Kabat® or Common numbering System as per Tables 1 and 2.

In another embodiment, the method comprises the administration of a composition which comprises a bispecific polypeptide, preferably antibody, comprising a first binding domain comprising a pair of VH and VL chains wherein the VH chain contains a CDR1 of sequence SEQ ID NO: 13, a CDR2 of sequence SEQ ID NO: 14 CDR1, a CDR3 of sequence SEQ ID NO: 15; and the VL chain contains a CDR1 of sequence SEQ ID NO: 16, a CDR2 of sequence FAS, a CDR3 of sequence SEQ ID NO: 17, and a second binding domain comprising a pair of VH and VL chains wherein the VH chain contains a CDR1 of sequence SEQ ID NO: 18, a CDR2 of sequence SEQ ID NO: 14, a CDR3 of sequence SEQ ID NO: 19; and the VL chain contains a CDR1 of sequence SEQ ID NO: 20, a CDR2 of sequence RTS, a CDR3 of sequence SEQ ID NO: 21. As an alternative, one may replace hereinabove the definition of the CDRs by those according to Kabat® or Common numbering System as per Tables 1 and 2.

In an embodiment, the method provides for the administration of a composition which comprises an anti-DR5 polypeptide, preferably antibody, comprising the amino acid sequence pair SEQ ID NO: 2 and 4 and an anti-DR5 polypeptide, preferably antibody, comprising the amino acid sequence pair SEQ ID NO: 6 and 8, and a pharmaceutically carrier, diluent or excipient. In another embodiment, the method provides for the administration of two compositions, one which comprises an anti-DR5 polypeptide, preferably antibody, comprising the amino acid sequence pair SEQ ID NO: 2 and 4 and another which comprises an anti-DR5 polypeptide, preferably antibody, comprising the amino acid sequence pair SEQ ID NO: 6 and 8. In an embodiment, the method provides for the administration of a composition which comprises an anti-DR5 polypeptide, preferably antibody, comprising the amino acid sequence pair SEQ ID NO: 35 and 37 and an anti-DR5 polypeptide, preferably antibody, comprising the amino acid sequence pair SEQ ID NO: 39 and 41, and a pharmaceutically carrier, diluent or excipient.

In another embodiment, the method provides for the administration of two compositions, one which comprises an anti-DR5 polypeptide, preferably antibody, comprising the amino acid sequence pair SEQ ID NO: 35 and 37 and another which comprises an anti-DR5 polypeptide, preferably antibody, comprising the amino acid sequence pair SEQ ID NO: 39 and 41.

In another embodiment, the method provides for the administration of a composition comprising a bispecific anti-DR5 antibody comprising an amino acid sequence pair SEQ ID NO: 2 and 4 and an amino acid sequence pair SEQ ID NO: 6 and 8, and a pharmaceutically acceptable carrier. In another embodiment, the method provides for the administration of a composition comprising a bispecific anti-DR5 antibody comprising an amino acid sequence pair SEQ ID NO: 35 and 37 and an amino acid sequence pair SEQ ID NO: 39 and 41, and a pharmaceutically acceptable carrier.

In another embodiment, the method provides for the administration of a composition comprising the DR5-01 and the DR5-05 antibodies as disclosed and provided herein, or similar antibodies produced through genetic engineering as described herein, based on nucleotide sequences SEQ ID NO: 9, 3, 11 and 1, or SEQ ID NO: 9, 34, 11 and 36 for DR5-01, and SEQ ID NO: 9, 7, 11 and 5, or SEQ ID NO: 9, 38, 11 and 40 for DR5-05; use can be made of a composition comprising these antibodies defined by their amino acid sequences and comprising SEQ ID NO: 4, 10, 2 and 12 for DR5-01 and SEQ ID NO: 8, 10, 6 and 12 for DR5-05, or SEQ ID NO: 35, 10, 37 and 12 for HzDR5-01 and SEQ ID NO: 39, 10, 41 and 12 for HzDR5-05.

The pharmaceutical compositions, uses and methods of treatment are thus intended for the prevention and/or treatment of cancer. A list of cancers that may beneficiate from the invention is given supra in the Definitions.

The pharmaceutical compositions, uses and methods of treatment are thus also intended for the prevention and/or treatment of autoimmune diseases and inflammatory conditions. The following diseases are in particular concerned.

The pharmaceutical compositions, uses and methods of treatment are thus also intended for the prevention and/or treatment of viral infection or viral diseases. Viral infections and diseases include, but are not limited to, infections with cytomegalovirus, influenza, Newcastle, disease virus, vesicular stomatitis virus, herpes simplex virus, hepatitis, adenovirus-2, bovine viral diarrhoea virus, human immunodeficiency virus (HIV), and Epstein-Barr virus.

In a particular embodiment, the polypeptides, antibodies or bispecific antibodies of this invention can also be used to specifically label cancer cells, solid tumors, and the like, and more generally, to specifically target/deliver any conjugated or otherwise coupled effector (e.g. radioisotope, label, cytotoxin, drug, liposome, antibody, nucleic acid, dendrimer, etc. . . . ) to cancer cells including, but not limited to, isolated cancer cells, metastatic cells, solid tumor cells, and the like.

Therefore, another object of the invention is a complex of a polypeptide according to the invention and a molecule, which is an effector molecule, which function may beneficiate from the targeting of the DR5 receptor by the polypeptide. Such an effector molecule may be a radioisotope, a label, a cytotoxin, a drug, a liposome, an antibody, a nucleic acid, a dendrimer. The invention also concerns a pharmaceutical composition containing this complex and a pharmaceutically acceptable vehicle, diluent or excipient.

The invention also concern the use of such composition, and a method as well, to prevent or treat a cancer, such as one of those cited supra in the Definitions.

A polypeptide or the polypeptides of this invention may be used to identify other polypeptides or antibodies that bind to one of the epitopes against which the DR5-01 and the DR5-05 are directed. Thus, in certain embodiments, a polypeptide or antibody of this invention, directed against one epitope, can be used or paired with another antibody with binding specificity for the other epitope DR5.

A polypeptide or the polypeptides of this invention may be used to identify other polypeptides or antibodies that bind to another epitope on DR5, which upon binding of polypeptides or antibodies on these various epitopes on DR5, induce apoptosis. DR5-01 and/or the DR5-05 are directed. Thus, in certain embodiments, a polypeptide or antibody of this invention, directed against one epitope (DR5-01 or DR5-05), or polypeptides or antibodies of this invention, directed against both epitopes (DR5-01 and DR5-05) can be used with another antibody with binding specificity for another epitope on DR5.

One or more polypeptides, antibodies, bispecific antibodies, and/or functionalized bispecific antibodies, and/or chimeric moieties of this invention, or pharmaceutical compositions containing the same, can be administered by injection, that is, intravenously, intramuscularly, intracutaneously, subcutaneously, intraduodenally or intraperitoneally. Also in certain embodiments, the compounds can be administered by inhalation, for example, intranasally. Other pharmaceutical delivery systems can also be employed, for example, liposomes.

Targeting DR5 with the polypeptides or antibodies of the present invention in combination with existing chemotherapeutic treatments will be more effective in killing the tumor cells than chemotherapy alone. A wide variety of drugs have been employed in chemotherapy of cancer. Examples include, but are not limited to, cisplatin, taxol, etoposide, mitoxantrone, actinomycin D, campthotecin, methotrexate, gemcitabine, mitomycin, dacarbazine, 5-fluorouracil, doxorubicine and daunomycin.

In one approach, antibody combination or bispecific antibody anti-DR5 MAb is added to a standard chemotherapy regimen, in treating a cancer patient. For those combinations in which the antibody and additional anti-cancer agent(s) exert a synergistic effect against cancer cells, the dosage of the additional agent(s) may be reduced, compared to the standard dosage of the second agent when administered alone. The antibody may be co-administered with an amount of an anti-cancer drug that is effective in enhancing sensitivity of cancer cells to the antibody combination or bispecific antibody.

In one method of the invention, targeting DR5 with antibody combination or bispecific antibody, is administered to the patient prior to administration of a second anti-cancer agent. One alternative method comprises administering the second anti-cancer agent prior to administering the antibody combination or the bispecific antibody and second agent on an alternative schedule. In another embodiment, the antibody combination or bispecific antibody and second agent are administered simultaneously.

The method of the invention may provide for the inclusion in a therapeutic regimen involving the use of at least one other treatment method, such as irradiation, chemotherapy with small molecule or antibody. The method of the invention may directly include the administration of a sufficient amount of at least one additional polypeptide or antibody directed against another target and/or at least one chemotherapeutic drug (such as small molecule), for a simultaneous, separate or sequential administration with polypeptide(s) or antibody(ies) of the invention, to a mammal, including man. As additional active principle, one may cite doxorubicine, gemcitabine, camptothecin, paclitaxel or the other drugs mentioned above. In an embodiment, lung cancer and breast cancer is treated using such combination. This combination more generally is useful for cancers (in particular aggressive cancers) which do not respond well to treatment with the drug alone or the antibodies/antibody of the invention alone, and for which the combination leads to a synergistic effect.

In one method of the invention, targeting DR5 with antibody combination or bispecific antibody or multivalent antibody fragment, may be employed in treating viral infections and associated conditions arising from viral infections. Viral infections, include, but are not limited to, infections with cytomegalovirus, influenza, Newcastle, disease virus, vesicular stomatitus virus, herpes simplex virus, hepatitis, adenovirus-2, bovine viral diarrhea virus, human immunodeficiency virus (HIV), and Epstein-Barr virus.

Mammalian cells are the preferred hosts for production of therapeutic glycoproteins, due to their capability to glycosylate proteins in the most compatible form for human applications. Bacteria very rarely glycosylate proteins, and like other type of common hosts, such as yeasts, filamentous fungi, insect and plant cells yield glycosylation patterns associated with rapid clearance from the blood stream.

Among mammalian cells, Chinese hamster ovary (CHO) cells are the most commonly used. In addition to giving suitable glycosylation patterns, these cells allow consistent generation of genetically stable, highly productive clonal cell lines. They can be cultured to high densities in simple bioreactors using serum-free media, and permit the development of safe and reproducible bioprocesses. Other commonly used animal cells include baby hamster kidney (BHK) cells, NSO- and SP2/0-mouse myeloma cells.

In an embodiment, the polypeptides and antibodies according to the invention are produced or expressed in mammal cells, preferably wild-type mammal cells, preferably of rodent origin, especially CHO cells.

Modifications and changes may be made in the structure of a polypeptide of the present invention and still obtain a molecule having like characteristics. For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence (or, of course, its underlying DNA coding sequence) and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics.

It is believed that the relative hydropathic character of the amino acid determines the secondary structure of the resultant polypeptide, which in turn defines the interaction of the polypeptide with other molecules, for example, enzymes, substrates, receptors, antibodies, antigens, and the like. It is known in the art that an amino acid may be substituted by another amino acid having a similar hydropathic index and still obtain a biologically functionally equivalent polypeptide. In such changes, the substitution of amino acids whose hydropathic indices are within +2 is preferred, those which are within +1 are particularly preferred, and those within +0.5 are even more particularly preferred.

Substitution of like amino acids can also be made on the basis of hydrophilicity, particularly where the biologically functionally equivalent peptide or polypeptide thereby created is intended for use in immunological embodiments. U.S. Pat. No. 4,554,101, incorporated herein by reference or to which the person skilled in the art: may refer, states that the greatest local average hydrophilicity of a polypeptide, as governed by the hydrophilicity of its adjacent amino acids, correlate with its immunogenicity and antigenicity, i.e. with a biological property of the polypeptide.

As detailed in U.S. Pat. No. 4,554,101, the following hydrophilicity values have been assigned to amino acid residues: arginine (+3.0); lysine (+3.0); aspartate (+3.0 +1); glutamate (+3.0 +1); serine (+0.3); asparagine (+0.2); glutamine (+0.2); glycine (0); proline (−0.5 +1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent, polypeptide. In such changes, the substitution of amino acids whose hydrophilicity values are within +2 is preferred, those which are within +1 are particularly preferred, and those within +0.5 are even more particularly preferred.

As outlined above, amino acid substitutions are generally therefore based on the relative similarity of the amino acid side-chain substituents, for example, their hydrophobicity, hydrophilicity, charge, size, and the like.

TABLE 5

| Amino Acid | Index |
| --- | --- |
| isoleucine L | (+4.5) |
| valine V | (+4.2) |
| leucine L | (+3.8) |
| phenylalanine | (+2.8) |
| cysteine C | (+2.5) |
| methionine M | (+1.9) |
| alanine A | (+1.8) |
| glycine G | (−0.4) |
| threonine T | (−0.7) |
| serine S | (−0.8) |
| tryptophan W | (−0.9) |
| tyrosine Y | (−1.3) |
| proline P | (−1.6) |
| histidine H | (−3.2) |
| glutamate E | (−3.5) |
| glutamine Q | (−3.5) |
| aspartate D | (−3.5) |
| asparagine N | (−3.5) |
| lysine K | (−3.9) |
| arginine R | (−4.5) |

Amino acid substitution may be chosen or selected differently. Possible substitutions have been documented in WO99/51642, WO2007024249 and WO2007106707.

By definition, the CDRs of the invention include variant CDRs, by deletion, substitution or addition of one or more amino acid(s), which variant keeps the specificity of the original CDR. The common numbering system provides for a CDR definition having the shortest amino acid sequences or the minimal CDR definition.

The antibody may be a monoclonal antibody, a chimeric antibody, a humanized antibody, a full human antibody, a bispecific antibody, an antibody drug conjugate or an antibody fragment. A "humanized antibody" or "chimeric humanized antibody" shall mean an antibody derived from a non human antibody, typically a murine antibody, that retains or substantially retains the antigen-binding properties of the parental antibody, but which is less immunogenic in humans.

Methods for producing the polypeptides and antibodies are known from the person skilled in the art. The mammal cells, preferably rodent cells such as CHO cells, preferably wild-type cells are transfected with one or several expression vectors. Preferably, the cells are co-transfected with an expression vector for light chain and with an expression vector for heavy chain.

Cell transfection is also known from the person skilled in the art. As transfection that may be performed, one may mention without limitation standard transfection procedures, well-known from the man skilled in the art, such as calcium phosphate precipitation, DEAE-Dextran mediated transfection, electroporation, magnetofection, nucleofection (AMAXA Gmbh, GE), liposome-mediated transfection (using Dreamfect®, Lipofectin® or Lipofectamine® technology for example) or microinjection.

Expression vectors are known. As vectors that may be used, one may mention without limitation: pcDNA3.3, pOptiVEC, pFUSE, pMCMVHE, pMONO, pSPORT1, pcDV1, pcDNA3, pcDNA1, pRc/CMV, pSEC. One may use a single expression vector or several expression vectors expressing different parts of the polypeptide or antibody.

An expression vector for the CH1, hinge region, CH2 and CH3 comprises SEQ ID NO: 9 or comprises a nucleic acid sequence encoding amino acid sequence SEQ ID NO: 10.

An expression vector contains a nucleic acid sequence encoding a variable region VH of the invention. In an embodiment, the vector comprises SEQ ID NO: 3 or comprises a nucleic acid sequence encoding amino acid sequences SEQ ID NO: 4. In another embodiment, it comprises SEQ ID NO: 7 or comprises a nucleic acid sequence encoding amino acid sequences SEQ ID NO: 8. In an embodiment, the vector comprises SEQ ID NO: 34 or comprises a nucleic acid sequence encoding amino acid sequences SEQ ID NO: 35. In another embodiment, it comprises SEQ ID NO: 38 or comprises a nucleic acid sequence encoding amino acid sequences SEQ ID NO: 39.

A set of expression vectors encoding a heavy chain, comprise an expression vector which comprises SEQ ID NO: 9 (or comprises a nucleic acid sequence encoding amino acid sequence SEQ ID NO: 10), and either SEQ ID NO: 3 (or a nucleic acid sequence encoding amino acid sequences SEQ ID NO: 4) or SEQ ID NO: 7 (or a nucleic acid sequence encoding amino acid sequences SEQ ID NO: 8). A set of expression vectors encoding a heavy chain, comprise an expression vector which comprises SEQ ID NO: 9 (or comprises a nucleic acid sequence encoding amino acid sequence SEQ ID NO: 10), and either SEQ ID NO: 34 (or a nucleic acid sequence encoding amino acid sequences SEQ ID NO: 35) or SEQ ID NO: 38 (or a nucleic acid sequence encoding amino acid sequences SEQ ID NO: 39).

A single expression vector for the heavy chain contains a nucleic acid sequence which encodes VH, CH1, hinge region, CH2, CH3. In an embodiment, the vector comprises SEQ ID NO: 3 and 9 or comprises a nucleic acid sequence encoding amino acid sequences SEQ ID NO: 4 and 10. In another embodiment, it comprises SEQ ID NO: 7 and 9 or comprises a nucleic acid sequence encoding amino acid sequences SEQ ID NO: 8 and 10. In an embodiment, the vector comprises SEQ ID NO: 34 and 9 or comprises a nucleic acid sequence encoding amino acid sequences SEQ ID NO: 35 and 10. In another embodiment, it comprises SEQ ID NO: 38 and 9 or comprises a nucleic acid sequence encoding amino acid sequences SEQ ID NO: 39 and 10.

An expression vector for the light constant chain comprises SEQ ID NO: 11 or comprises a nucleic acid sequence encoding amino acid sequence SEQ ID NO: 12.

An expression vector contains a nucleic acid sequence encoding a variable region VL of the invention. In an embodiment, the vector comprises SEQ ID NO: 1 or a nucleic acid sequence encoding amino acid sequence SEQ ID NO: 2. In another embodiment, it comprises SEQ ID NO: 5 or a nucleic acid sequence encoding amino acid sequence SEQ ID NO: 6. In an embodiment, the vector comprises SEQ ID NO: 36 or a nucleic acid sequence encoding amino acid sequence SEQ ID NO: 37. In another embodiment, it comprises SEQ ID NO: 40 or a nucleic acid sequence encoding amino acid sequence SEQ ID NO: 41.

An expression vector contains a nucleic acid sequence encoding a light chain of the invention. In an embodiment, the vector comprises SEQ ID NO: 1 and 11 or a nucleic acid sequence encoding amino acid sequences SEQ ID NO: 2 and 12. In another embodiment, it comprises SEQ ID NO: 5 and 11 or a nucleic acid sequence encoding amino acid sequences SEQ ID NO: 6 and 12. In an embodiment, the vector comprises SEQ ID NO: 36 and 11 or a nucleic acid sequence encoding amino acid sequences SEQ ID NO: 37 and 12. In another embodiment, it comprises SEQ ID NO: 40 and 11 or a nucleic acid sequence encoding amino acid sequences SEQ ID NO: 41 and 12.

A set of expression vectors for producing a complete antibody comprise several vectors, for example two or three.

A single expression vector may also be used, which comprise either SEQ ID NO: 3, 9, 1 and 11 (or a nucleic acid sequence encoding amino acid sequence SEQ ID NO: 4, 10, 2 and 12), or SEQ ID NO: 7, 9, 5 and 11 (or a nucleic acid sequence encoding amino acid sequence SEQ ID NO: 8, 10, 6 and 12). A single expression vector may also be used, which comprise either SEQ ID NO: 34, 9, 36 and 11 (or a nucleic acid sequence encoding amino acid sequence SEQ ID NO: 35, 10, 37 and 12), or SEQ ID NO: 38, 9, 40 and 11 (or a nucleic acid sequence encoding amino acid sequence SEQ ID NO: 39, 10, 41 and 12).

The expression vector comprises a nucleic acid sequence or nucleic acid sequences which code(s) for the variable region that is wished. Various embodiments of variable regions which can be expressed by the vector are presented below. Embodiments of these vectors are defined by using the CDRs definitions according to IMGT®. However, the invention encompasses and relates also to the equivalent or alternative vectors wherein the IMGT® numbering is replaced either by the Kabat® numbering or the Common numbering system, using the sequences indicated supra. Therefore, in the following embodiments of a vector, other embodiments are part of the invention in which one replaces the CDRs defined with IMGT® numbering, by the Kabat® numbering, in accordance with the table supra. Also, in the following embodiments of a vector, other embodiments are part of the invention in which one replaces the CDRs defined with IMGT® numbering, by the Common numbering system, in accordance with the table supra.

An expression vector codes for a VH comprising a CDR1 of sequence SEQ ID NO: 13, a CDR2 of sequence SEQ ID NO: 14 CDR1, a CDR3 of sequence SEQ ID NO: 15.

An expression vector codes for a VL comprising a CDR1 of sequence SEQ ID NO: 16, a CDR2 of sequence FAS, a CDR3 of sequence SEQ ID NO: 17.

A set of expression vectors comprise an expression vector which codes for a VH comprising a CDR1 of sequence SEQ ID NO: 13, a CDR2 of sequence SEQ ID NO: 14 CDR1, a CDR3 of sequence SEQ ID NO: 15, and an expression vector which codes for a VL comprising a CDR1 of sequence SEQ ID NO: 16, a CDR2 of sequence FAS, a CDR3 of sequence SEQ ID NO: 17.

An expression vector comprises a nucleic acid sequence coding for a VH comprising a CDR1 of sequence SEQ ID NO: 13, a CDR2 of sequence SEQ ID NO: 14 CDR1, a CDR3 of sequence SEQ ID NO: 15, and a nucleic acid sequence coding for a VL comprising a CDR1 of sequence SEQ ID NO: 16, a CDR2 of sequence FAS, a CDR3 of sequence SEQ ID NO: 17.

An expression vector codes for a VH comprising a CDR1 of sequence SEQ ID NO: 18, a CDR2 of sequence SEQ ID NO: 14, a CDR3 of sequence SEQ ID NO: 19.

An expression vector codes for a VL comprising a CDR1 of sequence SEQ ID NO: 20, a CDR2 of sequence RTS, a CDR3 of sequence SEQ ID NO: 21.

A set of expression vectors comprise an expression vector which codes for a VH comprising a CDR1 of sequence SEQ ID NO: 18, a CDR2 of sequence SEQ ID NO: 14, a CDR3 of sequence SEQ ID NO: 19, and an expression vector which codes for a VL comprising a CDR1 of sequence SEQ ID NO: 20, a CDR2 of sequence RTS, a CDR3 of sequence SEQ ID NO: 21.

An expression vector comprises a nucleic acid sequence coding for a VH comprising a CDR1 of sequence SEQ ID NO: 18, a CDR2 of sequence SEQ ID NO: 14, a CDR3 of sequence SEQ ID NO: 19, and a nucleic acid sequence coding for a VL comprising a CDR1 of sequence SEQ ID NO: 20, a CDR2 of sequence RTS, a CDR3 of sequence SEQ ID NO: 21.

The invention thus comprises the use of one single vector or a set of vectors to produce the polypeptides or antibodies of the invention. These vectors are also objects of the invention, alone or as a set of vectors.

Another object of the invention is a host cell containing a vector or a set of vectors of the invention. The host cell may be a mammal cell, preferably a rodent cell, more preferably CHO cell. Still more preferably, the host cell may be a wild-type mammal cell, preferably a wild-type rodent cell, most preferably a wild-type CHO cell.

The person skilled in the art fully owns the methods to generate the antibodies according to the invention using such a vector or vectors and cells such as CHO cells.

BRIEF DESCRIPTION OF THE DRAWINGS

The present invention will now be described in further detail by way of examples referring to the figure. Note that in the block diagrams, the blocks appear from the left to the right in the same order than indicated in the legend in the diagrams where the legend is put in a box.

FIG. 1 shows the FACS analysis of anti-DR5 antibody panel in human glioma cell lines (H4, HS683, A172, T98G, U87MG).

FIG. 2 shows the FACS analysis of anti-DR5 expression in some cancer cell lines such as human kidney adenocarcinoma (A704, ACHN, Caki1), human colon carcinoma (SW948, HCT 116), human urinary bladder carcinoma (5637) and human breast adenocarcinoma (MCF7).

FIG. 25 Amino acid and nucleic acid sequence for VH HzDR5-01 with description of the FR1, CDR1, FR2, CDR2, FR3, CDR3 defining according IMGT®.

FIG. 26 Amino acid and nucleic acid sequence for VL HzDR5-01 with description of the FR1, CDR1, FR2, CDR2, FR3, CDR3 defining according IMGT®.

FIG. 27 Amino acid and nucleic acid sequence for VH HzDR5-05 with description of the FR1, CDR1, FR2, CDR2, FR3, CDR3 defining according IMGT®.

FIG. 28 Amino acid and nucleic acid sequence for VL HzDR5-05 with description of the FR1, CDR1, FR2, CDR2, FR3, CDR3 defining according IMGT®.

EXAMPLES

Figure 3:
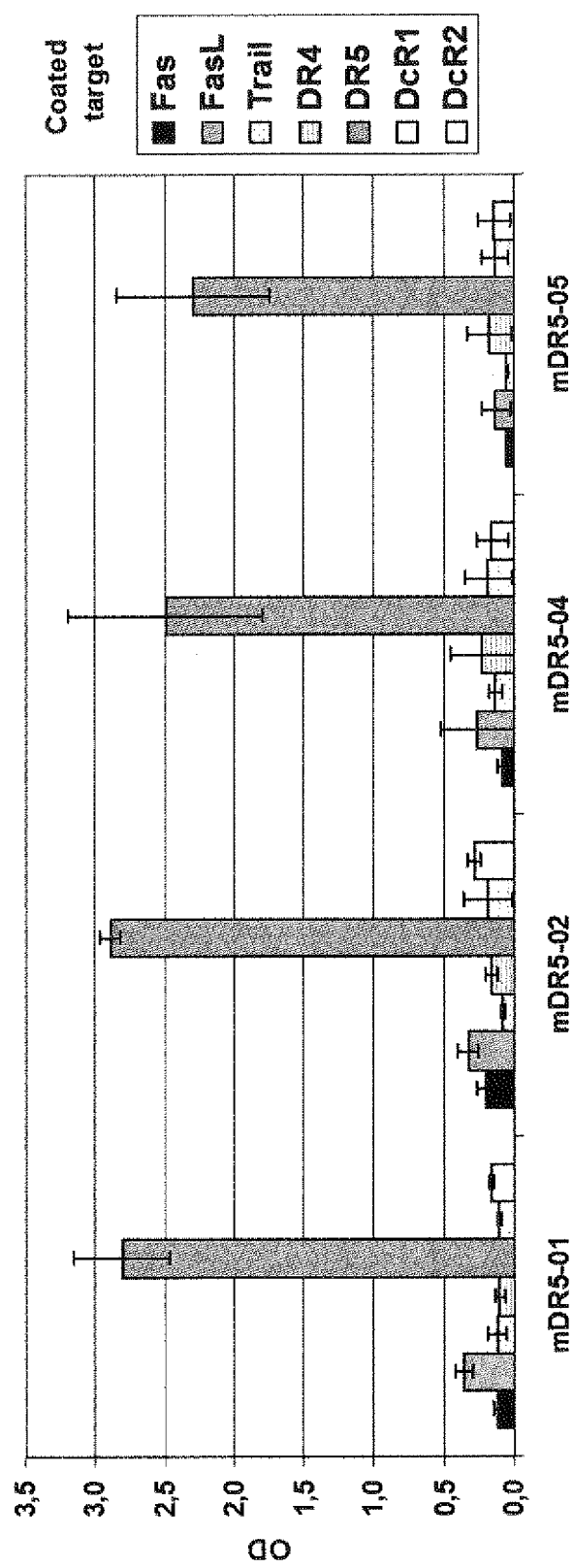
FIG. 3 is a graph showing the results of an ELISA assay evaluating binding of MAbs (1 µg/mL) to Fas (50 ng/mL), FasL (100 ng/mL), TRAIL (100 ng/mL) and to DR4, DR5, DcR1 or DcR2 (50 ng/mL), (mean+/−SD, n=2).

The following examples are offered to illustrate, but not to limit the claimed invention.

Example 1

Preparation of Murine MAb Anti-DR5

This example illustrates the preparation of hybridoma cell lines secreting anti-DR5 antibodies.

Antibodies.

The anti-DR5 antibodies, murine monoclonal antibodies specific for DR5 were produced using standard hybridoma techniques (Zola et al., *Aust J. Exp Biol Med Sci.* 1981; 59:303-6). Briefly, mice were given i.p. injections of recombinant DR5 (10 µg), (R&D Systems, Lille, France) on weeks 0, 2 and 4. This was followed by an i.v. injection of recombinant DR5 (10 µg) and the splenocytes were fused with mouse myeloma line X63-Ag8.653. Hybridoma supernatants were screened for DR5 binding by ELISA and by flow cytometry on DR5 positive cell lines. A murine MAb panel anti-DR5 noted mDR5-01, mDR5-02, mDR5-04 and mDR5-05 were obtained.

Example 2

Cell Culture

Various tumor-derived cell lines are among the target cells that may be contacted with TRAIL, anti-DR5 MAb alone, MAb combination, in such assay procedures.

Cell lines. The established human neuroglioma cells H4, HS683 or A172 (available from ATCC) and the established human lung adenocarcinoma cells A549 were grown in Dulbecco's Modified Eagle's Medium (Sigma, St Quentin Fallavier, France) supplemented with 10% heat-inactivated fetal bovine serum (FBS) (Sigma, St Quentin Fallavier, France), 4 nM L-glutamine (Sigma, St Quentin Fallavier, France) and 100 U/mL, 100 µg/mL penicillin-streptomycin (Sigma, St Quentin Fallavier, France). The established human glioblastoma astrocytoma cells U87MG or T98G, the human kidney adenocarcinoma cells A704, the human kidney adenocarcinoma cells ACHN and the human breast adenocarcinoma cells MCF7 (available from ATCC) were grown in Eagle's Minimum Essential Medium (Sigma, St Quentin Fallavier, France) supplemented with 10% heat-inactivated fetal bovine serum (FBS) (Sigma, St Quentin Fallavier, France), 4 nM L-glutamine (Sigma, St Quentin Fallavier, France) and 100 U/mL, 100 µg/mL penicillin-streptomycine (Sigma, St Quentin Fallavier, France). The established human colon adenocarcinoma cells SW948 and the human breast adenocarcinoma cells MDAMB231 (available from ATCC) were grown in Leibovitz's L-15 (Sigma, St Quentin Fallavier, France) supplemented with 10% heat-inactivated fetal bovine serum (FBS) (Sigma, St Quentin Fallavier, France), 4 nM L-glutamine (Sigma, St Quentin Fallavier, France) and 100 U/mL, 100 µg/mL penicillin-streptomycine (Sigma, St Quentin Fallavier, France). The established human kidney carcinoma cells Caki-1 and the human colorectal carcinoma cells HCT-116 (available from ATCC) were grown in McCoy's 5A Medium Modified (Sigma, St Quentin Fallavier, France) supplemented with 10% heat-inactivated fetal bovine serum (FBS) (Sigma, St Quentin Fallavier, France), 4 nM L-glutamine (Sigma, St Quentin Fallavier, France) and 100 U/mL, 100 µg/mL penicillin-streptomycine (Sigma, St Quentin Fallavier, France). The established human urinary bladder carcinoma cells 5637 and the established human lung adenocarcinoma cells NCIH1703 (available from ATCC) were grown in RPMI-1640 Medium (Sigma, St Quentin Fallavier, France) supplemented with 10% heat-inactivated fetal bovine serum (FBS) (Sigma, St Quentin Fallavier, France), 4 nM L-glutamine (Sigma, St Quentin Fallavier, France) and 100 U/mL, 100 µg/mL penicillin-streptomycine (Sigma, St Quentin Fallavier, France). The established human glioma cells 42MGBA (available from DSMZ) were grown in 80% mixture of RPMI-1640 Medium and Eagle's Minimum Essential Medium at 1:1 (Sigma, St Quentin Fallavier, France) supplemented with 20% heat-inactivated fetal bovine serum (FBS) (Sigma, St Quentin Fallavier, France), 4 nM L-glutamine (Sigma, St Quentin Fallavier, France) and 100 U/mL, 100 µg/mL penicillin-streptomycine (Sigma, St Quentin Fallavier, France).

Example 3

Antibody Binding Assays (FCM, ELISA)

This example describes methods to determine the MAb specificity anti-DR5 by ELISA with coated antigens, to investigate on DR5 cellular expression at the cell surface. and to determine epitopes following MAb competition analyzed by flow cytometry.

Flow cytometry experiments for DR5 cellular expression. Briefly, $2\times10^5$ cells per 96 wells are incubated with a dilution of unconjugated anti-DR5 MAb at 10 µg/mL then diluted at 1/10. Unbound antibodies were washed away with PBS (Invitrogen, Villebon sur Yvette, France) supplemented by 1% Bovine Serum Albumin (Sigma, St Quentin Fallavier, France). Subsequently, cells are centrifuged (5 min at 400 g) and bound antibody is detected with Fluorescein Isothiocyanate (FITC) conjugated goat (Fab')$_2$ polyclonal anti mouse (MP Biomedical, Illkirch, France) at 4° C. for 30 min. Detection reagent is washed away and cells are centrifuged (5 min at 400 g) and resuspended in 300 µL PBS. Bound detection antibody is quantified on a FACSCAN (BD Biosciences, Rungis, France), (FL1 channel, 2000 events per acquisition). During the experiment, the respective isotype controls are included to exclude any unspecific binding events.

Results of experiments are shown in FIG. 1 (at 10 µg/mL), FIG. 2 and Table 6 (at 5 µg/mL) shows as for example the cell staining with MAb concentration or at 5 µg/mL. Various cancer cell lines express different subsets of TRAIL receptors. Expression patterns varied from cell line to cell lines. In the present study DR5 was expressed on all cell lines tested. Whatever the MAb tested anti-DR5 (mDR5-01, mDR5-02, mDR5-04 or mDR5-05), similar cellular pattern was observed.

Table 6 shows the FACS analysis of DR5 expression using 5 µg/mL of anti-DR5 antibody in other solid tumour cell lines ($1\times10^6$ cells/mL) i.e. human breast adenocarcinoma cell lines (MCF7, MDAMB231) and on human lung adenocarcinoma cell lines (NCIH1703, A549).

TABLE 6

| | Breast cancer cell line | | | | Lung cancer cell line | | | |
|---|---|---|---|---|---|---|---|---|
| | MCF7 | | MDAMB231 | | NCIH1703 | | A549 | |
| Mab | % | MFI | % | MFI | % | MFI | % | MFI |
| mIgG1 CTRL | 1 | 176 | 0 | 119 | 0 | 100 | 0 | 190 |
| mDR5-01 | 51 | 225 | 89 | 238 | 64 | 152 | 82 | 323 |
| mDR5-05 | 33 | 192 | 82 | 224 | 74 | 166 | 71 | 274 |

Analysis of MAb specificity by using coated antigens ELISA. The specific binding properties of antibodies were evaluated in an ELISA with coated Fas (50 ng/mL) (R&D Systems, Lille, France), FasL (100 ng/mL) (Tebu-bio, Le Perray en Yvelines, France), TRAIL (100 ng/mL) (R&D Systems, Lille, France), DR4 (50 ng/mL) (R&D Systems, Lille, France), DR5 (50 ng/mL) (R&D Systems, Lille, France), DcR1 (50 ng/mL) (R&D Systems, Lille, France) or DcR2 (50 ng/mL) (R&D Systems, Lille, France) antigens. The anti-DR5 MAb panel was tested at 1 µg/mL and revealed by using a goat polyclonal anti mouse IgG1 Horse Radish Peroxydase (HRP) conjugated (AbD Serotec, Colmar, France).

Results of experiments are shown in FIG. 3. The mDR5-01, mDR5-02, mDR5-04 and mDR5-05 antibodies (1 µg/mL) only reacted with DR5 coated antigens (50 ng/mL). No reactivity was observed with other apoptotic related antigens (FAS, FASL, TRAIL, DR4, DcR1, DcR2), (mean+/−SD on 2 independent experiments).

Flow cytometry experiments for MAb competition binding. Briefly, $2 \times 10^5$ cells T98G per 96 wells are incubated with a dilution of biotinylated murine antibody anti-DR5 (10 µg/mL then diluted at 1/10) as a reference and with or without unconjugated antibody at 5 µg/mL and incubated at 4° C. for 30 min. Only data obtained with 1 µg/mL of biotinylated antibody is shown. Unbound antibody is washed away with PBS (Invitrogen, Villebon sur Yvette, France) supplemented by 1% Bovine Serum Albumin (Sigma, St Quentin Fallavier, France). Subsequently, cells are centrifuged (5 min at 400 g) and bound antibody is detected with Phycoerythrin conjugated Streptavidin (Interchim, Montluçon, France) at 4° C. for 30 min. Detection reagent is washed away and cells are centrifuged (5 min at 400 g) and resuspended in 300 µL PBS. Bound detection antibody is quantified on a FACSCAN (BD Biosciences, Rungis, France), (FL2 channel, 2000 events per acquisition). During the experiment, the respective isotype controls are included to exclude any unspecific binding events.

Figure 4:
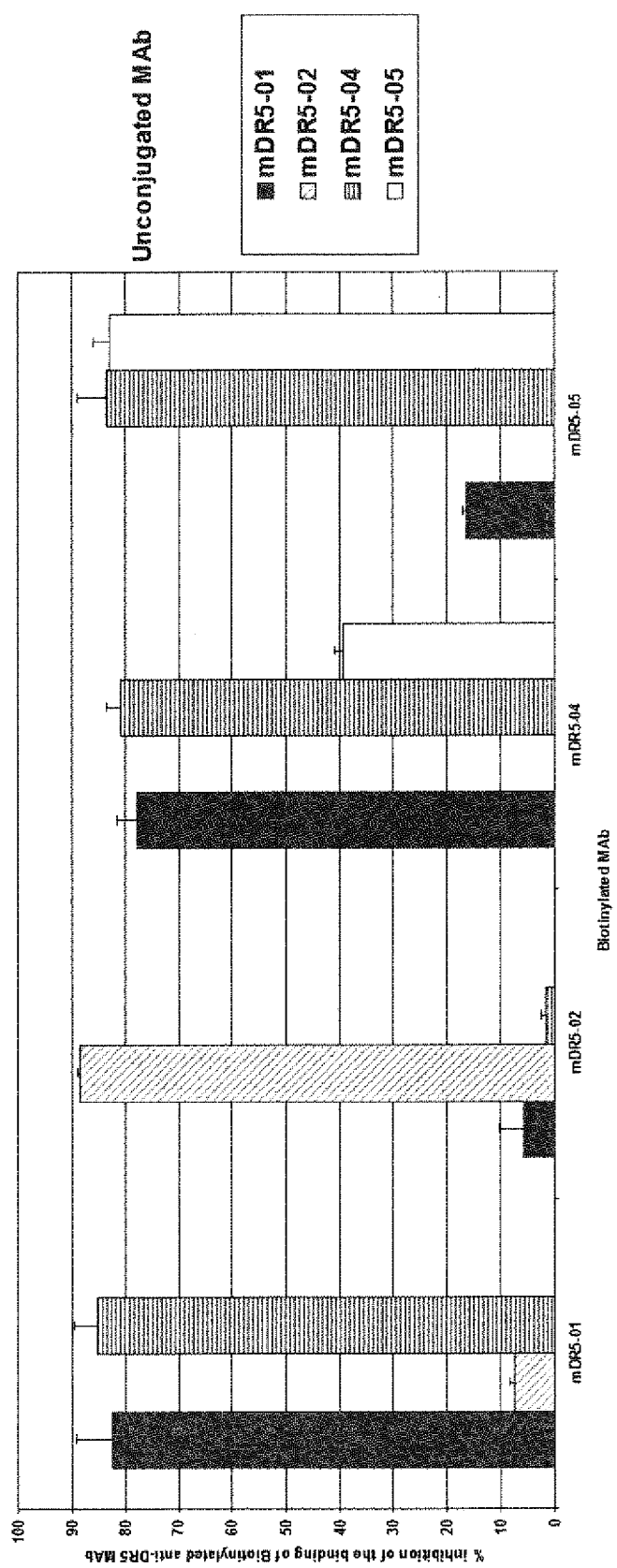
FIG. 4 is a bar diagram showing percent (%) of the inhibition of biotinylated anti-DR5 MAb binding (1 µg/mL, FACS analysis) in the presence of other unconjugated antibody anti-DR5 (5 µg/mL) using the T98G cells ($1 \cdot 10^6$ cells/mL), (mean+/−SD, n=2).

Results of experiments are shown in FIG. 4. For example the unconjugated mDR5-02 and mDR5-05 antibodies (5 µg/mL) are not in competition with the biotinylated mDR5-01 antibody (1 µg/mL). By contrast, unconjugated mDR5-01 and mDR5-04 are in competition with the biotinylated mDR5-01 antibody. Therefore, the epitopes DR5-01 and DR5-04 are common or adjacent, whereas the epitopes DR5-02 and DR5-05 are two separate epitopes. Moreover the epitope DR5-01 is also distinct of the epitope DR5-05, (mean+/−SD on two independent experiments).

Example 3

In Vitro Biologic MAb Activity

This example illustrates methods of evaluating the anti-DR5 MAb impact on TRAIL cellular binding on their ability to trigger cellular cytotoxic effect on cancer cells. These components may be assayed for anti-tumour activity, using any of a number of suitable assays, including but not limited to assays for the ability to slow tumour growth or to kill cancer cells in vitro. Various tumour-derived cell lines are among the target cells that may be contacted with MAb combination, in such assay procedures.

Figure 6:
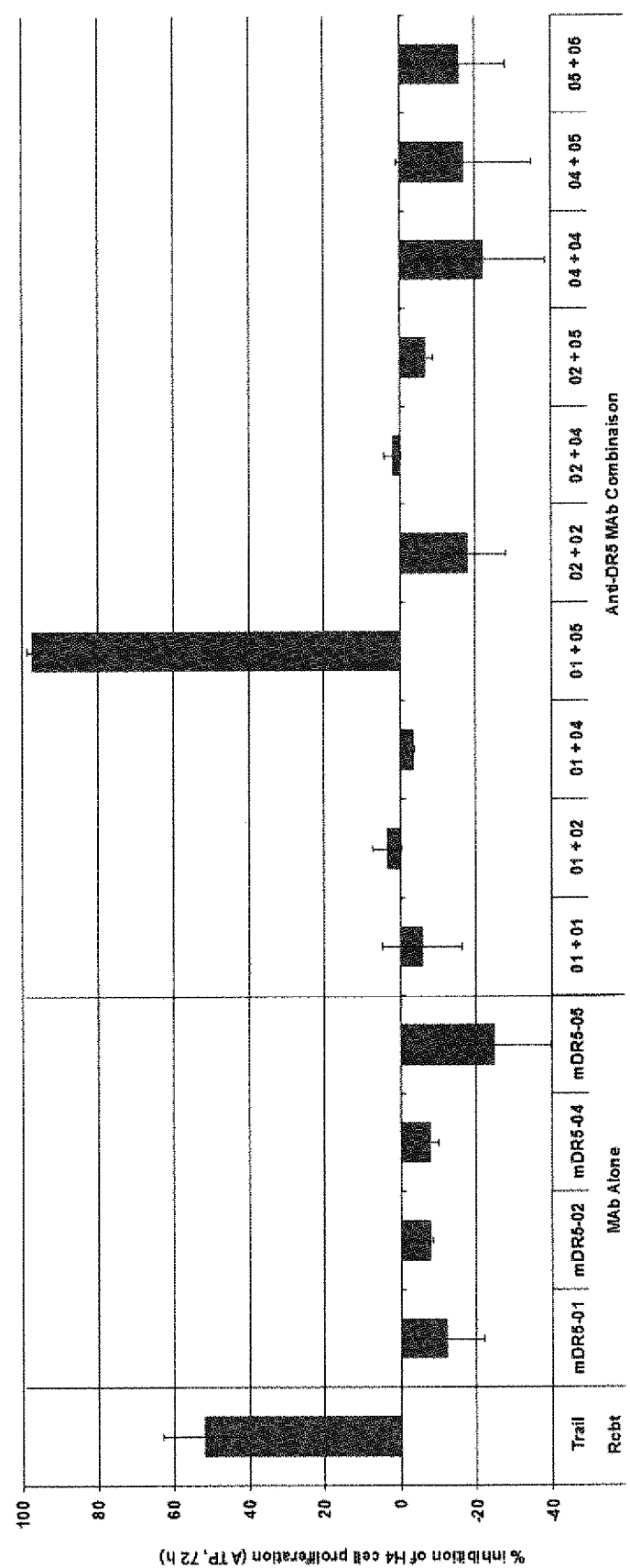
FIG. 6 is a bar diagram showing percent (%) of the cell proliferation inhibition (ATP bioluminescent bioassay, 72 hours) of anti-DR5 antibody alone or combined tested at 1 µg/mL as compared to TRAIL (10 ng/mL) using H4 cells ($5 \cdot 10^4$ cells/mL), (mean+/−SD, n=2).
Figure 7:
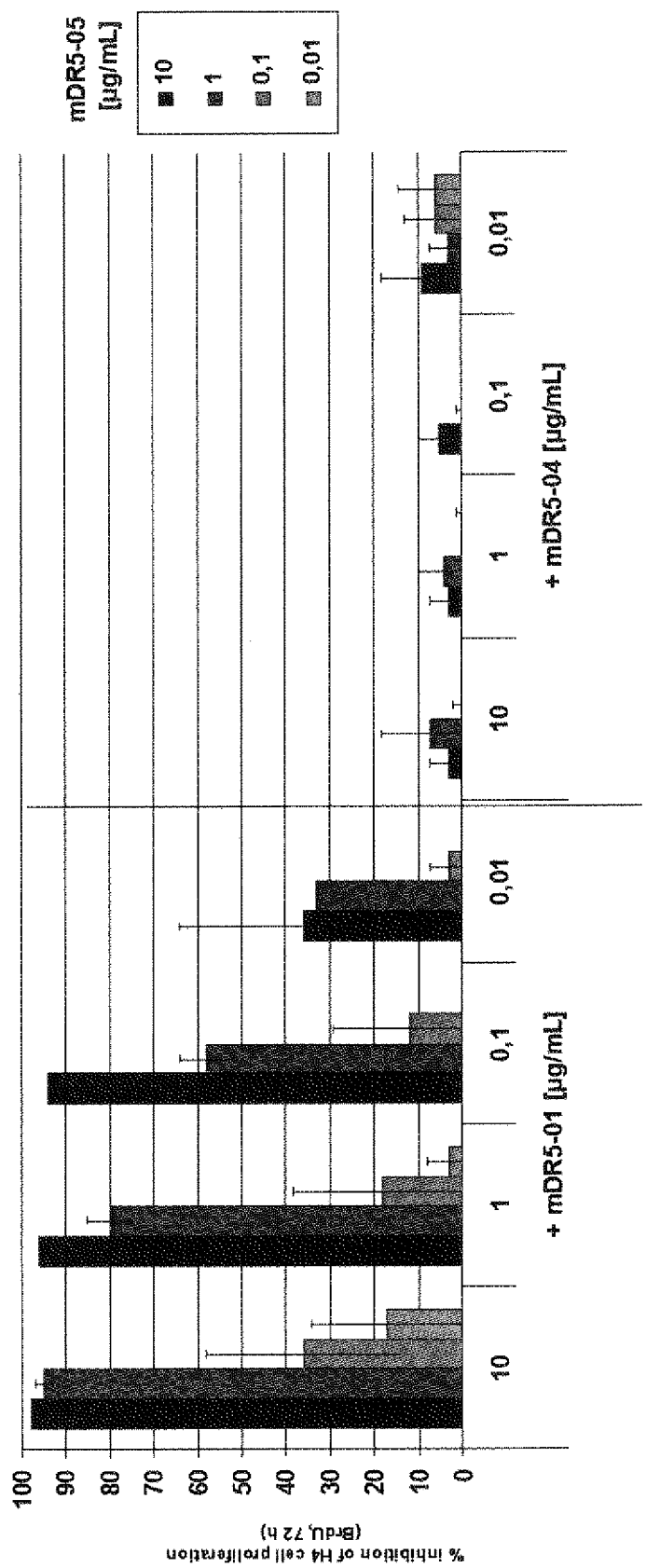
FIG. 7 is a bar diagram showing percent (%) of the cell proliferation inhibition (BrDU bioassay, 72 hours) of selective anti-DR5 agonistic antibody combination (mDR5-01+mDR5-05) versus neutral antibody combination (mDR5-05+mDR5-04) tested at different concentrations using H4 cells ($5 \cdot 10^4$ cells/mL), (mean+/−SD, n=2).
Figure 8:
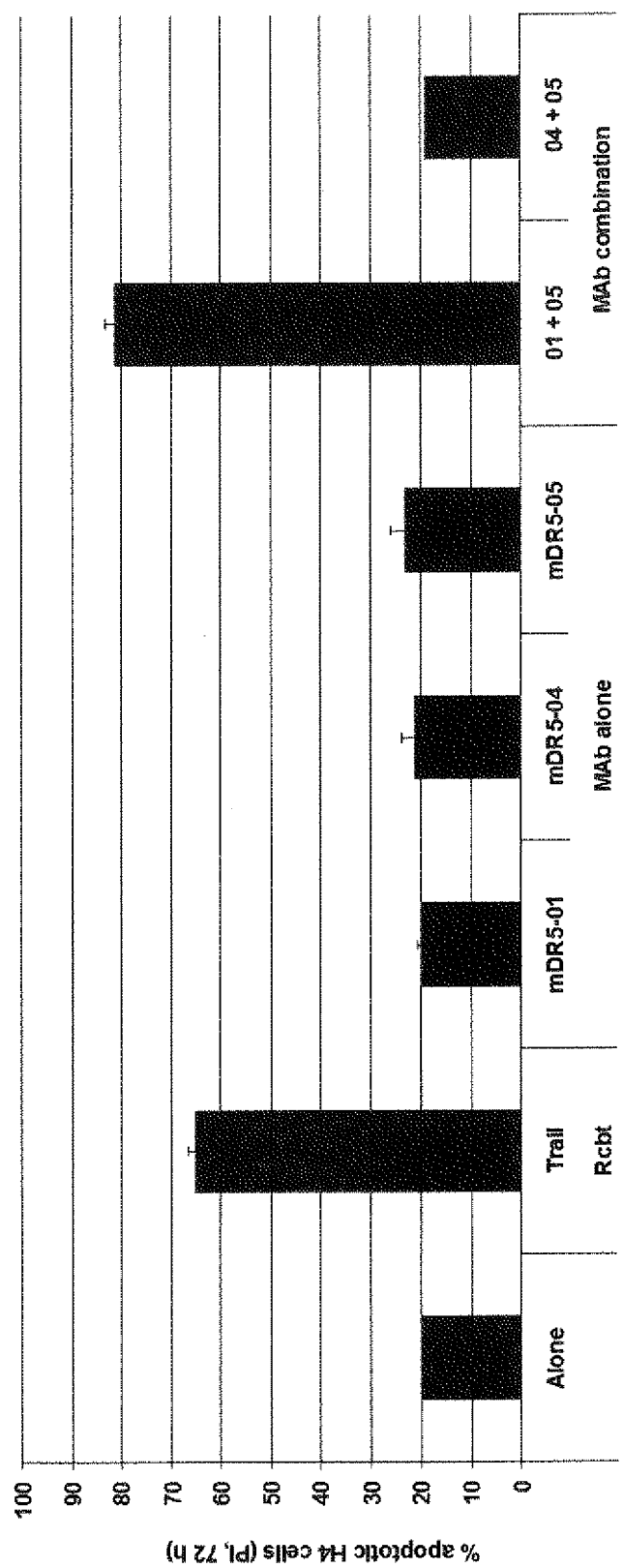
FIG. 8 is a bar diagram showing percent (%) of apoptosis (propidium iodide staining, 72 hours) of selective anti-DR5 agonistic antibody combination (mDR5-01+mDR5-05) versus neutral antibody combination (mDR5-05+mDR5-04) tested at 1 µg/mL and also compared to TRAIL (10 ng/mL) using H4 cells ($1 \cdot 10^5$ cells/mL), (mean+/−SD, n=2).
Figure 9:
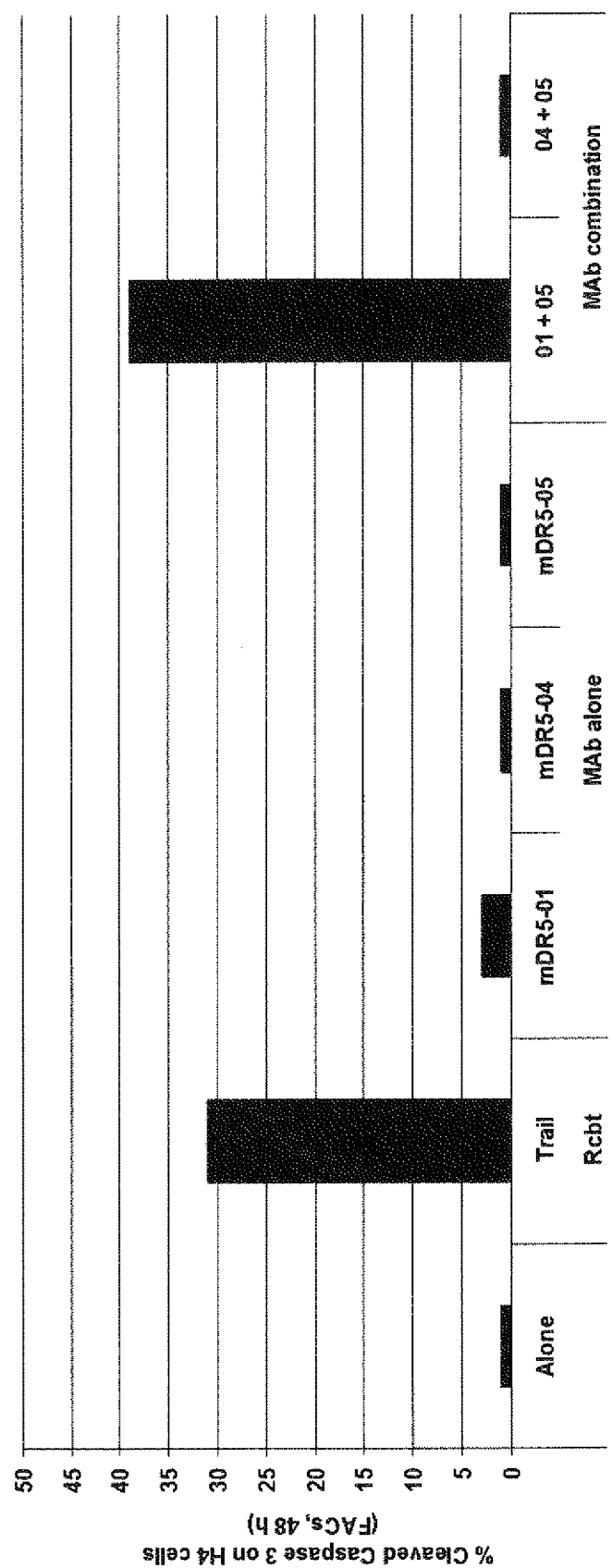
FIG. 9 is a bar diagram showing percent (%) of cleaved caspase 3 (FACS analysis, 48 hours) of selective anti-DR5 agonistic antibody combination (mDR5-01+mDR5-05) versus neutral antibody combination (mDR5-05+mDR5-04) and also compared to TRAIL using H4 cells ($1 \cdot 10^5$ cells/mL), (representative experiment, n=2).
Figure 10:
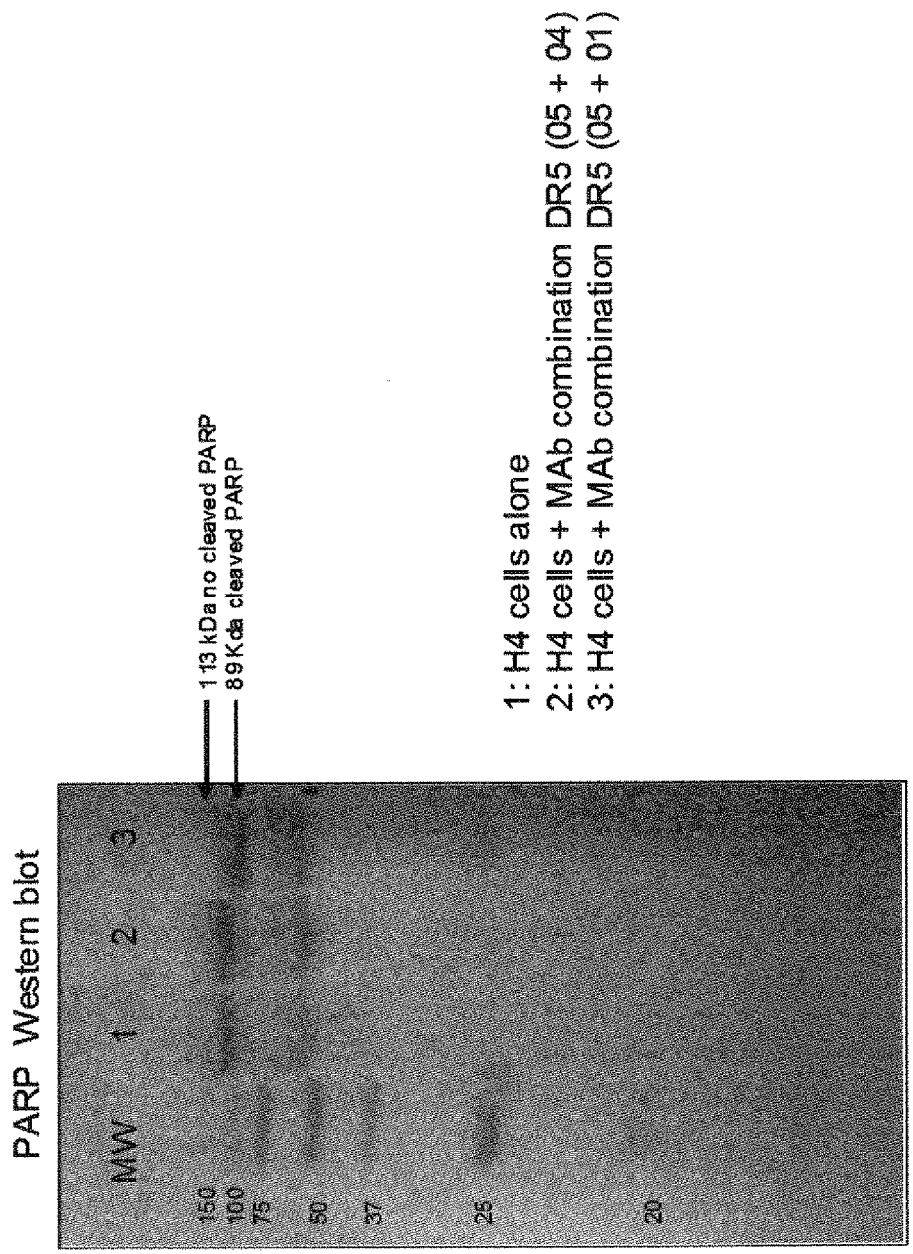
FIG. 10 is a western blot showing the cleaved PARP induced or not with the presence of selective anti-DR5 agonistic antibody combination (mDR5-01+mDR5-05) versus neutral antibody combination (mDR5-05+mDR5-04) using H4 cells ($2 \cdot 10^5$ cells/mL, 5 hours).

To identify or select anti-DR5 antibody combination which induce apoptosis, loss of membrane integrity as indicated by, e.g. PI is assessed relative to control (untreated cells) and compared to recombinant TRAIL (FIG. 8). The ability to slow tumour growth is assessed by ATP or BrDU quantification (FIG. 6, FIG. 7). The apoptotic response is assessed by quantification of cleaved caspase 3 (FIG. 9) or cleaved Poly-(ADP-Ribose)-Polymerase (PARP), (FIG. 10).

Biochemical reagents. Biochemical reagents used for the apoptosis studies were: propidium iodide (PI), (Sigma, St Quentin Fallavier, France), Caspase 3 antibody (Ozyme, Saint Quentin Yvelines, France), Cell proliferation ELISA-BrdU (Roche Diagnostics, Meylan, France), Cell Titer GLo-ATP (Promega, Charbonnières-les-bains, France) and the polyclonal anti Poly-(ADP-Ribose)-Polymerase (PARP) (Roche Diagnostics, Meylan, France).

Flow cytometry experiments of MAb impact on TRAIL binding. H4 cell lines were seeded at a density of $1 \times 10^5$ per 96-wells. Cells were incubated for 30 min at 4° C. with or without MAb anti-TRAIL or anti-DR5 (mDR5-01, mDR5-02, mDR5-3 mDR5-4) tested at 1 µg/mL then diluted at 1/10. Unbound antibodies were washed away with PBS (Invitrogen, Villebon sur Yvette, France) supplemented by 1% Bovine Serum Albumin (Sigma, St Quentin Fallavier, France). Subsequently, cells are incubated with the recombinant TRAIL (100 ng/mL), (R&D Systems, Lille, France) for 30 min at 4° C. Unbound antibodies were washed away with PBS (Invitrogen, Villebon sur Yvette, France) supplemented by 1% Bovine Serum Albumin (Sigma, St Quentin Fallavier, France). The bound recombinant TRAIL is detected with biotinylated conjugated anti TRAIL MAb B-S23 (iDD biotech, Dardilly, France). After washings, Phycoerthrin conjugated Streptavidin (Interchim, Montluçon, France) was added at 4° C. for 30 min. Detection reagent is washed away and cells are centrifuged (5 min at 400 g) and resuspended in 300 µL PBS. Bound detection antibody is quantified on a FACSCAN (BD Biosciences, Rungis, France), (FL2 channel, 2 000 events per acquisition). During the experiment, the respective isotype controls are included to exclude any unspecific binding events.

Figure 5:
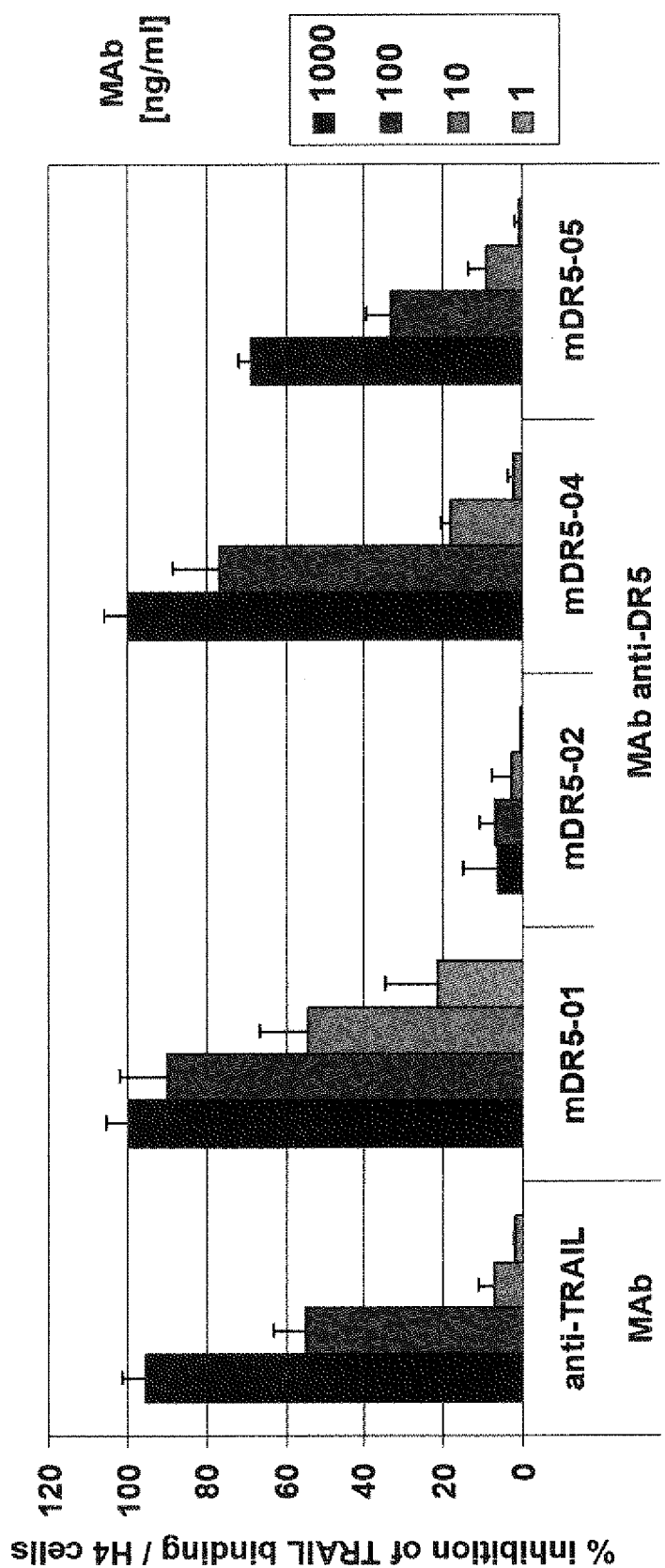
FIG. 5 is a bar diagram showing percent (%) of the inhibition of TRAIL binding (100 ng/mL, FACS analysis) in the presence of antibody (MAb anti-TRAIL, MAb anti-DR5 MAb) tested at different concentrations using H4 cells ($5 \cdot 10^5$ cells/mL), (mean+/−SD, n=2).

Human H4 expressing DR5 at the cell surface was used to determine the agonist or antagonist activity of the four anti-DR5 antibodies denoted mDR5-01, mDR5-02, mDR5-04 and mDR5-05. Results of experiments are shown in FIG. 5. The recombinant TRAIL binding at the cell surface was inhibited with the antagonist anti TRAIL MAb B-T24 (iDD biotech, Dardilly, France). Among the anti-DR5 MAb panel tested, the MAbs mDR5-01, mDR5-04 and mDR-5-05 inhibited the recombinant TRAIL binding, without any mDR5-02 MAb impact.

Cell viability analysis following ATP level determination. The CellTiter-Glo® Luminescent Cell Viability Assay (Promega, Charbonnières les Bains, France) was used to determine the number of viable cells in culture based on quantification of the ATP present, an indicator of metabolically active cells. Detection is based on using the luciferase reaction to measure the amount of ATP from viable cells. Within minutes after a loss of membrane integrity, cells lose the ability to synthesize ATP, and endogenous ATPases destroy any remaining ATP; thus the levels of ATP fall precipitously. Cell cultures ($5 \times 10^4$ cells/mL) are incubated for 72 hours alone or with anti-DR5 MAb alone (1 µg/mL) or with two combined MAb at 1 µg/mL for each MAb (FIG. 6). The TRAIL ligand concentration was used at 10 ng/mL. The CellTiter-Glo® reagent was added directly to cells in culture at a ratio of 50 µL of reagent to 200 µL of culture medium. The assay plates are incubated at room temperature for 10 min and the bioluminescent signal is recorded using a standard multiwell fluorometer Mithras LB940, (Berthold, Thoiry, France).

Results of experiments to determine the agonist activity of the four anti-DR5 antibodies are shown in FIG. 6. None of the anti-DR5 MAb alone tested was capable of inducing cellular cytotoxicity in H4 cells. By contrast, only the anti-DR5 MAb combination mDR5-01 and mDR5-05 triggered apoptosis in H4 cells. The ability of this restricted anti-DR5 MAb combination (1/10) was not related to the level of MAb staining (FIG. 1). Interestingly the MAbs mDR5-01 and mDR5-05 recognize two different epitopes (FIG. 4). However MAb combination of mDR5-05 with other mDR5 MAb such as mDR5-02 recognizing also distinct epitope failed to trigger H4 apoptosis (FIG. 6).

Cell viability analysis following BrDU incorporation determination. The H4 target cells ($5 \times 10^4$ cells/mL) were cultured with the MAb combination mDR5-05 and mDR5-01 or with the MAb combination mDR5-05 and mDR5-04 at different range of MAb concentration. Cell growth is determining using the Cell proliferation ELISA-BrdU (Roche Diagnostics, Meylan, France), according to the manufacturer's instructions. This method is based on the incorporation of the pyrimidine analogue BrdU instead of thymidine into the DNA of proliferating cells. After its incorporation into DNA, BrdU is detected with a MAb anti-BrdU. At the end of revelation, the bioluminescent signal is recorded using a standard multiwell fluorometer Mithras LB940, (Berthold, Thoiry, France).

Results of experiments are shown in FIG. 7. Specific MAb combination mDR5-01 and mDR5-05 synergistically induced apoptosis in H4 cell line as evidence by BrDU quantification, (mean+/−SD on 2 independent experiments). No significant impact was observed with the MAb combination mDR5-05 and mDR5-04.

Propidium iodide uptake by flow cytometry for measuring MAb induced apoptosis. H4 cell lines were seeded at a density of $2\times10^4$ per 96-wells. Cells were incubated for a 3 day time period with or without MAb anti-DR5. Each anti-DR5 MAb was tested alone or following MAb combination at 1 µg/mL (FIG. 8). The TRAIL ligand concentration was used at 10 ng/mL. Cells were then centrifuged at 2000 rpm for 5 min at 4° C., the pellet resuspended in 70% ethanol (Sigma, St Quentin Fallavier, France) for permeabilization. After a new centrifugation, cells were incubated with 100 µL of PI (100 µg/mL) and 100 µL of Rnase (100 µg/mL), (Sigma, St Quentin Fallavier, France) per well for 15 min. Cells are centrifuged (5 min at 2000 rpm) and resuspended in 300 µL PBS. Bound detection antibody is quantified on a FACSCAN (BD Biosciences, Rungis, France), (FL2 channel, 3000 events per acquisition).

Results of experiments are shown in FIG. 8. Whereas no PCD was obtained with MAb tested alone, specific MAb combination mDR5-01 and mDR5-05 synergistically induced apoptosis in H4 cell line as evidence by PI uptake, (mean+/−SD on 2 independent experiments). No MAb cross linking was required. No PCD was obtained with MAb combination mDR5-05 and mDR5-04.

Cleaved caspase-3 quantification by flow cytometry for measuring MAb induced apoptosis. H4 cell lines were seeded at a density of $2\times10^4$ per 96-wells. Cells were incubated for a 48 hours with or without MAb anti-DR5. Each anti-DR5 MAb was tested alone or in the presence of MAb combination at 1 µg/mL for mDR5-05 with 0.01 µg/mL for mDR5-01 or mDR5-04 (FIG. 9). The TRAIL ligand concentration was used at 10 ng/mL. Cells were then centrifuged at 2000 rpm for 5 min at 4° C., the pellet resuspended in 90% methanol (Sigma, St Quentin Fallavier, France) for permeabilization. Cells were then centrifuged at 2000 rpm for 5 min at 4° C. and incubated at 4° C. for 30 min with the MAb anti-active caspase-3 antibodies alexa fluor 488 conjugated (Ozyme, Saint Quentin Yvelines, France). Cells are centrifuged (5 min at 2000 rpm) and resuspended in 300 µL PBS. Bound detection antibody is quantified on a FACSCAN (BD Biosciences, Rungis, France), (FL2 channel, 3000 events per acquisition).

When apoptosis is activated, caspases cleave multiple protein substrates, which leads to the loss of cellular structure and function, and ultimately results in cell death. In particular, caspases-8, -9, and -3 have been implicated in apoptosis: caspase-9 in the mitochondrial pathway, caspase-8 in the Fas/CD95 pathway, and caspase-3 more downstream, activated by multiple pathways. Specific MAb combination mDR5-01 and mDR5-05 synergistically induced apoptosis in H4 cell line as evidence by cleaved caspase 3 quantification (FIG. 9), (mean+/−SD on 2 independent experiments). As compared to TRAIL (called also Apo2L), only the MAb combination mDR5-01 and mDR5-05 triggered cell apoptosis compared to the MAb combination mDR5-04 and mDR5-05.

PARP Western blotting. H4 cell lines were seeded at a density of $1\cdot10^6$ per flask T25 $cm^2$. Cells were incubated for a 5 hours with or without MAb anti-DR5. Cell extracts were resuspended in Tris-HCl 50 mM, KCl 150 mM at pH7 and submitted to sonication and incubated for 15 min at 65° C. Samples (10 µg) were subjected to reducing SDS-PAGE and transferred to PVDF membrane using standard methods. After blocking in milk 5%, the blots were incubated in the anti-Poly-(ADP-Ribose)-Polymerase (PARP) (Roche Diagnostics, Meylan, France) at 1/2000. After washing, the membranes were incubated in PAb sheep anti-rabbit IgG horseradish peroxidase conjugated antibody at 1/10000, (AbD Serotec, Colmar, France). The blots were developed with ECL Advance Western blotting using enhanced luminol-based chemiluminescent substrate for detection of horseradish peroxidase (GE Healthcare, St Cyr au Mont d'Or, France).

Many target-specific substrates for caspase have been identified, including the DNA repair enzyme, poly (ADP-ribose) polymerase (PARP). Western blot detection of PARP cleavage has been used extensively as an indicator of apoptosis. PARP is cleaved between Asp213 and Gly 214 in the human sequence, producing two fragments of apparent molecular weights of 24 and 89 kDa. From H4 cells treated with the MAb combination mDR5-01 and mDR5-05, the fragments of cleaved PARP were detected, whereas no similar effect was observed from the untreated cells or treated with the MAb combination mDR5-05 an mDR5-04, (FIG. 10).

Figure 11:
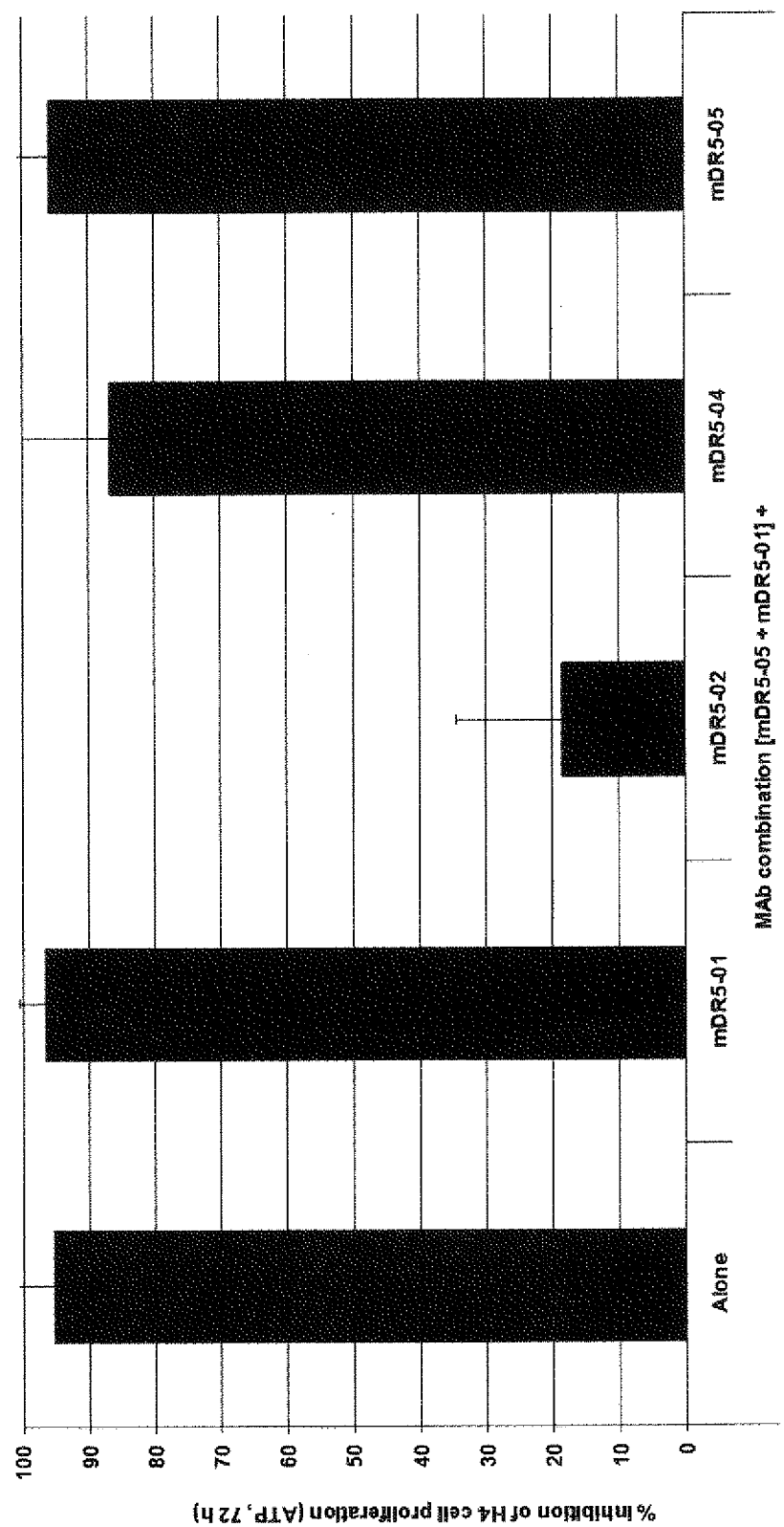
FIG. 11 is a bar diagram showing percent (%) of the cell proliferation inhibition (ATP bioluminescent bioassay, 72 hours) with the selective anti-DR5 agonistic antibody combination (10 µg/mL mDR5-05+0.1 µg/mL mDR5-01), in the presence or not of anti-DR5 MAb (mDR5-01, mDR5-02, mDR5-04 or mDR5-05, 1 µg/mL) using H4 cells ($5 \cdot 10^4$ cells/mL), (mean+/−SD, n=2).

As shown in FIG. 11, the MAb mDR5-02 (1 µg/mL) blocked apoptosis triggered with the MAb combination mDR5-01 and mDR5-05 tested at the ratio 1/100 (10 µg/mL+0.1 µg/mL). No significant impact was observed with the other anti-DR5 MAbs (mDR5-01, mDR5-04 or mDR5-05). Cell viability was evaluated based on quantification of the ATP present, an indicator of metabolically active cells.

Figure 12:
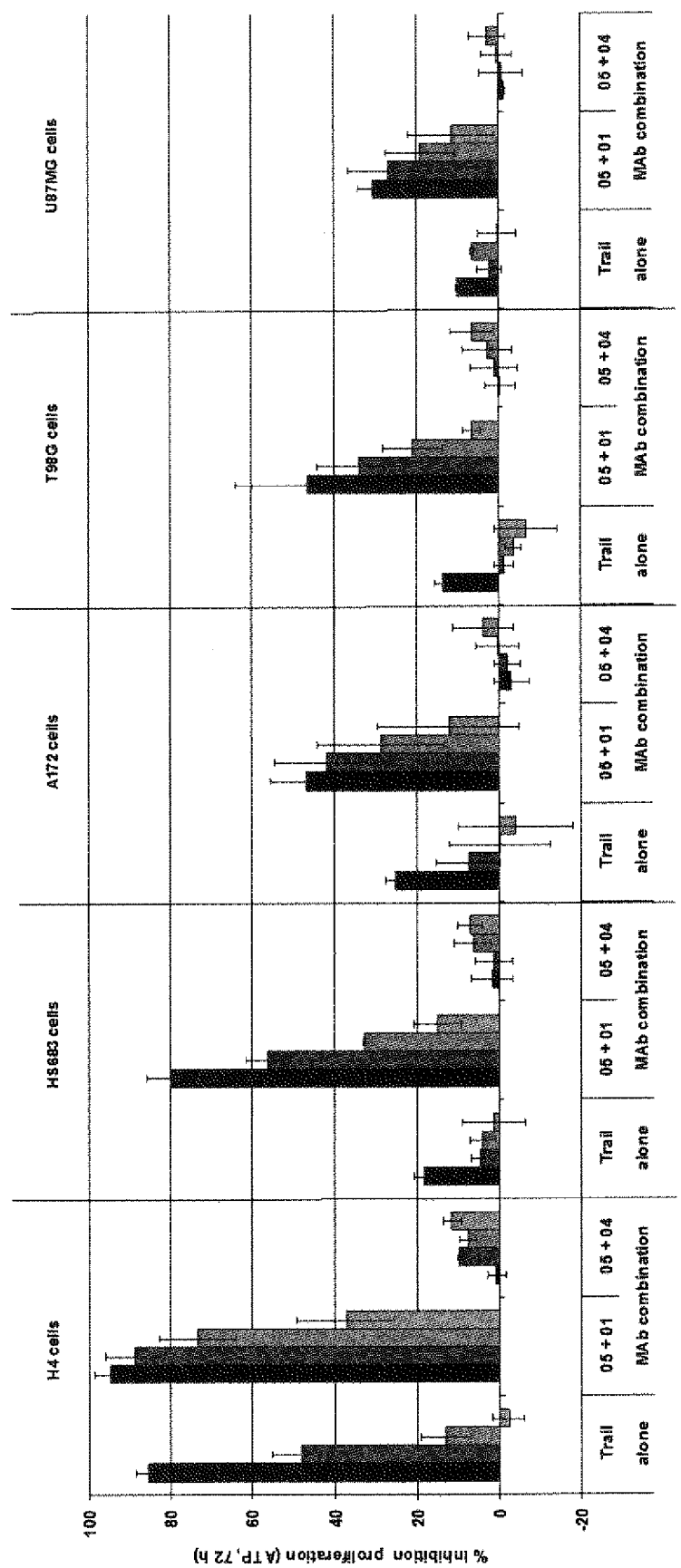
FIG. 12 is a bar diagram showing percent (%) of the cell proliferation inhibition (ATP bioluminescent bioassay, 72 hours) of selective antibody anti-DR5 agonistic antibody combination (10 µg/mL mDR5-05+0.1 µg/mL mDR5-01) and then diluted at ½ compared to TRAIL (20 ng/mL) and then diluted at ½ using H4, HS683, A172, T98G or U87MG glioma cells ($5 \cdot 10^4$ cells/mL), (mean+/−SD, n=2).

The susceptibility of five of the glioma cell lines, H4, HS683, A172, T98G and U87MG to TRAIL or anti-DR5 MAb combination (mDR5-01+mDR5-05 versus mDR5-05+mDR5-04) tested at the ratio 1/100 (10 µg/mL+0.1 µg/mL) were evaluated based on quantification of the ATP present, an indicator of metabolically active cells (FIG. 12). Whereas four cell lines (HS683, A172, T98G and U87MG) are resistant or very low sensitive to TRAIL-induced apoptosis, the use of the MAb anti-DR5 combination mDR5-01 and mDR5-05 bypass this regulatory mechanism.

Figure 14:
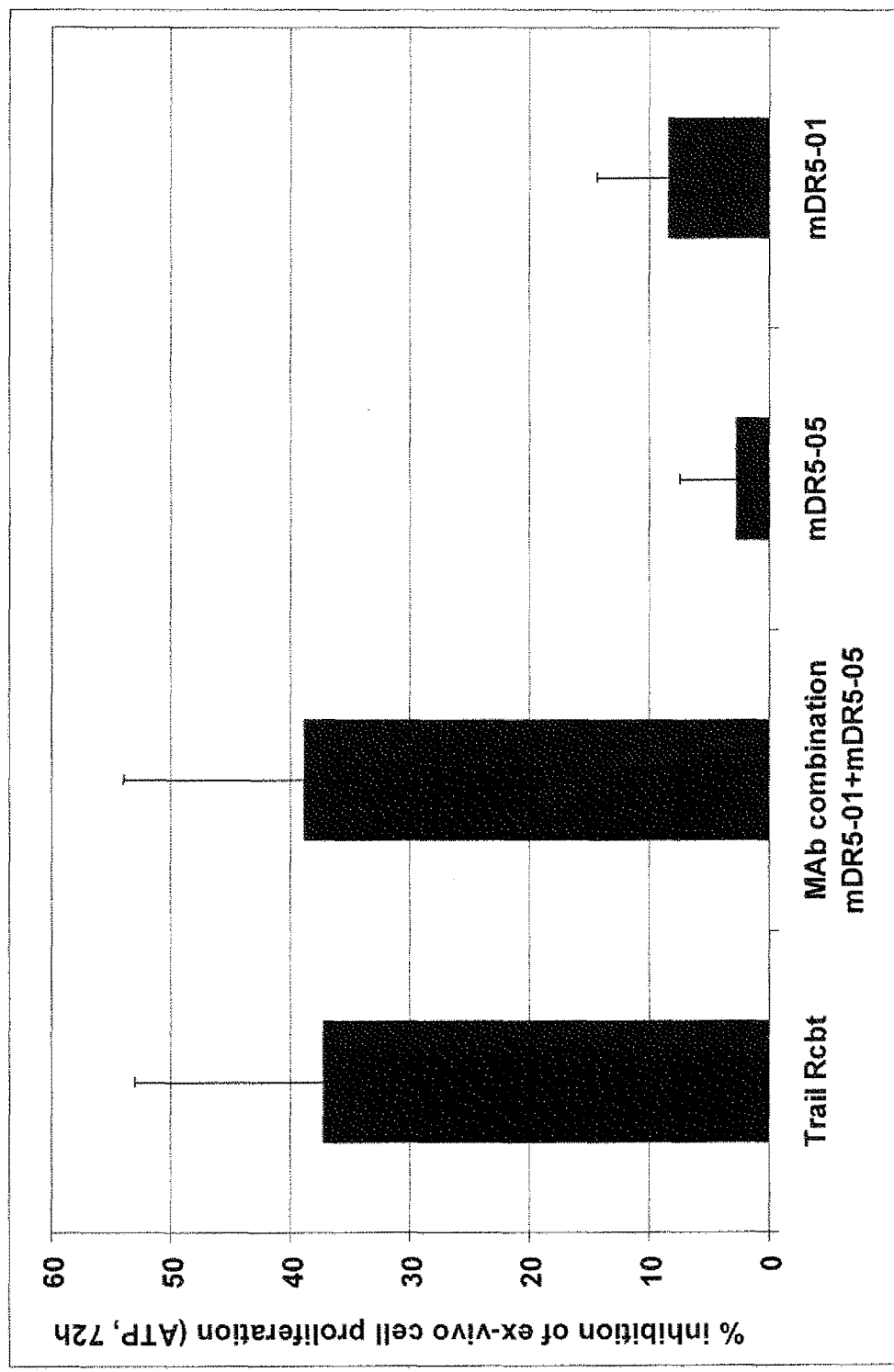
FIG. 14 is a bar diagram showing percent (%) of the cell proliferation inhibition (ATP bioluminescent bioassay, 72 hours) of anti-DR5 antibody alone or combined tested at 10 µg/mL (ratio 1/10) as compared to TRAIL (50 ng/mL) using ex-vivo human glioma cells ($5 \cdot 10^4$ cells/mL), (mean+/−SD, n=3 from three independent ex vivo GBM cells).
Figure 15:
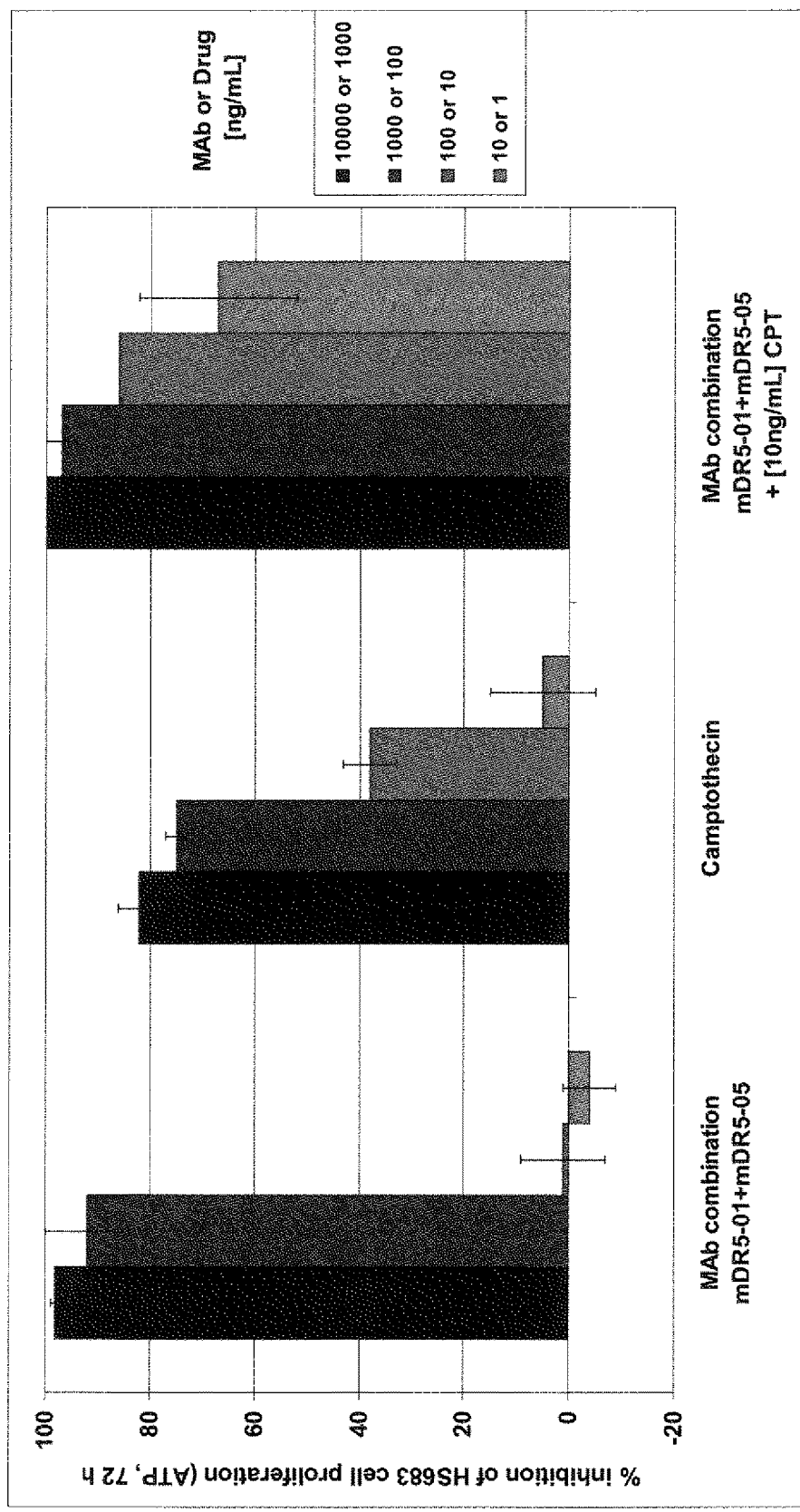
FIGS. 15-18 are bar diagrams showing percent (%) of the cell proliferation inhibition (ATP bioluminescent bioassay, 72 hours) in the presence of mouse anti-DR5 antibody combined tested at 10 µg/mL diluted at 1/10, in the presence of drug alone (1 µg/mL diluted at 1/10) or in association mouse anti-DR5 antibody combined and drug using HS683, A172, 42MGBA or T98G glioma cells, ($5 \cdot 10^4$ cells/mL), (mean+/−SD, n=2), (Campothecin (CPT)).
Figure 16:
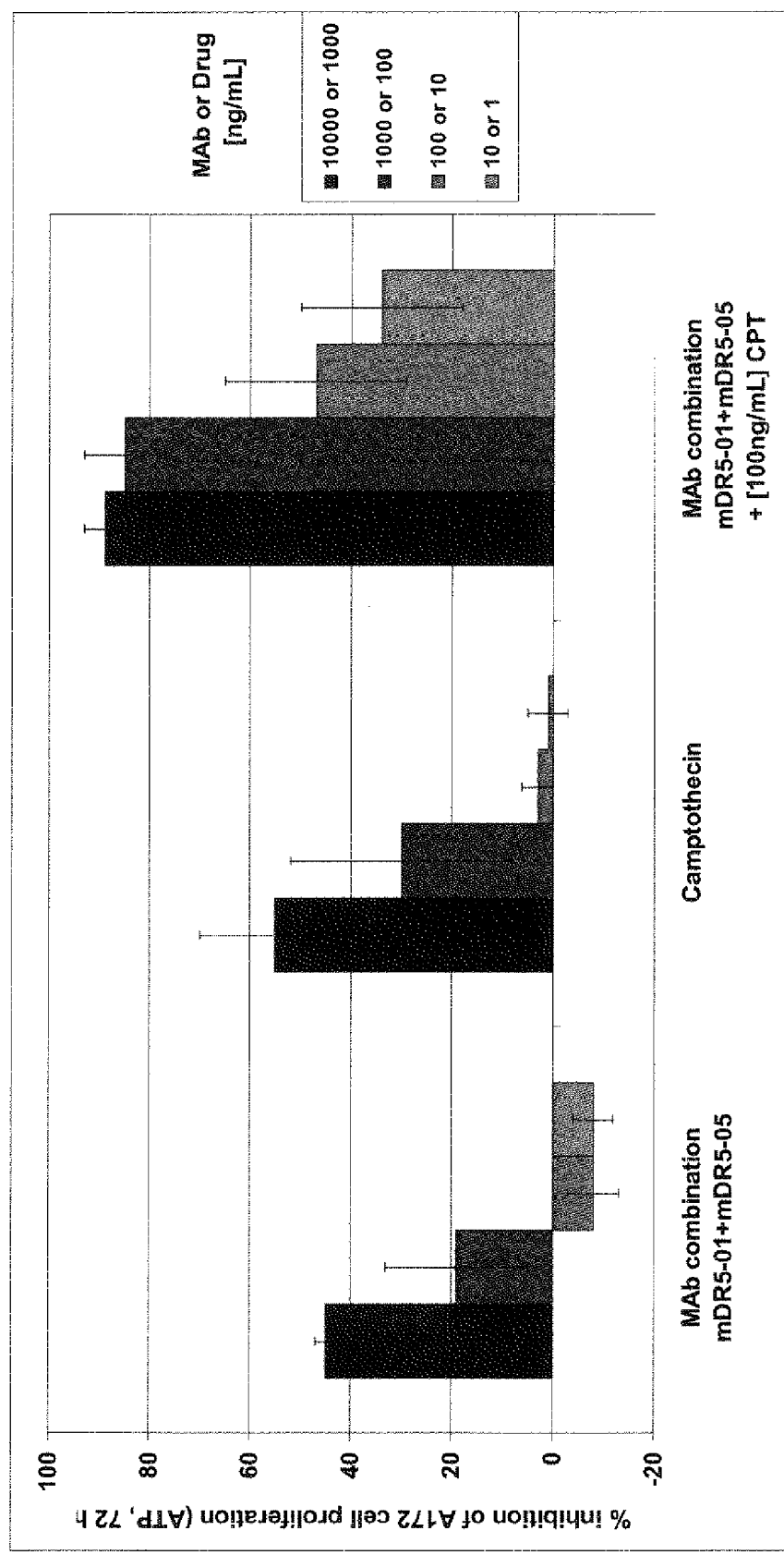
Figure 17:
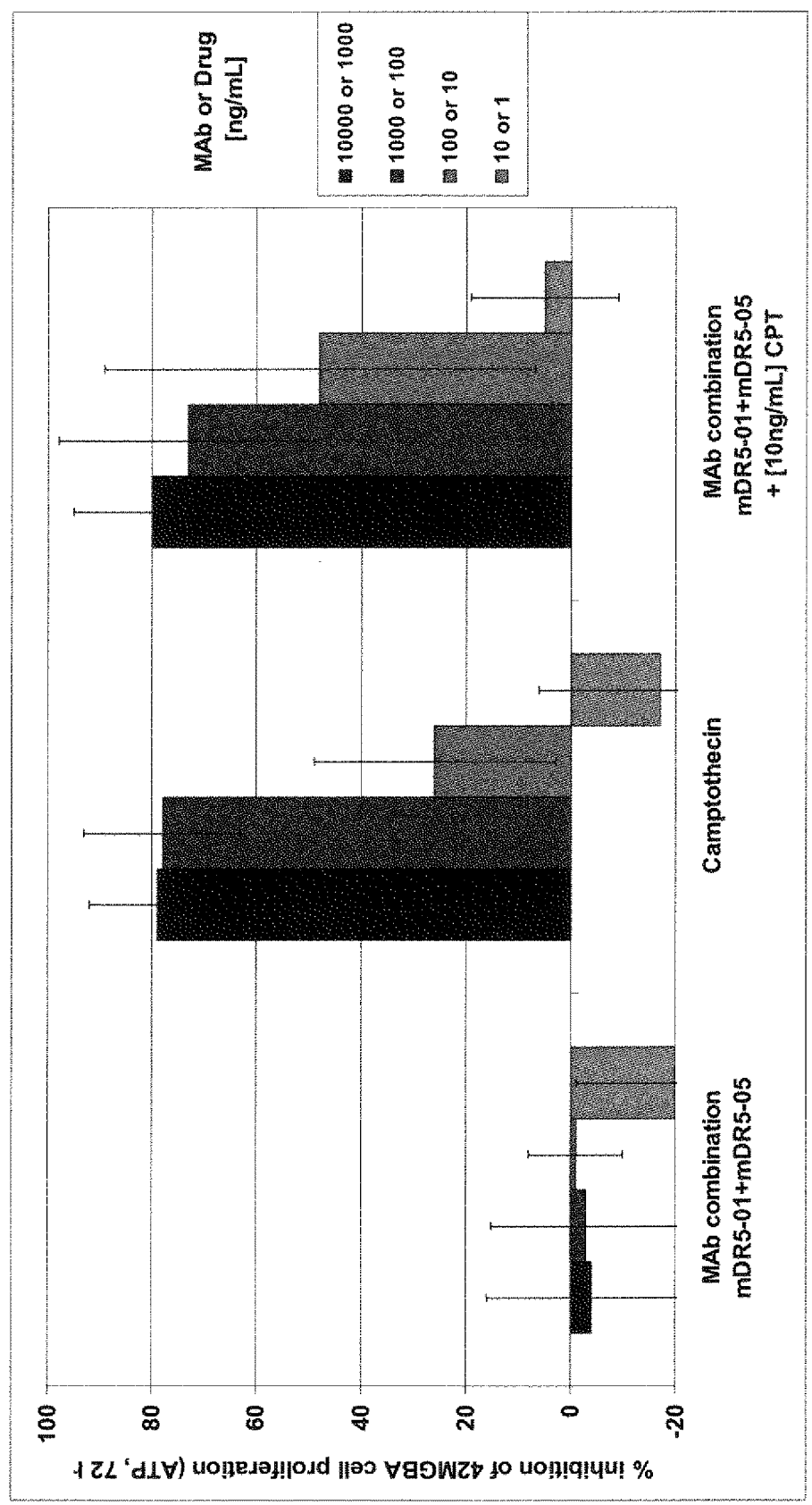
Figure 18:
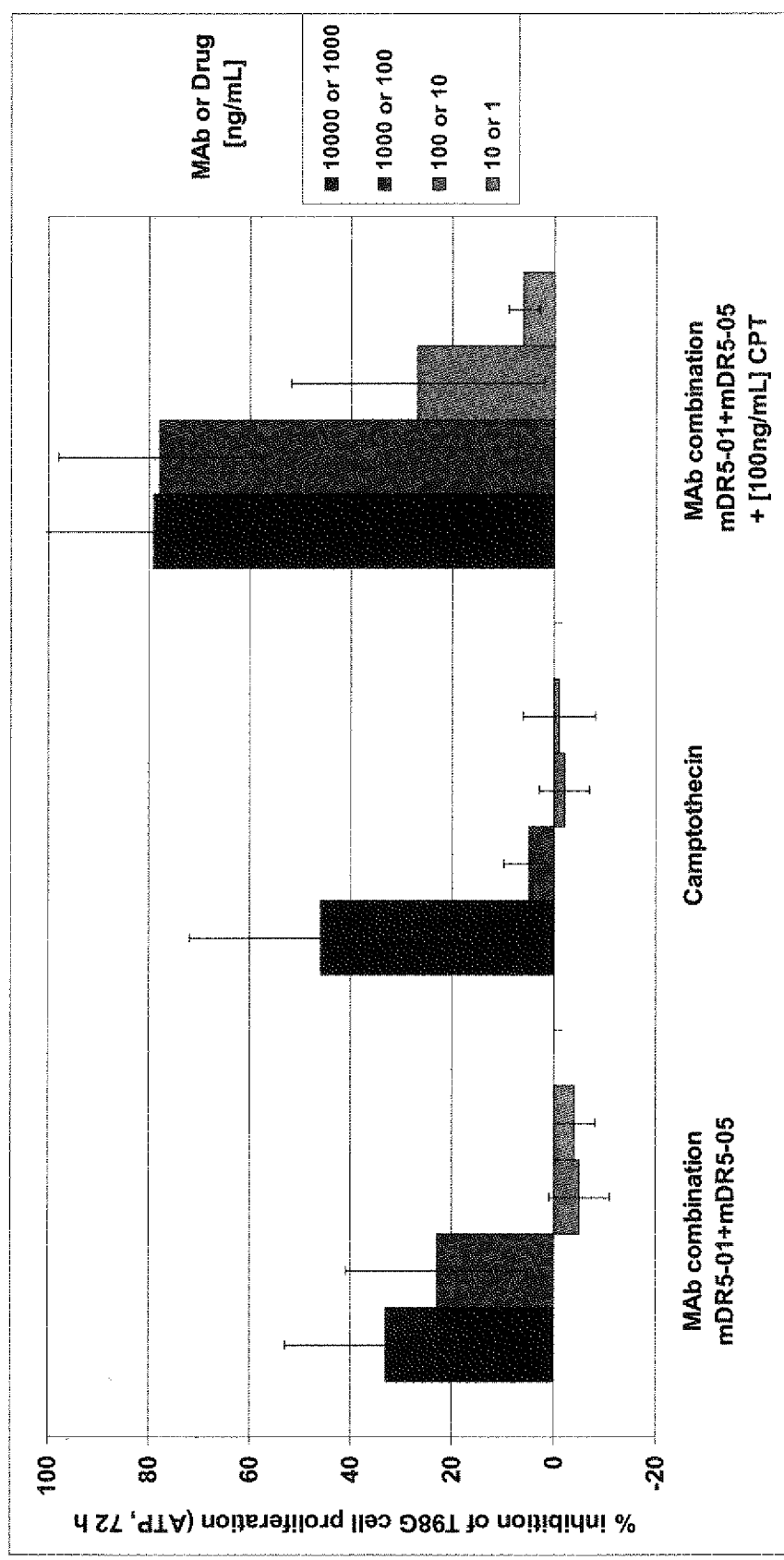
Figure 19:
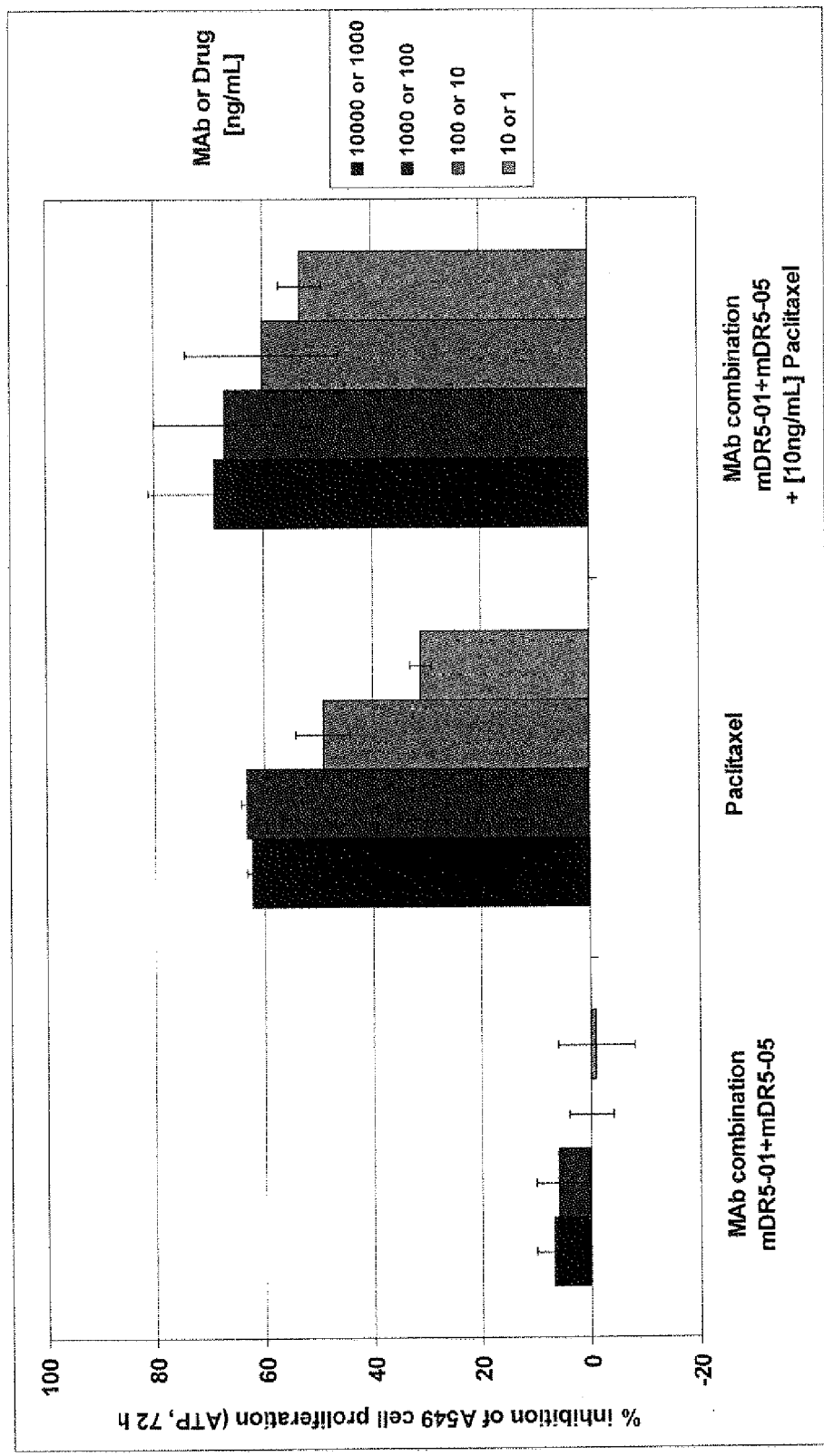
FIGS. 19-22 are bar diagrams showing percent (%) of the cell proliferation inhibition (ATP bioluminescent bioassay, 72 hours) in the presence of mouse anti-DR5 antibody combined tested at 10 µg/mL diluted at 1/10, in the presence of drug alone (1 µg/mL diluted at 1/10) or in association mouse anti-DR5 antibody combined and drug using human breast cell lines (MCF7, MDAMB231) or human lung adenocarcinoma cell lines (NCIH1703, A549), ($5 \cdot 10^4$ cells/mL), (mean+/−SD, n=2).
Figure 20:
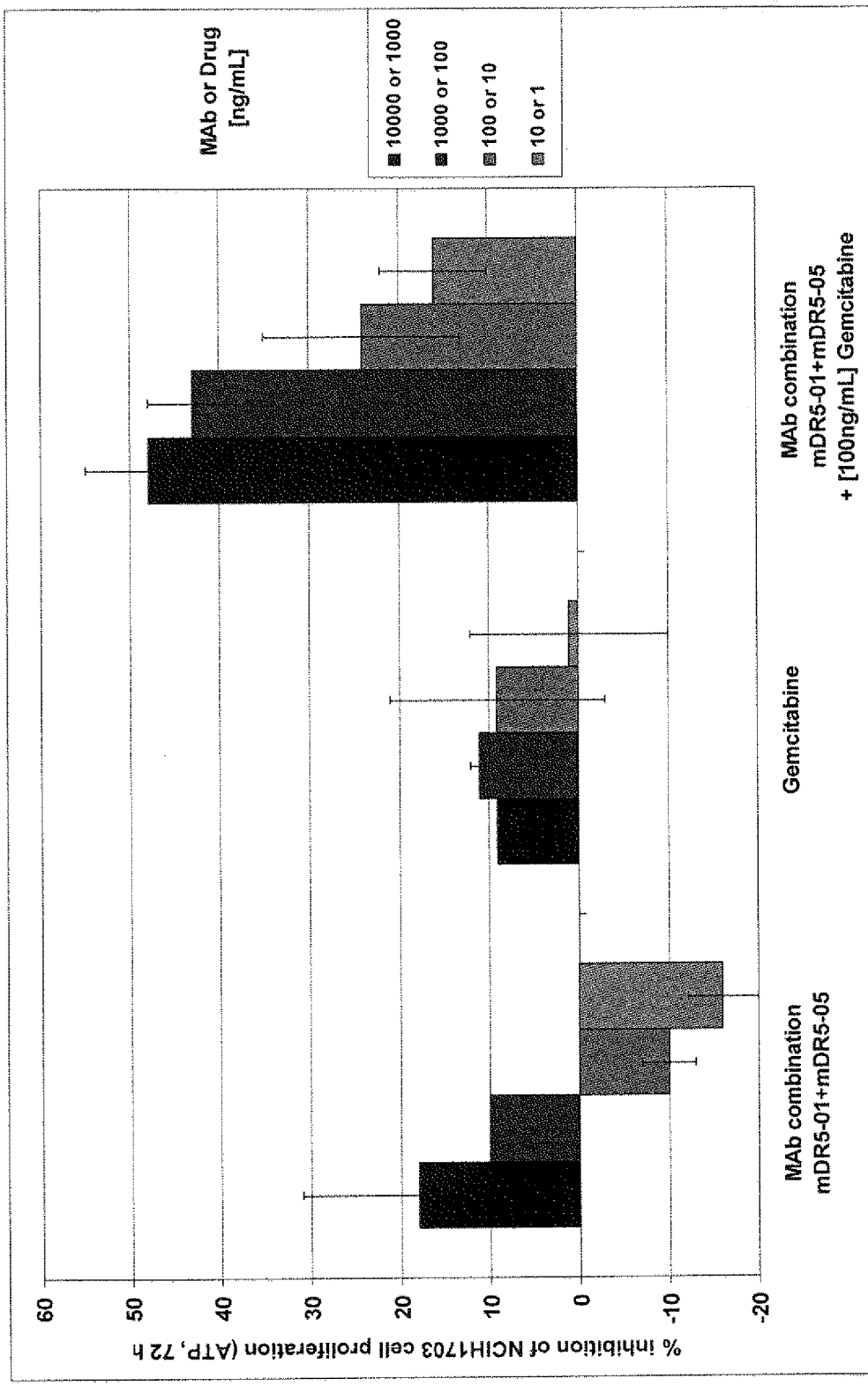
Figure 21:
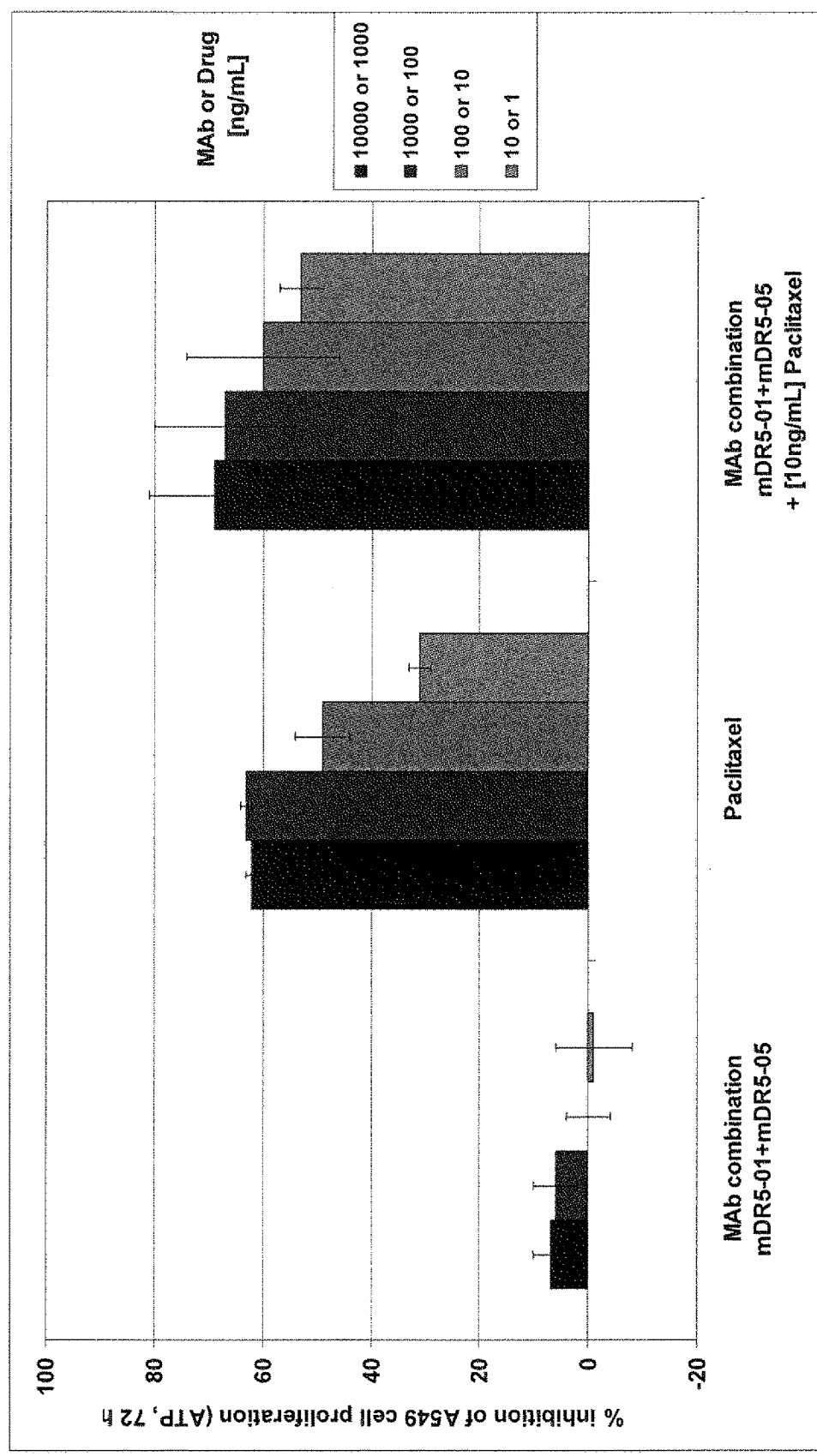
Figure 22:
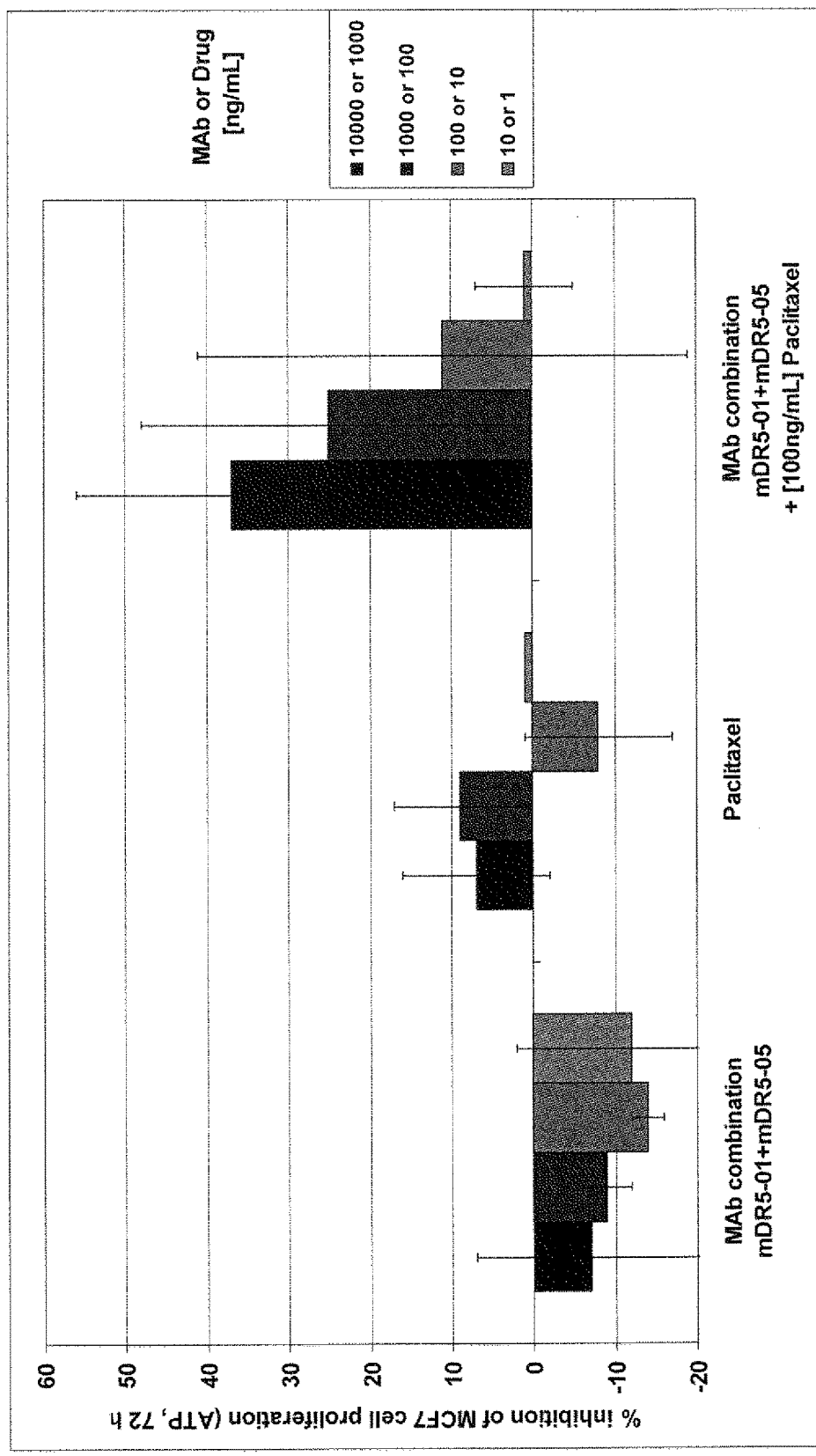

The susceptibility of ex vivo glioma cells from patients to mouse anti-DR5 MAb combination (mDR5-01+mDR5-05) tested at 10 µg/mL (ratio 1/10) were evaluated based on quantification of the ATP present, an indicator of metabolically active cells (FIG. 14).

The susceptibility of four glioma cell lines, (HS683, A172, 42MGBA, T98G) to mouse anti-DR5 MAb combination (mDR5-01+mDR5-05) tested at 10 µg/mL then diluted at 1/10 (ratio 1/1) were evaluated alone or in association with Camptothecin (FIG. 15-18). These cell lines exhibited different levels apoptosis induced with mouse anti-DR5 MAb combination or in the presence of Camptothecin. The use of MAb anti-DR5 combination in association with Camptothecin bypassed this regulatory mechanism and enhanced the level of apoptosis.

The susceptibility of other solid tumor cell lines expressing DR5 such as on human breast adenocarcinoma cell lines (MCF7, MDAMB231) and on human lung adenocarcinoma cell lines (NCIH1703, A549) to mouse anti-DR5 MAb combination (mDR5-01+mDR5-05) tested at 10 µg/mL then diluted at 1/10 (ratio 1/1) were evaluated alone or in association with Paclitaxel, Gemcitabine or Doxorobucine (FIG. 19-22). These cell lines exhibited different levels apoptosis induced with mouse anti-DR5 MAb combination or in the presence of the different drugs tested. The use of MAb anti-DR5 combination in association with these drugs bypassed this regulatory mechanism and enhanced the level of apoptosis.

Example 4

Preparation of Chimeric Monoclonal Antibodies Directed Against DR5

DNA encoding the monoclonal antibodies is readily isolated and sequenced using conventional procedures (e.g. by using oligonucleotide probes that are capable of binding specifically to genes encoding the heavy and light chains of murine antibodies). The hybridoma cells serve as a preferred source of such DNA.

Conversion of murine MAb to native chimeric MAb: cDNA corresponding to the variable region of the hybridoma was obtained using two approaches. The first approach consists of using PCR with a degenerate N-terminal amino acid related primer set to generate the N-Terminal sequencing product. The second approach consists of using PCR with a degenerate primer set generated by IMGT® primer database and specific primers previously described (Essono et al., *J Immunol Methods.* 2003; 203: 279:251-66, Wang et al., *Mol Immunol.* 1991; 28:1387-97). The sequence of N-terminal variable region was determined by Edman degradation. Total RNA extraction was carried out using the Tri Reagent kit according to the protocol described by the supplier Sigma. The amplified VL and VH fragments were cloned into the TOPO-TA cloning vector (Invitrogen) for sequence analyses by the dideoxytermination method (Sanger et al., *Nature.* 1977; 265:687-95). Then antibody variant constructs were amplified by PCR and cloned into the expression vector.

Positions are numbered according to IMGT® and to Kabat® index (Identical V region amino acid sequences and segments of sequences in antibodies of different specificities). Relative contributions of VH and VL genes, minigenes, and complementarity-determining regions to binding of antibody-combining sites were analyzed (Kabat et al., *NIH Publ.* 1991; No. 91-3242, Vol. 1, 647-669).

Figure 13:
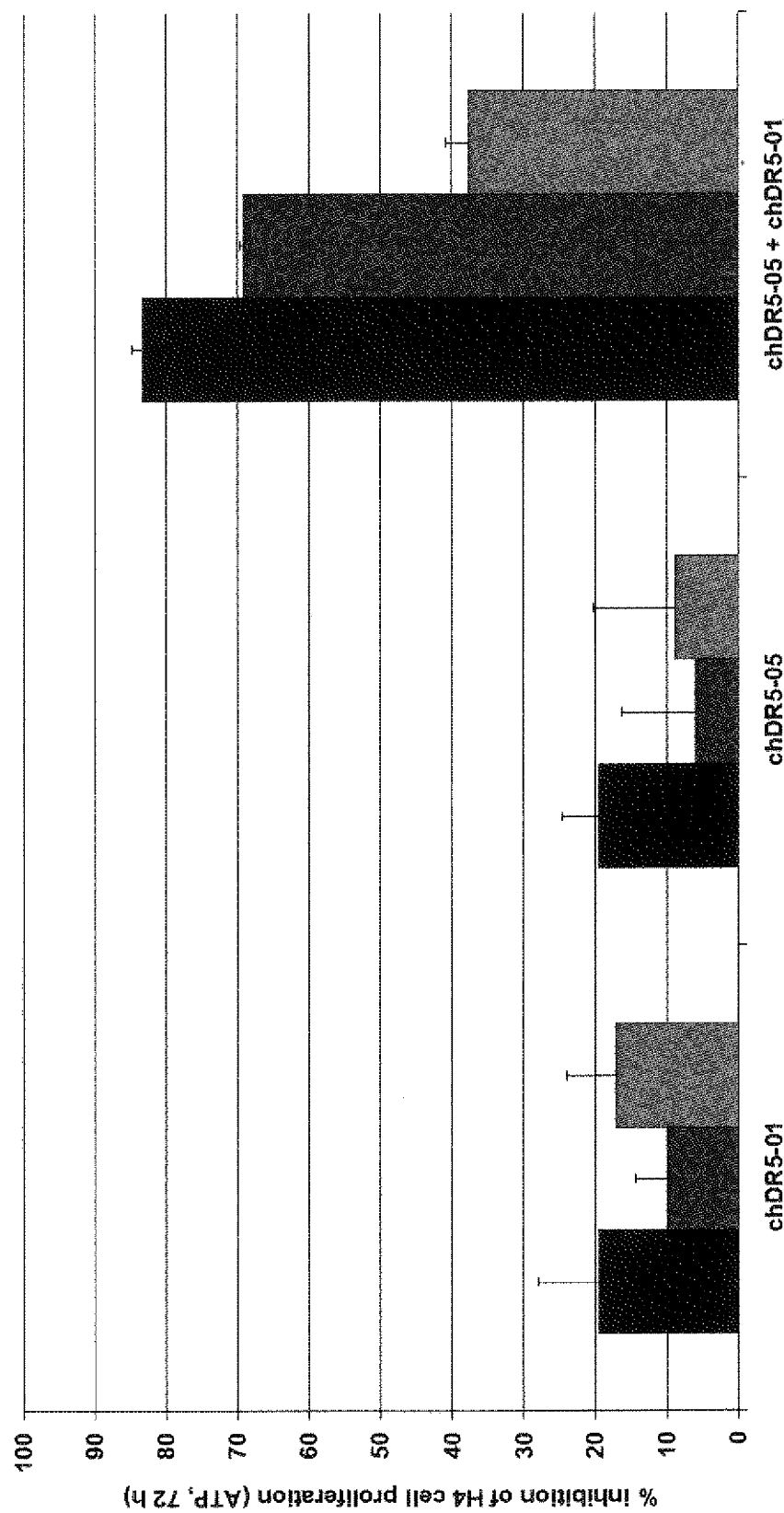
FIG. 13 is a bar diagram showing percent (%) of the proliferation inhibition (ATP bioluminescent bioassay, 72 hours) of chimeric antibody (chDR5-01 or chDR5-05 MAb) tested alone at 5 µg/mL then diluted at ½ versus antibody combination (5 µg/mL chDR5-05+0.05 µg/mL chDR5-01) then diluted at ½ using glioma H4 cells ($5 \cdot 10^4$ cells/mL), (mean+/−SD, n=2).

As shown in FIG. 13, the chimeric MAb combination chDR5-01 and chDR5-05 triggered H4 cell apoptosis tested at the ratio 1/100 (5 µg/mL+0.05 µg/mL). No significant MAb impact was observed with the chimeric MAb tested alone. Cell viability was evaluated based on quantification of the ATP present, an indicator of metabolically active cells.

The nucleic acid sequence or amino acid sequence regarding on the chimeric MAbs DR5-01 and DR5-05 are shown in the Sequence Listing:
nucleotide sequence of the variable murine light chain of DR5-01 antibody anti-DR5 (SEQ ID NO:1) and its derived amino acid sequence (SEQ ID NO:2).
nucleotide sequence of the variable murine heavy chain of DR5-01 antibody anti-DR5 (SEQ ID NO:3) and its derived amino acid sequence (SEQ ID NO:4).
nucleotide sequence of the variable murine light chain of DR5-05 antibody anti-DR5 (SEQ ID NO:5) and its derived amino acid sequence (SEQ ID NO:6).
nucleotide sequence of the variable murine heavy chain of DR5-05 antibody anti-DR5 (SEQ ID NO:7) and its derived amino acid sequence (SEQ ID NO:8).
nucleotide sequence of the constant human heavy chain of DR5-01 or DR5-05 antibody anti-DR5 (SEQ ID NO:9) and its derived amino acid sequence (SEQ ID NO:10).
nucleotide sequence of the constant human light chain of DR5-01 or DR5-05 antibody anti-DR5 (SEQ ID NO:11) and its derived amino acid sequence (SEQ ID NO:12).

Example 5

MAb Production and Protein A Purification

Mammalian cells are the preferred hosts for production of therapeutic glycoproteins, due to their capability to glycosylate proteins in the most compatible form for human applications (Jenkins et al., *Nat Biotech.* 1996; 14:975-81). Mammalian host cells that could be used include, human Hela, 283, H9 and Jurkat cells, mouse NIH3T3 and C127 cells, Cos 1, Cos 7 and CV1 African green monkey cells, quail QC1-3 cells, mouse L cells and Chinese hamster ovary cells. Bacteria very rarely glycosylates proteins, and like other type of common hosts, such as yeasts, filamentous fungi, insect and plant cells yield glycosylation patterns associated with rapid clearance from the blood stream.

The Chinese hamster ovary (CHO) cells allow consistent generation of genetically stable, highly productive clonal cell lines. They can be cultured to high densities in simple bioreactors using serum-free media, and permit the development of safe and reproducible bioprocesses. Other commonly used animal cells include baby hamster kidney (BHK) cells, NSO- and SP2/0-mouse myeloma cells. Production from transgenic animals has also been tested (Jenkins et al., *Nat Biotech.* 1996; 14:975-81).

A typical mammalian expression vector contains the promoter element (early and late promoters from SV40, the long terminal repeats (LTRs) from Retroviruses e.g. RSV, HTLV1, HIV1 and the early promoter of the cytomegalovirus (mCMV, hCMV), which mediates the initiation of transcription of mRNA, the protein coding sequence, and signals required for the termination of transcription and polyadenylation of the transcript (BGH polyA, Herpes thimidine kinase gene of Herpes simplex virus polyA (TKpa), Late SV40 polyA and 3' UTR_Beta_Globin_polyA). Additional elements include enhancers (Eµ, hIE1), Kozak sequences, signal peptide and intervening sequences flanked by donor and acceptor sites for RNA splicing. Suitable expression vectors for use in practise in practising the present invention include, for examples, vectors such as pcDNA3.1, pcDNA3.3, pOptiVEC, pRSV, pEµMCMV, pMCMVHE-UTR-BG, pHCMVHE-UTR-BG, pMCMV-UTR-BG, pHCMV-UTR-BG, pMCMVHE-5V40, pHCMVHE-5V40, pMCMV-5V40, pHCMV-5V40, pMCMVHE-TK, pHCMVHE-TK, pMCMV-TK, pHCMV-TK, pMCMVHE-BGH, pHCMVHE-BGH, pMCMV-BGH, pHCMV-UTR-BGH).

The empty CHO Easy C cells (purchased by the CCT collection) were co-transfected with MAb expression vector for light and heavy chains following transient or stable transfection procedure established in our laboratory. Secretion of H and L chains were enabled by the respective human IgH leader sequence. The coding regions for light and heavy chains of MAb anti-DR5 are introduced into the MAb expression vector in the multiple cloning site. The transformants are analyzed for correct orientation and reading frame, the expression vector may be transfected into CHO cell line.

Protein A chromatography from murine ascitic fluid. The murine ascitic fluid is adjusted at pH 8.3 with the equilibration buffer 0.1 M Tris and 1.5 M Sulfate Ammonium and then loaded onto the rProtein A Sepharose Fast Flow column (GE Healthcare, Saint Cyr au Mont d'or, France). The non binding proteins are flowed through and removed by several washings with equilibration buffer. The MAb anti-DR5 is eluted off the Protein A column using the elution buffer 0.1 M Citrate Sodium at pH 3.5. Column eluent is monitored by A280. The anti-DR5 MAb peak is pooled.

Protein A chromatography from harvested CHO cell culture fluid. The harvested cell culture fluid produced from CHO cells is loaded onto the Hi Trap rProtein A column (GE Healthcare, Saint Cyr au Mont d'Or, France) that is equilibrated with Phosphate buffered saline, pH 7.2. The non binding proteins are flowed through and removed by several washings with PBS buffer followed. The MAb anti-DR5 is eluted off the Protein A column using a step of elution of 0.1 M Citric acid at pH 3.0. Column eluent is monitored by A280. The anti-DR5 MAb peak is pooled.

Example 6

Preparation of Humanized Monoclonal Antibodies Directed Against DR5

Antibody CDR and FR regions have been determined according to various numbering approaches such as IMGT (ImMunoGeneTics Information System® http://imgt.cines.fr), Kabat or Common Numbering System. However, IMGT determined CDRs for a given antibody are not necessarily identical to the CDRs defined by the other numbering systems. The variable domain CDRs and framework regions have been identified by the inventor thanks to IMGT numbering systems.

Conversion of chimeric MAb to Humanized MAb: Humanized DR5 antibody H and L chain was generated using CDR-grafting by the PCR method. In order to generate a humanized antibody in which the CDRs of a mouse monoclonal antibody is grafted onto a human antibody, there is preferably a high homology between the variable region of a mouse monoclonal antibody and the variable region of a human antibody. Thus, the H chain and L chain V regions of a mouse anti-human DR5 monoclonal antibody are compared to the V region of all known human antibodies using the software IMGT/DomainGapAlign. When a mouse antibody is humanized by a conventional technology, the amino acid sequence of some of the V region FRs of a mouse antibody supporting the CDR may be grafted onto the FR of a human V region, as desired.

For both of the humanized H chain and L chain V regions, it is possible to select the L and H chain V regions and J region, IGKV3-D-15*01, IGHV1-3*01, IGKJ2*01 and IGHJ4*01 respectively, having a high homology with the H and L chain V region and J region of the mDR5 antibody and IGKV1-16*01, IGHV1-3*01, IGKJ4*01 and IGHJ4*01, having a high homology with the H and L chain V region and J region of the mDR5-05 antibody.

After sequence of the Humanized variable region of HzDR5-01 and HzDR5-05 is determined. The variables regions of H and L of HzDR5-01 and Hz-DR5-05 were amplified by PCR and cloned into the expression vector p3U containing the human IgG1 constant region.

In the case of human CDR-grafted antibodies, the binding activity is decreased by grafting of the amino acid sequence of CDR in the mouse antibody alone. In order to avoid this reduction, among the amino acid residues in FR different between a human antibody and a mouse antibody, amino acid residues considered to have influences on the binding activity are grafted together with the amino acid sequence of CDR. Accordingly, an attempt was also made in this example to identify the amino acid residues in FR considered to have influences on the binding activity.

Figure 23:
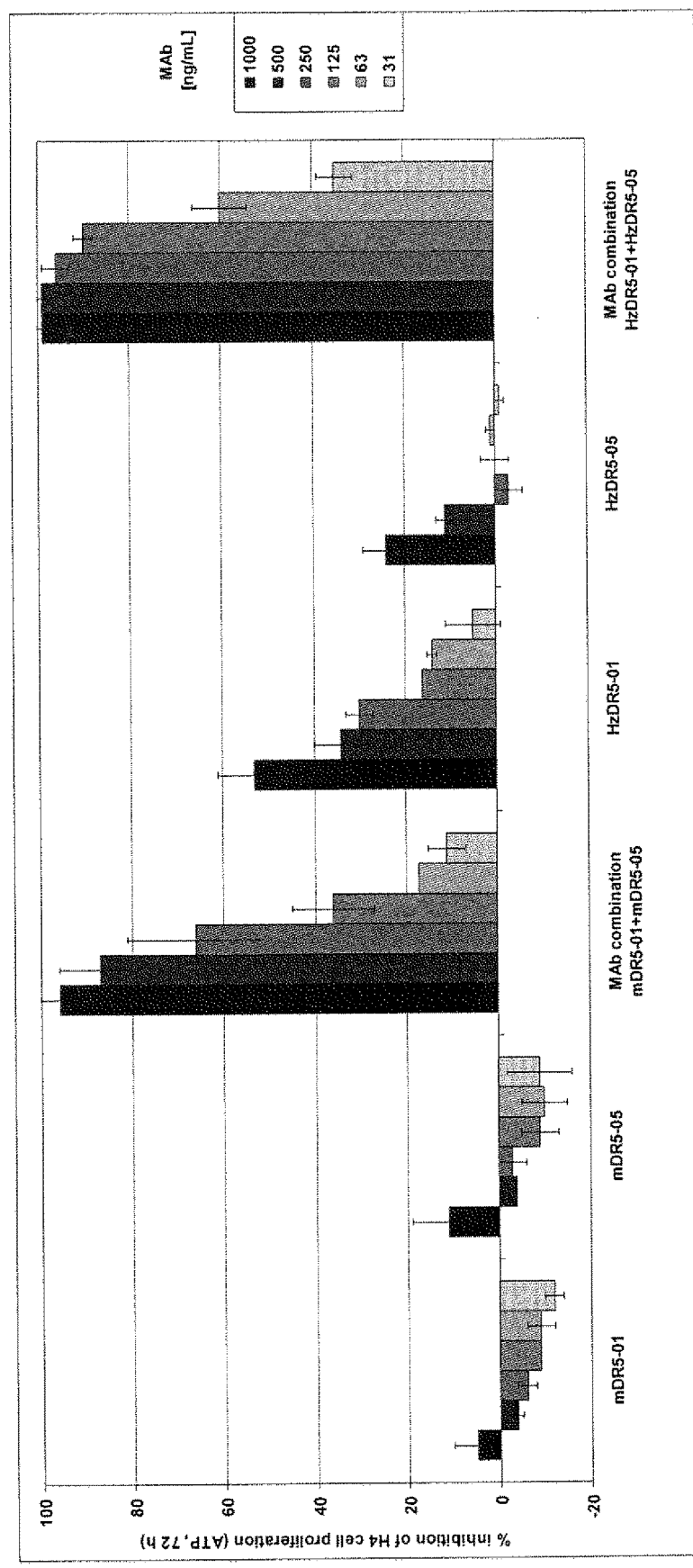
FIG. 23 is a bar diagram showing percent (%) of the cell proliferation inhibition (ATP bioluminescent bioassay, 72 hours) of mouse anti-DR5 antibody alone or combined as compared to humanized anti-DR5 antibody alone or combined tested at 1 µg/mL (ratio 1/1 in combined) then diluted at 1/2 using H4 glioma cells cells ($5 \cdot 10^4$ cells/mL), (mean+/−SD, n=2).

The susceptibility of the glioma cell line H4 to mouse or humanized anti-DR5 MAb combination (mDR5-01+mDR5-05) tested at 1 µg/mL then diluted at 1/2 (ratio 1/1) were evaluated based on quantification of the ATP present, an indicator of metabolically active cells (FIG. 23). The humanized MAb combination (hzDR5-01 and hzDR5-05) triggered cell apoptosis at a higher level compared to the mouse MAb combination (mDR5-01 and mDR5-05).

Example 7

In Vivo Biologic MAb Activity

Figure 24:
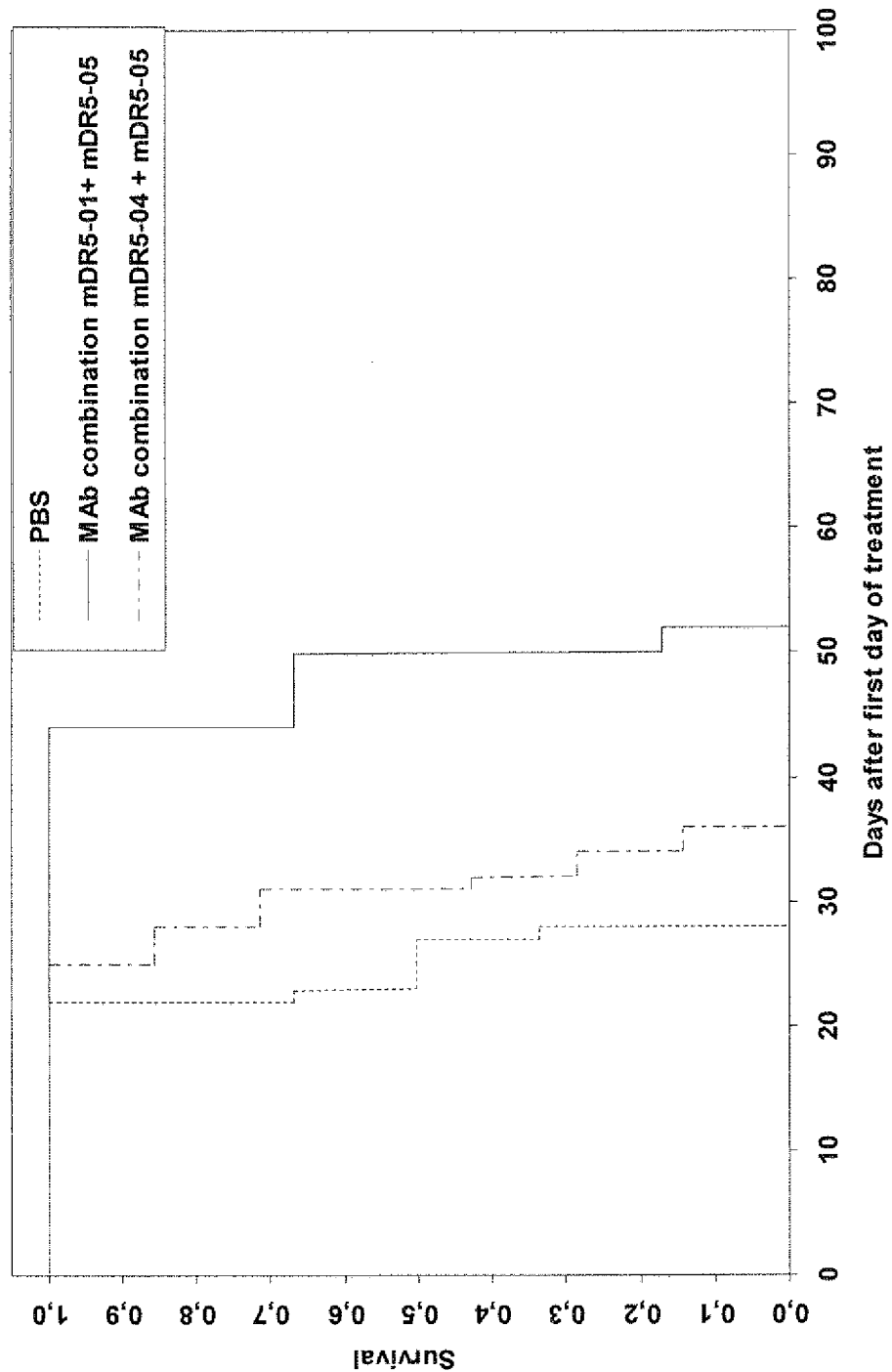
FIG. 24 is a survival curve of nude mice orthotopic engrafted with SC2 human glioma treated with or without mouse anti-DR5 antibody combined. MAb treatment was administrated by intraperitoneal injection (IP) at 5 mg/kg per mouse until mice euthanasia due to loss of weight and was applied during 36 days maximum. Survival times obtained with control group were compared to survival times obtained with treated groups (mDR5-01+mDR5-05 versus mDR5-04+mDR5-05) using Kaplan Meier method and Wilcoxon statistical test (JMP software).

Orthotopic human glioma xenograft mouse model was obtained by intracerebral injection in nude mouse of 100 000 isolated cell coming from heterotypic human glioma xenograft mouse model Sc2. MAb treatment was administrated by intraperitoneal injection (IP) at 5 mg/kg per mouse until mice euthanasia due to loss of weight and was applied during 36 days maximum. Survival times obtained with control group were compared to survival times obtained with treated groups (mDR5-01+mDR5-05 versus mDR5-04+mDR5-05) using Kaplan Meier method and Wilcoxon statistical test (JMP software), (FIG. 24). This study demonstrated anti-tumor activity of mouse anti-DR5 MAb combination (mDR5-01+mDR5-05) on intracerebral glioma.

The invention claimed is:

1. A composition comprising at least one or two polypeptides binding specifically a DR5 receptor, wherein the at least one or two polypeptides comprise two immunoglobulin binding domains comprising:
- a first binding domain comprising a pair of VH and VL chains wherein the VH chain contains a CDR1 of sequence SEQ ID NO: 13, a CDR2 of sequence SEQ ID NO: 14, a CDR3 of sequence SEQ ID NO: 15; and the VL chain contains a CDR1 of sequence SEQ ID NO: 16, a CDR2 of amino acid sequence FAS, a CDR3 of sequence SEQ ID NO: 17, and
- a second binding domain comprising a pair of VH and VL chains wherein the VH chain contains a CDR1 of sequence SEQ ID NO: 18, a CDR2 of sequence SEQ ID NO: 14, a CDR3 of sequence SEQ ID NO: 19; and the VL chain contains a CDR1 of sequence SEQ ID NO: 20, a CDR2 of amino acid sequence RTS, a CDR3 of sequence SEQ ID NO: 21, wherein
- the at least one polypeptide comprises both immunoglobulin binding domains; or
- the at least two polypeptides comprise a first polypeptide comprising the first binding domain and a second polypeptide comprising the second binding domain;

and a pharmaceutically carrier, diluent or excipient.

2. The composition of claim 1, comprising:
one or more of amino acid sequence pairs SEQ ID NO: 2 and 4 and SEQ ID NO: 6 and 8,
the pair of amino acid sequences SEQ ID NO: 2 and 4,
the pair of amino acid sequences SEQ ID NO: 6 and 8, or
both amino acid sequence pairs SEQ ID NO: 2 and 4 and SEQ ID NO: 6 and 8; or
one or more of amino acid sequence pairs SEQ ID NO: 35 and 37 and SEQ ID NO: 39 and 41,
the pair of amino acid sequences SEQ ID NO: 35 and 37,
the pair of amino acid sequences SEQ ID NO: 39 and 41, or
both amino acid sequence pairs SEQ ID NO: 35 and 37 and SEQ ID NO: 39 and 41.

3. The composition of claim 1 comprising a bispecific antibody comprising the amino acid sequence pair SEQ ID NO: 2 and 4 and the amino acid sequence pair SEQ ID NO: 6 and 8.

4. The composition of claim 1 comprising a bispecific antibody comprising the amino acid sequence pair SEQ ID NO: 35 and 37 and the amino acid sequence pair SEQ ID NO: 39 and 41.

5. The composition of claim 1, wherein the polypeptide or polypeptides is/are selected from the group of an Fv, an Fab, an F(ab')2, an scFv, and an antibody.

6. The composition of claim 5, wherein the antibody is a monoclonal antibody.

7. The composition of claim 1, wherein the first or second binding domain comprises the amino acid sequence pairs SEQ ID NO:2 and 4, or SEQ ID NO: 35 and 37.

8. The composition of claim 1, wherein the first or second binding domain comprises the amino acid sequence pairs SEQ ID NO: 6 and 8, or SEQ ID NO: 39 and 41.

9. The composition of claim 1, wherein one binding domain comprises the pair of amino acid sequences SEQ ID NO: 2 and 4, and the other binding domain comprises the pair of amino acid sequences SEQ ID NO: 6 and 8.

10. The composition of claim 1, wherein one binding domain comprises the pair of amino acid sequences SEQ ID NO: 35 and 37, and the other binding domain comprises the pair of amino acid sequences SEQ ID NO: 39 and 41.

11. A polypeptide binding specifically a DR5 receptor, comprising one or two binding domains comprising a pair of VH and VL chains wherein the VH chain contains a CDR1 of sequence SEQ ID NO: 13, a CDR2 of sequence SEQ ID NO: 14, a CDR3 of sequence SEQ ID NO: 15; and the VL chain contains a CDR1 of sequence SEQ ID NO: 16, a CDR2 of amino acid sequence FAS, a CDR3 of sequence SEQ ID NO: 17.

12. A polypeptide binding specifically a DR5 receptor, comprising one or two binding domains comprising a pair of VH and VL chains wherein the VH chain contains a CDR1 of sequence SEQ ID NO: 18, a CDR2 of sequence SEQ ID NO: 14, a CDR3 of sequence SEQ ID NO: 19; and the VL chain contains a CDR1 of sequence SEQ ID NO: 20, a CDR2 of amino acid sequence RTS, a CDR3 of sequence SEQ ID NO: 21.

13. A bispecific or multivalent polypeptide binding specifically a DR5 receptor, which comprises:
a first binding domain comprising a pair of VH and VL chains wherein the VH chain contains a CDR1 of sequence SEQ ID NO: 13, a CDR2 of sequence SEQ ID NO: 14 CDR1, a CDR3 of sequence SEQ ID NO: 15; and the VL chain contains a CDR1 of sequence SEQ ID NO: 16, a CDR2 of amino acid sequence FAS, a CDR3 of sequence SEQ ID NO: 17, and
a second binding domain comprising a pair of VH and VL chains wherein the VH chain contains a CDR1 of sequence SEQ ID NO: 18, a CDR2 of sequence SEQ ID NO: 14, a CDR3 of sequence SEQ ID NO: 19; and the VL chain contains a CDR1 of sequence SEQ ID NO: 20, a CDR2 of amino acid sequence RTS, a CDR3 of sequence SEQ ID NO: 21.

14. A composition comprising two polypeptides, or antibodies or fragments thereof, both having the capability to bind to DR5 receptor,
wherein a first polypeptide or antibody or fragment thereof, comprises a first antigen-biding domain comprising a pair of VH and VL chains wherein the VH chain contains a CDR1 of sequence SEQ ID NO: 13, a CDR2 of sequence SEQ ID NO: 14, a CDR3 of sequence SEQ ID NO: 15; and the VL chain contains a CDR1 of sequence SEQ ID NO: 16, a CDR2 of amino acid sequence FAS, a CDR3 of sequence SEQ ID NO: 17, and
wherein a second polypeptide or antibody or fragment thereof, comprises a second antigen-binding domain comprising a pair of VH and VL chains wherein the VH chain contains a CDR1 of sequence SEQ ID NO: 18, a CDR2 of sequence SEQ ID NO: 14, a CDR3 of sequence SEQ ID NO: 19; and the VL chain contains a CDR1 of sequence SEQ ID NO: 20, a CDR2 of amino acid sequence RTS, a CDR3 of sequence SEQ ID NO: 21.

15. A bispecific antibody, or fragment thereof, having the capability to bind to DR5 receptor, said antibody comprising a first antigen-binding domain comprising a pair of VH and VL chains wherein the VH chain contains a CDR1 of sequence SEQ ID NO: 13, a CDR2 of sequence SEQ ID NO: 14, a CDR3 of sequence SEQ ID NO: 15; and the VL chain contains a CDR1 of sequence SEQ ID NO: 16, a CDR2 of amino acid sequence FAS, a CDR3 of sequence SEQ ID NO: 17, and a second antigen-binding domain comprising a pair of VH and VL chains wherein the VH chain contains a CDR1 of sequence SEQ ID NO: 18, a CDR2 of sequence SEQ ID NO: 14, a CDR3 of sequence SEQ ID NO: 19; and the VL chain contains a CDR1 of sequence SEQ ID NO: 20, a CDR2 of amino acid sequence RTS, a CDR3 of sequence SEQ ID NO: 21.

16. A method for treating a mammal having a disease or disorder in which DR5 is expressed, wherein the disease or disorder is selected from the group consisting of cancer, an autoimmune disease, an inflammatory condition, a viral infection, and a viral disease, wherein the method comprises the administration to the mammal of an effective amount of a composition according to claim 1.

17. The method of claim 16, wherein the disease or disorder is a solid cancer.

18. The method of claim 16, wherein the composition comprises at least two polypeptides, and wherein the at least two polypeptides are administered simultaneously, separately, or sequentially to the mammal.

19. The method of claim 16, wherein the mammal is a human.

* * * * *

SEQUENCE LISTING

```
<160> NUMBER OF SEQ ID NOS: 41

<210> SEQ ID NO 1
<211> LENGTH: 321
<212> TYPE: DNA
<213> ORGANISM: Artificial Sequence
<220> FEATURE:
<223> OTHER INFORMATION: Nucleic acid sequence of murine anti-DR5-01
      variable light chain

<400> SEQUENCE: 1
gacattgtgc tgacccagtc tccagccacc ctgtctgtga ctccaggaga tagcgtcagt      60
ctttcctgca gggccagcca aagtattagc aacaacctac actggtatca acaaaaatca    120
```

```
catgagtctc caaggcttct catcaagttt gcttcccagt ccatctctgg gatcccctcc      180
cggttcagtg gcagtggatc aggggcagat ttcactctca ttatcaacag tgtggagact      240
gaagattttg gaatgtattt ctgtcaacag gtaacagct ggccgtacac attcggtgga      300
ggcaccaagc tcgagatcaa a                                                321
```

```
<210> SEQ ID NO 2
<211> LENGTH: 107
<212> TYPE: PRT
<213> ORGANISM: Artificial Sequence
<220> FEATURE:
<223> OTHER INFORMATION: Amino acid sequence of murine anti-DR5-01
      variable light chain

<400> SEQUENCE: 2

Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Ser Ile Ser Asn Asn
            20                  25                  30

Leu His Trp Tyr Gln Gln Lys Ser His Glu Ser Pro Arg Leu Leu Ile
        35                  40                  45

Lys Phe Ala Ser Gln Ser Ile Ser Gly Ile Pro Ser Arg Phe Ser Gly
    50                  55                  60

Ser Gly Ser Gly Ala Asp Phe Thr Leu Ile Ile Asn Ser Val Glu Thr
65                  70                  75                  80

Glu Asp Phe Gly Met Tyr Phe Cys Gln Gln Gly Asn Ser Trp Pro Tyr
                85                  90                  95

Thr Phe Gly Gly Gly Thr Lys Leu Glu Ile Lys
            100                 105
```

```
<210> SEQ ID NO 3
<211> LENGTH: 354
<212> TYPE: DNA
<213> ORGANISM: Artificial Sequence
<220> FEATURE:
<223> OTHER INFORMATION: Nucleic acid sequence of murine anti-DR5-01
      variable heavy chain

<400> SEQUENCE: 3
gaggtccagc tgcagcagtc tggggcagag tttgtgaagc caggggcctc agtcaagttg      60
tcctgcacag cttctggctt caacattaaa gacaccttta cactgggt gaagcagagg       120 cctgaacagg gcctggactg gattggaagg attgatcctg cgaatggtaa tactaaatat      180
gatccgaagt tccagggcaa ggccactgaa acaacagaca tcctccaa cacagcctac       240 ctgcagctca gcagcctgac atctgaggac actgccgtct attattgtgt tagaggacta      300
tatacgtact actttgacta ctgggggccaa ggaacctcgg tcaccgtctc ctca           354
```

```
<210> SEQ ID NO 4
<211> LENGTH: 118
<212> TYPE: PRT
<213> ORGANISM: Artificial Sequence
<220> FEATURE:
<223> OTHER INFORMATION: Amino acid sequence of murine anti-DR5-01
      variable heavy chain

<400> SEQUENCE: 4

Glu Val Gln Leu Gln Gln Ser Gly Ala Glu Phe Val Lys Pro Gly Ala
1               5                   10                  15

Ser Val Lys Leu Ser Cys Thr Ala Ser Gly Phe Asn Ile Lys Asp Thr
```

```
                20                  25                  30
Phe Ile His Trp Val Lys Gln Arg Pro Glu Gln Gly Leu Asp Trp Ile
            35                  40                  45

Gly Arg Ile Asp Pro Ala Asn Gly Asn Thr Lys Tyr Asp Pro Lys Phe
        50                  55                  60

Gln Gly Lys Ala Thr Glu Thr Thr Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Val Arg Gly Leu Tyr Thr Tyr Tyr Phe Asp Tyr Trp Gly Gln Gly Thr
            100                 105                 110

Ser Val Thr Val Ser Ser
        115

<210> SEQ ID NO 5
<211> LENGTH: 318
<212> TYPE: DNA
<213> ORGANISM: Artificial Sequence
<220> FEATURE:
<223> OTHER INFORMATION: Nucleic acid sequence of murine anti-DR5-05
      variable light chain

<400> SEQUENCE: 5
gacattcagc tgacccagtc tccagcaatc atgtctgcat ctccagggga gaaggtcacc       60
atatcctgca gtgccagttc aagtgtaagt tacatgtact ggtaccagca gaagccagga      120
tcctccccca aaccctggat ttatcgcaca tccaacctgg cttctggagt ccctggtcgc      180
ttcagtggca gtgggtctgg gacctcttac tctctcacaa tcagcagcat ggaggctgaa      240
gatgctgcca cttattactg ccagcagtat catagttacc cacctacatt cggtggaggc      300
accaagctcg agatcaaa                                                    318

<210> SEQ ID NO 6
<211> LENGTH: 106
<212> TYPE: PRT
<213> ORGANISM: Artificial Sequence
<220> FEATURE:
<223> OTHER INFORMATION: Amino acid sequence of murine anti-DR5-05
      variable light chain

<400> SEQUENCE: 6

Asp Ile Gln Leu Thr Gln Ser Pro Ala Ile Met Ser Ala Ser Pro Gly
1               5                   10                  15

Glu Lys Val Thr Ile Ser Cys Ser Ala Ser Ser Val Ser Tyr Met
            20                  25                  30

Tyr Trp Tyr Gln Gln Lys Pro Gly Ser Ser Pro Lys Pro Trp Ile Tyr
            35                  40                  45

Arg Thr Ser Asn Leu Ala Ser Gly Val Pro Gly Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Tyr His Ser Tyr Pro Pro Thr
                85                  90                  95

Phe Gly Gly Gly Thr Lys Leu Glu Ile Lys
            100                 105

<210> SEQ ID NO 7
<211> LENGTH: 354
<212> TYPE: DNA
```

```
<213> ORGANISM: Artificial Sequence
<220> FEATURE:
<223> OTHER INFORMATION: Nucleic acid sequence of murine anti-DR5-05
      variable heavy chain

<400> SEQUENCE: 7
gaggtccagc tgcagcagtc tggggcagag cttgtgaagc caggggcctc agtcaagttg      60
ttctgcacag cttctggctt caacattaaa gacacccata tacactgggt gaaacagagg     120
cctgagcagg gcctggagtg gattggaagg attgatcctg cgaatggtaa tactgaatat     180
gacccgaagt tccagggcaa ggccactata agagtagaca catcctccga cacagcctac     240
ctgcagctca gcagcctgac atctgaggac actgccgtcc attattgtgc tagatggggg     300
actaacgtct attttgctta ctggggtcaa ggaacctcgg tcaccgtctc ctca           354

<210> SEQ ID NO 8
<211> LENGTH: 118
<212> TYPE: PRT
<213> ORGANISM: Artificial Sequence
<220> FEATURE:
<223> OTHER INFORMATION: Amino acid sequence of murine anti-DR5-05
      variable heavy chain

<400> SEQUENCE: 8

Glu Val Gln Leu Gln Gln Ser Gly Ala Glu Leu Val Lys Pro Gly Ala
1               5                   10                  15

Ser Val Lys Leu Phe Cys Thr Ala Ser Gly Phe Asn Ile Lys Asp Thr
            20                  25                  30

His Ile His Trp Val Lys Gln Arg Pro Glu Gln Gly Leu Glu Trp Ile
        35                  40                  45

Gly Arg Ile Asp Pro Ala Asn Gly Asn Thr Glu Tyr Asp Pro Lys Phe
    50                  55                  60

Gln Gly Lys Ala Thr Ile Arg Val Asp Thr Ser Ser Asp Thr Ala Tyr
65                  70                  75                  80

Leu Gln Leu Ser Ser Leu Thr Ser Glu Asp Thr Ala Val His Tyr Cys
                85                  90                  95

Ala Arg Trp Gly Thr Asn Val Tyr Phe Ala Tyr Trp Gly Gln Gly Thr
            100                 105                 110

Ser Val Thr Val Ser Ser
        115

<210> SEQ ID NO 9
<211> LENGTH: 993
<212> TYPE: DNA
<213> ORGANISM: Artificial Sequence
<220> FEATURE:
<223> OTHER INFORMATION: Nucleic acid sequence of human anti-DR5-01 or
      human anti-DR5-05 constant heavy chain

<400> SEQUENCE: 9
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtcgtgacc gtgccctcca gcagcttggg cacccagacc     240
tacatctgca acgtgaatca caagcccagc aacaccaagg tggacaagaa agttgagccc     300
aaatcttgtg acaaaactca cacatgccca ccgtgcccag cacctgaact cctgggggga     360
ccgtcagtct tcctcttccc cccaaaaccc aaggacaccc tcatgatctc ccggacccct     420
```

```
gaggtcacat gcgtggtggt ggacgtgagc cacgaagacc ctgaggtcaa gttcaactgg    480
tacgtggacg gcgtggaggt gcataatgcc aagacaaagc cgcggggagga gcagtacaac   540 agcacgtacc gtgtggtcag cgtcctcacc gtcctgcacc aggactggct gaatggcaag    600
gagtacaagt gcaaggtctc caacaaagcc ctcccagccc ccatcgagaa aaccatctcc    660
aaagccaaag ggcagccccg agaaccacag gtgtacaccc tgcccccatc ccgggatgag    720
ctgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctac agcaagctca ccgtggacaa gagcaggtgg    900
cagcagggga acgtcttctc atgctccgtg atgcatgagg ctctgcacaa ccactacacg    960
cagaagagcc tctccctgtc tccgggtaaa tag                                 993
```

<210> SEQ ID NO 10
<211> LENGTH: 330
<212> TYPE: PRT
<213> ORGANISM: Artificial Sequence
<220> FEATURE:
<223> OTHER INFORMATION: Amino acid sequence of human anti-DR5-01 or
      human anti-DR5-05 constant heavy chain

<400> SEQUENCE: 10

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255
```

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 11
<211> LENGTH: 324
<212> TYPE: DNA
<213> ORGANISM: Artificial Sequence
<220> FEATURE:
<223> OTHER INFORMATION: Nucleic acid sequence of human anti-DR5-01 or
      human anti-DR5-05 constant light chain

<400> SEQUENCE: 11
cgaactgtgg ctgcaccatc tgtcttcatc ttcccgccat ctgatgagca gttgaaatct      60
ggaactgcct ctgttgtgtg cctgctgaat aacttctatc ccagagaggc caaagtacag     120
tggaaggtgg ataacgccct ccaatcgggt aactcccagg agagtgtcac agagcaggac     180
agcaaggaca gcacctacag cctcagcagc accctgacgc tgagcaaagc agactacgag     240
aaacacaaag tctacgcctg cgaagtcacc catcagggcc tgagctcgcc cgtcacaaag     300
agcttcaaca ggggagagtg ttag                                           324

<210> SEQ ID NO 12
<211> LENGTH: 107
<212> TYPE: PRT
<213> ORGANISM: Artificial Sequence
<220> FEATURE:
<223> OTHER INFORMATION: Amino acid sequence of human anti-DR5-01 or
      human anti-DR5-05 constant light chain

<400> SEQUENCE: 12

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 13
<211> LENGTH: 8
<212> TYPE: PRT
<213> ORGANISM: Artificial Sequence
<220> FEATURE:
<223> OTHER INFORMATION: murine anti-DR5-01 heavy chain CDR1 (IGMT
      numbering system)
```

```
<400> SEQUENCE: 13

Gly Phe Asn Ile Lys Asp Thr Phe
1               5

<210> SEQ ID NO 14
<211> LENGTH: 8
<212> TYPE: PRT
<213> ORGANISM: Artificial Sequence
<220> FEATURE:
<223> OTHER INFORMATION: murine anti-DR5-01 or anti-DR5-05 heavy chain
      CDR2 (IGMT or Common numbering system)

<400> SEQUENCE: 14

Ile Asp Pro Ala Asn Gly Asn Thr
1               5

<210> SEQ ID NO 15
<211> LENGTH: 11
<212> TYPE: PRT
<213> ORGANISM: Artificial Sequence
<220> FEATURE:
<223> OTHER INFORMATION: murine anti-DR5-01 heavy chain CDR3 (IGMT
      numbering system)

<400> SEQUENCE: 15

Val Arg Gly Leu Tyr Thr Tyr Tyr Phe Asp Tyr
1               5                   10

<210> SEQ ID NO 16
<211> LENGTH: 6
<212> TYPE: PRT
<213> ORGANISM: Artificial Sequence
<220> FEATURE:
<223> OTHER INFORMATION: murine anti-DR5-01 light chain CDR1 (IGMT
      or Common numbering system)

<400> SEQUENCE: 16

Gln Ser Ile Ser Asn Asn
1               5

<210> SEQ ID NO 17
<211> LENGTH: 9
<212> TYPE: PRT
<213> ORGANISM: Artificial Sequence
<220> FEATURE:
<223> OTHER INFORMATION: murine anti-DR5-01 light chain CDR3 (IGMT,
      Kabat or Common numbering system)

<400> SEQUENCE: 17

Gln Gln Gly Asn Ser Trp Pro Tyr Thr
1               5

<210> SEQ ID NO 18
<211> LENGTH: 8
<212> TYPE: PRT
<213> ORGANISM: Artificial Sequence
<220> FEATURE:
<223> OTHER INFORMATION: murine anti-DR5-05 heavy chain CDR1 (IGMT
      numbering system)

<400> SEQUENCE: 18

Gly Phe Asn Ile Lys Asp Thr His
1               5

<210> SEQ ID NO 19
<211> LENGTH: 11
<212> TYPE: PRT
```

<210> SEQ ID NO 19
<211> LENGTH: (not shown)
<212> TYPE: PRT
<213> ORGANISM: Artificial Sequence
<220> FEATURE:
<223> OTHER INFORMATION: murine anti-DR5-05 heavy chain CDR3 (IGMT numbering system)

<400> SEQUENCE: 19

Ala Arg Trp Gly Thr Asn Val Tyr Phe Ala Tyr
1               5                   10

<210> SEQ ID NO 20
<211> LENGTH: 5
<212> TYPE: PRT
<213> ORGANISM: Artificial Sequence
<220> FEATURE:
<223> OTHER INFORMATION: murine anti-DR5-05 light chain CDR1 (IGMT or Common numbering system)

<400> SEQUENCE: 20

Ser Ser Val Ser Tyr
1               5

<210> SEQ ID NO 21
<211> LENGTH: 9
<212> TYPE: PRT
<213> ORGANISM: Artificial Sequence
<220> FEATURE:
<223> OTHER INFORMATION: murine anti-DR5-05 light chain CDR3 (IGMT, Kabat or Common numbering system)

<400> SEQUENCE: 21

Gln Gln Tyr His Ser Tyr Pro Pro Thr
1               5

<210> SEQ ID NO 22
<211> LENGTH: 5
<212> TYPE: PRT
<213> ORGANISM: Artificial Sequence
<220> FEATURE:
<223> OTHER INFORMATION: murine anti-DR5-01 heavy chain CDR1 (Kabat numbering system)

<400> SEQUENCE: 22

Asp Thr Phe Ile His
1               5

<210> SEQ ID NO 23
<211> LENGTH: 17
<212> TYPE: PRT
<213> ORGANISM: Artificial Sequence
<220> FEATURE:
<223> OTHER INFORMATION: murine anti-DR5-01 heavy chain CDR2 (Kabat numbering system)

<400> SEQUENCE: 23

Arg Ile Asp Pro Ala Asn Gly Asn Thr Lys Tyr Asp Pro Lys Phe Gln
1               5                   10                  15

Gly

<210> SEQ ID NO 24
<211> LENGTH: 9
<212> TYPE: PRT
<213> ORGANISM: Artificial Sequence
<220> FEATURE:
<223> OTHER INFORMATION: murine anti-DR5-01 heavy chain CDR3 (Kabat or Common numbering system)

<400> SEQUENCE: 24

```
Gly Leu Tyr Thr Tyr Tyr Phe Asp Tyr
1               5

<210> SEQ ID NO 25
<211> LENGTH: 11
<212> TYPE: PRT
<213> ORGANISM: Artificial Sequence
<220> FEATURE:
<223> OTHER INFORMATION: murine anti-DR5-01 light chain CDR1 (Kabat
      numbering system)

<400> SEQUENCE: 25

Arg Ala Ser Gln Ser Ile Ser Asn Asn Leu His
1               5                   10

<210> SEQ ID NO 26
<211> LENGTH: 7
<212> TYPE: PRT
<213> ORGANISM: Artificial Sequence
<220> FEATURE:
<223> OTHER INFORMATION: murine anti-DR5-01 light chain CDR2 (Kabat
      numbering system)

<400> SEQUENCE: 26

Phe Ala Ser Gln Ser Ile Ser
1               5

<210> SEQ ID NO 27
<211> LENGTH: 5
<212> TYPE: PRT
<213> ORGANISM: Artificial Sequence
<220> FEATURE:
<223> OTHER INFORMATION: murine anti-DR5-05 heavy chain CDR1 (Kabat
      numbering system)

<400> SEQUENCE: 27

Asp Thr His Ile His
1               5

<210> SEQ ID NO 28
<211> LENGTH: 17
<212> TYPE: PRT
<213> ORGANISM: Artificial Sequence
<220> FEATURE:
<223> OTHER INFORMATION: murine anti-DR5-05 heavy chain CDR2 (Kabat
      numbering system)

<400> SEQUENCE: 28

Arg Ile Asp Pro Ala Asn Gly Asn Thr Glu Tyr Asp Pro Lys Phe Gln
1               5                   10                  15

Gly

<210> SEQ ID NO 29
<211> LENGTH: 9
<212> TYPE: PRT
<213> ORGANISM: Artificial Sequence
<220> FEATURE:
<223> OTHER INFORMATION: murine anti-DR5-05 heavy chain CDR3 (Kabat
      or Common numbering system)

<400> SEQUENCE: 29

Trp Gly Thr Asn Val Tyr Phe Ala Tyr
1               5

<210> SEQ ID NO 30
<211> LENGTH: 10
<212> TYPE: PRT
```

```
<213> ORGANISM: Artificial Sequence
<220> FEATURE:
<223> OTHER INFORMATION: murine anti-DR5-05 light chain CDR1 (Kabat
      numbering system)

<400> SEQUENCE: 30

Ser Ala Ser Ser Ser Val Ser Tyr Met Tyr
1               5                   10

<210> SEQ ID NO 31
<211> LENGTH: 7
<212> TYPE: PRT
<213> ORGANISM: Artificial Sequence
<220> FEATURE:
<223> OTHER INFORMATION: murine anti-DR5-05 light chain CDR2 (Kabat
      numbering system)

<400> SEQUENCE: 31

Arg Thr Ser Asn Leu Ala Ser
1               5

<210> SEQ ID NO 32
<211> LENGTH: 4
<212> TYPE: PRT
<213> ORGANISM: Artificial Sequence
<220> FEATURE:
<223> OTHER INFORMATION: murine anti-DR5-01 heavy chain CDR1 (Common
      numbering system)

<400> SEQUENCE: 32

Lys Asp Thr Phe
1

<210> SEQ ID NO 33
<211> LENGTH: 4
<212> TYPE: PRT
<213> ORGANISM: Artificial Sequence
<220> FEATURE:
<223> OTHER INFORMATION: murine anti-DR5-05 heavy chain CDR1 (Common
      numbering system)

<400> SEQUENCE: 33

Lys Asp Thr His
1

<210> SEQ ID NO 34
<211> LENGTH: 354
<212> TYPE: DNA
<213> ORGANISM: Artificial Sequence
<220> FEATURE:
<223> OTHER INFORMATION: Nucleic acid sequence of humanized anti-DR5-01
      variable heavy chain

<400> SEQUENCE: 34
gaggtgcaac tgcagcaatc aggagcagaa gtcgtaaagc ccggtgcctc cgttaaactt      60
agctgcaaag caagtgggtt taatatcaaa gatacattca tccattgggt caaacaggca     120
ccaggccagg gccttgaatg gatcggtcgc atcgacccag ctaacggaaa cactaagtat     180
gaccctaagt tccagggaaa ggctacaatt acaacagata catcctccaa taccgcttac     240
atggagctgt cttccttgcg gtctgaggat actgctgtgt attactgtgt acgtgggctg     300
tacacatatt acttcgatta ttggggccag gggactcttg taaccgtttc ctcc           354

<210> SEQ ID NO 35
<211> LENGTH: 118
<212> TYPE: PRT
```

<213> ORGANISM: Artificial Sequence
<220> FEATURE:
<223> OTHER INFORMATION: Amino acid sequence of humanized anti-DR5-01 variable heavy chain

<400> SEQUENCE: 35

```
Glu Val Gln Leu Gln Gln Ser Gly Ala Glu Val Val Lys Pro Gly Ala
1               5                   10                  15

Ser Val Lys Leu Ser Cys Lys Ala Ser Gly Phe Asn Ile Lys Asp Thr
            20                  25                  30

Phe Ile His Trp Val Lys Gln Ala Pro Gly Gln Gly Leu Glu Trp Ile
        35                  40                  45

Gly Arg Ile Asp Pro Ala Asn Gly Asn Thr Lys Tyr Asp Pro Lys Phe
    50                  55                  60

Gln Gly Lys Ala Thr Ile Thr Thr Asp Thr Ser Ser Asn Thr Ala Tyr
65                  70                  75                  80

Met Glu Leu Ser Ser Leu Arg Ser Glu Asp Thr Ala Val Tyr Tyr Cys
                85                  90                  95

Val Arg Gly Leu Tyr Thr Tyr Tyr Phe Asp Tyr Trp Gly Gln Gly Thr
            100                 105                 110

Leu Val Thr Val Ser Ser
        115
```

<210> SEQ ID NO 36
<211> LENGTH: 321
<212> TYPE: DNA
<213> ORGANISM: Artificial Sequence
<220> FEATURE:
<223> OTHER INFORMATION: Nucleic acid sequence of humanized anti-DR5-01 variable light chain

<400> SEQUENCE: 36

```
gagattgtta tgacacagtc ccctgctaca ttgagtgtta gtccaggcga aagagctaca      60
ctgtcatgta gggcctctca gtctattagc aataaacctgc actggtatca gcaaaagcca   120
ggtcaagccc ccaggctgct gattaagttt gcatctcaaa gtattacagg aatccctgct    180
cggttcagcg gctccgggag tggaaccgag tttacactca caatctcaag cctccagtcc    240
gaagacttcg ccgtatatta ctgtcagcag ggcaactctt ggccctacac cttcggtcag    300
ggaaccaagc tggagatcaa g                                              321
```

<210> SEQ ID NO 37
<211> LENGTH: 107
<212> TYPE: PRT
<213> ORGANISM: Artificial Sequence
<220> FEATURE:
<223> OTHER INFORMATION: Amino acid sequence of humanized anti-DR5-01 variable light chain

<400> SEQUENCE: 37

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Asn Asn
            20                  25                  30

Leu His Trp Tyr Gln Gln Lys Pro Gly Gln Ala Pro Arg Leu Leu Ile
        35                  40                  45

Lys Phe Ala Ser Gln Ser Ile Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80
```

Glu Asp Phe Ala Val Tyr Tyr Cys Gln Gln Gly Asn Ser Trp Pro Tyr
                85                  90                  95

Thr Phe Gly Gln Gly Thr Lys Leu Glu Ile Lys
            100                 105

<210> SEQ ID NO 38
<211> LENGTH: 354
<212> TYPE: DNA
<213> ORGANISM: Artificial Sequence
<220> FEATURE:
<223> OTHER INFORMATION: Nucleic acid sequence of humanized anti-DR5-05
      variable heavy chain

<400> SEQUENCE: 38
caagttcagt tggtacaatc aggtgcagaa gttaaaaagc caggggcatc tgttaaagtg        60
tcttgcaagg cctccggctt aatatcaag gacacacaca tgcattgggt gcgccaggcc       120
ccaggccagc gactggagtg gattggcgt attgaccccg ccaacggcaa caccgagtat       180
gaccagaagt tcagggccgt gtaaccatc accgtcgata cctcagcatc aaccgcttac       240
atggagcttt catctcttcg gtccgaagac acagccgtct attactgcgc tcgatgggga       300
acaaacgttt actttgcata ttggggtcag ggtactctcg tcaccgtgag cagt            354

<210> SEQ ID NO 39
<211> LENGTH: 118
<212> TYPE: PRT
<213> ORGANISM: Artificial Sequence
<220> FEATURE:
<223> OTHER INFORMATION: Amino acid sequence of humanized anti-DR5-05
      variable heavy chain

<400> SEQUENCE: 39

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

His Met His Trp Val Arg Gln Ala Pro Gly Gln Arg Leu Glu Trp Ile
        35                  40                  45

Gly Arg Ile Asp Pro Ala Asn Gly Asn Thr Glu Tyr Asp Gln Lys Phe
    50                  55                  60

Gln Gly Arg Val Thr Ile Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Thr Asn Val Tyr Phe Ala Tyr Trp Gly Gln Gly Thr
            100                 105                 110

Leu Val Thr Val Ser Ser
        115

<210> SEQ ID NO 40
<211> LENGTH: 318
<212> TYPE: DNA
<213> ORGANISM: Artificial Sequence
<220> FEATURE:
<223> OTHER INFORMATION: Nucleic acid sequence of humanized anti-DR5-05
      variable light chain

<400> SEQUENCE: 40
gatattcaac ttacacaatc tccctcttct ctctccgctt cagtagggga tagagtgacc        60
atcacttgct ctgcttcttc cagcgtgtca tatatgtatt ggtatcagca aaagcccggc       120

```
aaggcaccta aaccatggat ttacagaacc agcaatcttg ccagcggtgt tccaagtagg    180
tttagcggct ccggctctgg tacagacttt accctgacta tctcctctct ccagcccgag    240
gattttgcca catattactg ccagcaatac cattcttacc ctccaacttt tggaggtggc    300
actaaggtgg agatcaag                                                  318

<210> SEQ ID NO 41
<211> LENGTH: 106
<212> TYPE: PRT
<213> ORGANISM: Artificial Sequence
<220> FEATURE:
<223> OTHER INFORMATION: Amino acid sequence of humanized anti-DR5-05
      variable light chain

<400> SEQUENCE: 41

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

Tyr Trp Tyr Gln Gln Lys Pro Gly Lys Ala Pro Lys Pro Trp Ile Tyr
        35                  40                  45

Arg Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Tyr His Ser Tyr Pro Pro Thr
                85                  90                  95

Phe Gly Gly Gly Thr Lys Val Glu Ile Lys
            100                 105
```